United States Patent
Reynolds et al.

(10) Patent No.: US 9,782,114 B2
(45) Date of Patent: Oct. 10, 2017

(54) DEVICES AND METHODS FOR BODY FLUID SAMPLING AND ANALYSIS

(75) Inventors: Paul D. Reynolds, Palo Alto, CA (US); Raul Escutia, Sunnyvale, CA (US); John F. Larkin, Monterey, CA (US); Charles Hu, Palo Alto, CA (US); Michael F. Tomasco, Morgan Hill, CA (US); Daniel R. Bloom, Alameda, CA (US); Joseph A. Vivolo, San Francisco, CA (US); Richard M. Wiard, Campbell, CA (US)

(73) Assignee: Intuity Medical, Inc., Sunnyvale, CA (US)

( * ) Notice: Subject to any disclaimer, the term of this patent is extended or adjusted under 35 U.S.C. 154(b) by 742 days.

(21) Appl. No.: 13/566,886

(22) Filed: Aug. 3, 2012

(65) Prior Publication Data
US 2013/0172698 A1    Jul. 4, 2013

Related U.S. Application Data

(60) Provisional application No. 61/514,872, filed on Aug. 3, 2011.

(51) Int. Cl.
*A61B 5/1455* (2006.01)
*A61B 5/157* (2006.01)
(Continued)

(52) U.S. Cl.
CPC ............ *A61B 5/157* (2013.01); *A61B 5/1455* (2013.01); *A61B 5/14507* (2013.01);
(Continued)

(58) Field of Classification Search
CPC .................................................. A61B 5/1455
See application file for complete search history.

(56) References Cited

U.S. PATENT DOCUMENTS

| 842,690 A | 1/1907 | Oswalt |
|---|---|---|
| D137,874 S | 5/1944 | Partridge |

(Continued)

FOREIGN PATENT DOCUMENTS

| CA | 2 201 530 A1 | 9/1997 |
|---|---|---|
| CA | 2 513 465 A1 | 8/2004 |

(Continued)

OTHER PUBLICATIONS

ADA Consensus Development Panel. (Jan.-Feb. 1987). "Consensus Statement on Self-Monitoring of Blood Glucose," *Diabetes Care* 10(1):95-99.

(Continued)

*Primary Examiner* — Eric Winakur
*Assistant Examiner* — Marjan Fardanesh
(74) *Attorney, Agent, or Firm* — Cooley LLP

(57) ABSTRACT

Described here are meters and methods for sampling, transporting, and/or analyzing a fluid sample. The meters may include a meter housing and a cartridge. In some instances, the meter may include a tower which may engage one or more portions of a cartridge. The meter housing may include an imaging system, which may or may not be included in the tower. The cartridge may include one or more sampling arrangements, which may be configured to collect a fluid sample from a sampling site. A sampling arrangement may include a skin-penetration member, a hub, and a quantification member.

13 Claims, 23 Drawing Sheets

(51) Int. Cl.

| | | |
|---|---|---|
| A61B 5/00 | (2006.01) | |
| A61B 5/151 | (2006.01) | |
| A61B 5/145 | (2006.01) | |
| G01N 15/06 | (2006.01) | |
| G01N 21/03 | (2006.01) | |
| G01N 33/487 | (2006.01) | |
| G01N 21/78 | (2006.01) | |
| A61B 5/15 | (2006.01) | |

(52) U.S. Cl.
CPC ...... *A61B 5/14532* (2013.01); *A61B 5/14546* (2013.01); *A61B 5/150022* (2013.01); *A61B 5/150068* (2013.01); *A61B 5/150083* (2013.01); *A61B 5/150099* (2013.01); *A61B 5/15109* (2013.01); *A61B 5/15111* (2013.01); *A61B 5/15113* (2013.01); *A61B 5/150114* (2013.01); *A61B 5/15117* (2013.01); *A61B 5/15151* (2013.01); *A61B 5/15161* (2013.01); *A61B 5/15163* (2013.01); *A61B 5/15176* (2013.01); *A61B 5/15182* (2013.01); *A61B 5/150183* (2013.01); *A61B 5/150358* (2013.01); *A61B 5/150389* (2013.01); *A61B 5/150419* (2013.01); *A61B 5/150519* (2013.01); *A61B 5/150572* (2013.01); *A61B 5/150755* (2013.01); *A61B 5/150786* (2013.01); *A61B 5/150809* (2013.01); *A61B 5/150816* (2013.01); *A61B 5/150824* (2013.01); *A61B 5/150984* (2013.01); *A61B 5/742* (2013.01); *G01N 15/0612* (2013.01); *G01N 21/03* (2013.01); *G01N 21/78* (2013.01); *G01N 33/487* (2013.01); *A61B 5/14535* (2013.01); *A61B 5/150305* (2013.01); *A61B 2562/0295* (2013.01)

(56) References Cited

U.S. PATENT DOCUMENTS

| | | | |
|---|---|---|---|
| 2,749,797 A | 3/1950 | Harks | |
| 3,092,465 A | 6/1963 | Adams, Jr. | |
| 3,310,002 A | 3/1967 | Wilburn | |
| 3,620,209 A | 11/1971 | Kravitz | |
| 3,623,475 A | 11/1971 | Sanz et al. | |
| 3,626,929 A | 12/1971 | Sanz et al. | |
| 3,630,957 A | 12/1971 | Rey | |
| D223,165 S | 3/1972 | Komendat | |
| 3,723,064 A | 3/1973 | Liotta | |
| 3,741,197 A | 6/1973 | Sanz et al. | |
| 3,961,898 A | 6/1976 | Neeley et al. | |
| 3,992,158 A | 11/1976 | Przybylowicz et al. | |
| 4,014,328 A | 3/1977 | Cluff et al. | |
| 4,042,335 A | 8/1977 | Clement | |
| 4,057,394 A | 11/1977 | Genshaw | |
| 4,109,655 A | 8/1978 | Chacornac | |
| 4,253,083 A | 2/1981 | Imamura | |
| 4,254,083 A | 3/1981 | Columbus | |
| 4,258,001 A | 3/1981 | Pierce et al. | |
| 4,260,257 A | 4/1981 | Neeley et al. | |
| 4,289,459 A | 9/1981 | Neeley et al. | |
| 4,321,397 A | 3/1982 | Nix et al. | |
| 4,350,762 A | 9/1982 | DeLuca et al. | |
| 4,394,512 A | 7/1983 | Batz | |
| 4,414,975 A | 11/1983 | Ryder et al. | |
| 4,416,279 A | 11/1983 | Lindner et al. | |
| 4,418,037 A | 11/1983 | Katsuyama et al. | |
| 4,422,941 A | 12/1983 | Vaughan, Jr. et al. | |
| 4,429,700 A | 2/1984 | Thees et al. | |
| 4,627,445 A | 12/1986 | Garcia et al. | |
| 4,637,403 A | 1/1987 | Garcia et al. | |
| 4,637,406 A | 1/1987 | Guinn et al. | |
| 4,653,513 A | 3/1987 | Dombrowski | |
| 4,661,319 A | 4/1987 | Lape | |
| 4,702,261 A | 10/1987 | Cornell et al. | |
| 4,711,250 A | 12/1987 | Gilbaugh, Jr. et al. | |
| 4,737,458 A | 4/1988 | Batz et al. | |
| 4,767,415 A | 8/1988 | Duffy | |
| 4,774,192 A | 9/1988 | Terminiello et al. | |
| 4,787,398 A | 11/1988 | Garcia et al. | |
| 4,790,979 A | 12/1988 | Terminiello et al. | |
| 4,794,926 A | 1/1989 | Munsch et al. | |
| 4,815,843 A | 3/1989 | Tiefenthaler et al. | |
| 4,829,470 A | 5/1989 | Wang | |
| 4,844,095 A | 7/1989 | Chiodo et al. | |
| 4,846,785 A | 7/1989 | Cassou et al. | |
| 4,887,306 A | 12/1989 | Hwang et al. | |
| 4,920,977 A | 5/1990 | Haynes | |
| 4,929,426 A | 5/1990 | Bodai et al. | |
| 4,930,525 A | 6/1990 | Palestrant | |
| 4,935,346 A | 6/1990 | Phillips | |
| 4,953,552 A | 9/1990 | De Marzo | |
| 4,966,646 A | 10/1990 | Zdeblick | |
| 4,983,178 A | 1/1991 | Schnell | |
| 4,995,402 A | 2/1991 | Smith | |
| 5,029,583 A | 7/1991 | Meserol | |
| 5,035,704 A | 7/1991 | Lambert et al. | |
| 5,049,487 A | 9/1991 | Phillips et al. | |
| 5,050,617 A | 9/1991 | Columbus et al. | |
| 5,059,394 A | 10/1991 | Phillips et al. | |
| 5,077,199 A | 12/1991 | Basagni et al. | |
| 5,094,943 A | 3/1992 | Siedel et al. | |
| 5,110,724 A | 5/1992 | Hewett | |
| 5,114,350 A | 5/1992 | Hewett | |
| 5,116,759 A | 5/1992 | Klainer et al. | |
| 5,131,404 A | 7/1992 | Neeley et al. | |
| 5,141,868 A | 8/1992 | Shanks et al. | |
| 5,145,565 A | 9/1992 | Kater et al. | |
| 5,146,437 A | 9/1992 | Boucheron | |
| 5,153,416 A | 10/1992 | Neeley | |
| 5,164,575 A | 11/1992 | Neeley et al. | |
| 5,166,498 A | 11/1992 | Neeley | |
| 5,174,291 A | 12/1992 | Schoonen et al. | |
| 5,176,632 A | 1/1993 | Bernardi | |
| 5,179,005 A | 1/1993 | Phillips et al. | |
| 5,183,741 A | 2/1993 | Arai et al. | |
| 5,196,302 A | 3/1993 | Kidwell | |
| 5,208,163 A | 5/1993 | Charlton et al. | |
| 5,213,966 A | 5/1993 | Vuorinen et al. | |
| 5,217,480 A | 6/1993 | Haber et al. | |
| 5,218,966 A | 6/1993 | Yamasawa | |
| 5,223,219 A | 6/1993 | Subramanian et al. | |
| 5,228,972 A | 7/1993 | Osaka et al. | |
| 5,234,818 A | 8/1993 | Zimmermann et al. | |
| 5,241,969 A | 9/1993 | Carson et al. | |
| 5,251,126 A | 10/1993 | Kahn et al. | |
| D341,848 S | 11/1993 | Bigelow et al. | |
| 5,269,800 A | 12/1993 | Davis, Jr. | |
| 5,275,159 A | 1/1994 | Griebel | |
| 5,278,079 A | 1/1994 | Gubinski et al. | |
| 5,279,294 A | 1/1994 | Anderson et al. | |
| 5,288,646 A | 2/1994 | Lundsgaard et al. | |
| 5,299,571 A | 4/1994 | Mastrototaro | |
| 5,301,686 A | 4/1994 | Newman | |
| 5,302,513 A | 4/1994 | Miike et al. | |
| 5,304,468 A | 4/1994 | Phillips et al. | |
| 5,306,623 A | 4/1994 | Kiser et al. | |
| 5,308,767 A | 5/1994 | Terashima | |
| 5,314,441 A | 5/1994 | Cusack et al. | |
| 5,320,607 A | 6/1994 | Ishibashi | |
| 5,354,537 A | 10/1994 | Moreno | |
| 5,360,595 A | 11/1994 | Bell et al. | |
| 5,368,047 A | 11/1994 | Suzuki et al. | |
| 5,383,512 A | 1/1995 | Jarvis | |
| 5,390,671 A | 2/1995 | Lord et al. | |
| 5,395,388 A | 3/1995 | Schraga | |
| 5,399,316 A | 3/1995 | Yamada | |
| 5,401,110 A | 3/1995 | Neeley | |
| 5,402,798 A | 4/1995 | Swierczek et al. | |
| 5,426,032 A | 6/1995 | Phillips et al. | |
| 5,441,513 A | 8/1995 | Roth | |
| 5,451,350 A | 9/1995 | Macho et al. | |
| 5,458,140 A | 10/1995 | Eppstein et al. | |

(56) References Cited

U.S. PATENT DOCUMENTS

| | | |
|---|---|---|
| 5,460,777 A | 10/1995 | Kitajima et al. |
| 5,460,968 A | 10/1995 | Yoshida et al. |
| 5,482,473 A | 1/1996 | Lord et al. |
| 5,506,200 A | 4/1996 | Hirschkoff et al. |
| 5,507,288 A | 4/1996 | Böcker et al. |
| 5,508,200 A | 4/1996 | Tiffany et al. |
| 5,510,266 A | 4/1996 | Bonner et al. |
| 5,514,152 A | 5/1996 | Smith |
| 5,525,518 A | 6/1996 | Lundsgaard et al. |
| 5,563,042 A | 10/1996 | Phillips et al. |
| 5,568,806 A | 10/1996 | Cheney, II et al. |
| 5,569,287 A | 10/1996 | Tezuka et al. |
| 5,575,403 A | 11/1996 | Charlton et al. |
| 5,577,499 A | 11/1996 | Teves |
| 5,582,184 A | 12/1996 | Erickson et al. |
| 5,586,553 A | 12/1996 | Halili et al. |
| 5,591,139 A | 1/1997 | Lin et al. |
| 5,593,838 A | 1/1997 | Zanzucchi et al. |
| 5,611,809 A | 3/1997 | Marshall et al. |
| 5,624,458 A | 4/1997 | Lipscher |
| 5,630,986 A | 5/1997 | Charlton et al. |
| 5,632,410 A | 5/1997 | Moulton et al. |
| 5,636,632 A | 6/1997 | Bommannan et al. |
| 5,647,851 A | 7/1997 | Pokras |
| 5,658,515 A | 8/1997 | Lee et al. |
| 5,660,791 A | 8/1997 | Brenneman et al. |
| 5,670,031 A | 9/1997 | Hintsche et al. |
| 5,676,850 A | 10/1997 | Reed et al. |
| 5,680,858 A | 10/1997 | Hansen et al. |
| 5,681,484 A | 10/1997 | Zanzucchi et al. |
| 5,682,233 A | 10/1997 | Brinda |
| 5,697,901 A | 12/1997 | Eriksson |
| 5,700,695 A | 12/1997 | Yassinzadeh et al. |
| 5,701,181 A | 12/1997 | Boiarski et al. |
| 5,701,910 A | 12/1997 | Powles et al. |
| D389,761 S | 1/1998 | Thomas |
| 5,705,018 A | 1/1998 | Hartley |
| 5,708,787 A | 1/1998 | Nakano et al. |
| 5,715,417 A | 2/1998 | Gardien et al. |
| 5,730,753 A | 3/1998 | Morita |
| 5,735,273 A | 4/1998 | Kurnik et al. |
| 5,736,103 A | 4/1998 | Pugh |
| 5,741,211 A | 4/1998 | Renirie et al. |
| 5,746,217 A | 5/1998 | Erickson et al. |
| 5,746,720 A | 5/1998 | Stouder, Jr. |
| 5,757,666 A | 5/1998 | Schreiber et al. |
| 5,759,364 A | 6/1998 | Charlton et al. |
| 5,766,066 A | 6/1998 | Ranniger |
| 5,771,890 A | 6/1998 | Tamada |
| 5,797,693 A | 8/1998 | Jaeger |
| 5,800,420 A | 9/1998 | Gross et al. |
| 5,801,057 A | 9/1998 | Smart et al. |
| 5,807,375 A | 9/1998 | Gross et al. |
| 5,820,570 A | 10/1998 | Erickson et al. |
| 5,827,183 A | 10/1998 | Kurnik et al. |
| 5,840,020 A | 11/1998 | Heinonen et al. |
| 5,841,126 A | 11/1998 | Fossum et al. |
| 5,843,692 A | 12/1998 | Phillips et al. |
| 5,846,837 A | 12/1998 | Thym et al. |
| 5,851,215 A | 12/1998 | Mawhirt et al. |
| 5,854,074 A | 12/1998 | Charlton et al. |
| D403,975 S | 1/1999 | Douglas et al. |
| 5,855,801 A | 1/1999 | Lin et al. |
| 5,856,195 A | 1/1999 | Charlton et al. |
| 5,858,194 A | 1/1999 | Bell |
| 5,866,281 A | 2/1999 | Guckel et al. |
| 5,871,494 A | 2/1999 | Simons et al. |
| 5,879,310 A | 3/1999 | Sopp et al. |
| 5,879,326 A | 3/1999 | Godshall et al. |
| 5,879,367 A | 3/1999 | Latterell et al. |
| 5,885,839 A | 3/1999 | Lingane et al. |
| 5,891,053 A | 4/1999 | Sesekura |
| 5,893,870 A | 4/1999 | Talen et al. |
| D411,621 S | 6/1999 | Eisenbarth et al. |
| 5,911,711 A | 6/1999 | Pelkey |
| 5,911,737 A | 6/1999 | Lee et al. |
| 5,912,139 A | 6/1999 | Iwata et al. |
| 5,925,021 A | 7/1999 | Castellano et al. |
| 5,928,207 A | 7/1999 | Pisano et al. |
| 5,930,873 A | 8/1999 | Wyser |
| 5,938,679 A | 8/1999 | Freeman et al. |
| 5,945,678 A | 8/1999 | Yanagisawa |
| 5,951,492 A | 9/1999 | Douglas et al. |
| 5,951,493 A | 9/1999 | Douglas et al. |
| 5,951,521 A | 9/1999 | Mastrototaro et al. |
| 5,954,685 A | 9/1999 | Tierney |
| 5,962,215 A | 10/1999 | Douglas et al. |
| 5,968,760 A | 10/1999 | Phillips et al. |
| 5,968,765 A | 10/1999 | Grage et al. |
| 5,968,836 A | 10/1999 | Matzinger et al. |
| 5,971,941 A | 10/1999 | Simons et al. |
| 5,972,294 A | 10/1999 | Smith et al. |
| 5,986,754 A | 11/1999 | Harding |
| 5,989,409 A | 11/1999 | Kurnik et al. |
| 5,993,189 A | 11/1999 | Mueller et al. |
| D417,504 S | 12/1999 | Love et al. |
| 6,001,067 A | 12/1999 | Shults et al. |
| 6,005,545 A | 12/1999 | Nishida et al. |
| 6,010,463 A | 1/2000 | Lauks et al. |
| 6,010,519 A | 1/2000 | Mawhirt et al. |
| 6,014,135 A | 1/2000 | Fernandes |
| 6,014,577 A | 1/2000 | Henning et al. |
| 6,023,629 A | 2/2000 | Tamada |
| 6,027,459 A | 2/2000 | Shain et al. |
| 6,030,827 A | 2/2000 | Davis et al. |
| 6,032,059 A | 2/2000 | Henning et al. |
| 6,036,924 A | 3/2000 | Simons et al. |
| 6,041,253 A | 3/2000 | Kost et al. |
| 6,045,753 A | 4/2000 | Loewy et al. |
| 6,048,352 A | 4/2000 | Douglas et al. |
| 6,050,988 A | 4/2000 | Zuck |
| 6,056,701 A | 5/2000 | Duchon et al. |
| 6,056,734 A | 5/2000 | Jacobsen et al. |
| 6,058,321 A | 5/2000 | Swayze et al. |
| 6,059,815 A | 5/2000 | Lee et al. |
| 6,061,128 A | 5/2000 | Zweig et al. |
| 6,063,039 A | 5/2000 | Cunningham et al. |
| 6,071,251 A | 6/2000 | Cunningham et al. |
| 6,071,294 A | 6/2000 | Simons et al. |
| 6,077,660 A | 6/2000 | Wong et al. |
| 6,080,116 A | 6/2000 | Erickson et al. |
| 6,083,196 A | 7/2000 | Trautman et al. |
| 6,086,544 A | 7/2000 | Hibner et al. |
| 6,090,790 A | 7/2000 | Eriksson |
| 6,091,975 A | 7/2000 | Daddona et al. |
| 6,093,156 A | 7/2000 | Cunningham et al. |
| 6,097,831 A | 8/2000 | Wieck et al. |
| 6,099,484 A | 8/2000 | Douglas et al. |
| 6,100,107 A | 8/2000 | Lei et al. |
| 6,102,933 A | 8/2000 | Lee et al. |
| 6,103,033 A | 8/2000 | Say et al. |
| 6,103,197 A | 8/2000 | Werner |
| 6,106,751 A | 8/2000 | Talbot et al. |
| 6,118,126 A | 9/2000 | Zanzucchi |
| 6,120,676 A | 9/2000 | Heller et al. |
| 6,123,861 A | 9/2000 | Santini, Jr. et al. |
| 6,126,899 A | 10/2000 | Woudenberg et al. |
| 6,132,449 A | 10/2000 | Lum et al. |
| 6,139,562 A | 10/2000 | Mauze et al. |
| 6,142,939 A | 11/2000 | Eppstein et al. |
| 6,152,942 A | 11/2000 | Brenneman et al. |
| 6,162,639 A | 12/2000 | Douglas |
| 6,172,743 B1 | 1/2001 | Kley et al. |
| 6,175,752 B1 | 1/2001 | Say et al. |
| 6,176,865 B1 | 1/2001 | Mauze et al. |
| 6,183,434 B1 | 2/2001 | Eppstein et al. |
| 6,183,489 B1 | 2/2001 | Douglas et al. |
| 6,187,210 B1 | 2/2001 | Lebouiz et al. |
| 6,192,891 B1 | 2/2001 | Gravel et al. |
| 6,193,873 B1 | 2/2001 | Ohara et al. |
| 6,200,296 B1 | 3/2001 | Dibiasi et al. |
| 6,206,841 B1 | 3/2001 | Cunningham et al. |
| 6,214,626 B1 | 4/2001 | Meller et al. |
| 6,219,574 B1 | 4/2001 | Cormier et al. |

(56) References Cited

U.S. PATENT DOCUMENTS

| | | |
|---|---|---|
| 6,228,100 B1 | 5/2001 | Schraga |
| 6,230,051 B1 | 5/2001 | Cormier et al. |
| 6,231,531 B1 | 5/2001 | Lum et al. |
| 6,241,862 B1 | 6/2001 | McAleer et al. |
| 6,242,207 B1 | 6/2001 | Douglas et al. |
| 6,245,215 B1 | 6/2001 | Douglas et al. |
| 6,251,083 B1 | 6/2001 | Yum et al. |
| 6,251,260 B1 | 6/2001 | Heller et al. |
| 6,254,586 B1 | 7/2001 | Mann et al. |
| 6,255,061 B1 | 7/2001 | Mori et al. |
| 6,256,533 B1 | 7/2001 | Yuzhakov et al. |
| 6,268,162 B1 | 7/2001 | Phillips et al. |
| 6,271,045 B1 | 8/2001 | Douglas et al. |
| 6,272,364 B1 | 8/2001 | Kurnik |
| 6,283,926 B1 | 9/2001 | Cunningham et al. |
| 6,289,230 B1 | 9/2001 | Chaiken et al. |
| 6,298,254 B2 | 10/2001 | Tamada |
| 6,299,578 B1 | 10/2001 | Kurnik et al. |
| 6,299,757 B1 | 10/2001 | Feldman et al. |
| 6,306,104 B1 | 10/2001 | Cunningham et al. |
| 6,309,351 B1 | 10/2001 | Kurnik et al. |
| D450,711 S | 11/2001 | Istvan et al. |
| 6,312,612 B1 | 11/2001 | Sherman et al. |
| 6,312,888 B1 | 11/2001 | Wong et al. |
| 6,315,738 B1 | 11/2001 | Nishikawa et al. |
| 6,322,808 B1 | 11/2001 | Trautman et al. |
| 6,329,161 B1 | 12/2001 | Heller et al. |
| 6,331,266 B1 | 12/2001 | Powell et al. |
| 6,332,871 B1 | 12/2001 | Douglas et al. |
| 6,334,856 B1 | 1/2002 | Allen et al. |
| 6,350,273 B1 | 2/2002 | Minagawa et al. |
| 6,352,514 B1 | 3/2002 | Douglas et al. |
| 6,356,776 B1 | 3/2002 | Berner et al. |
| 6,358,265 B1 | 3/2002 | Thorne, Jr. et al. |
| 6,364,890 B1 | 4/2002 | Lum et al. |
| 6,375,626 B1 | 4/2002 | Allen et al. |
| 6,375,627 B1 | 4/2002 | Mauze et al. |
| 6,379,969 B1 | 4/2002 | Mauze et al. |
| 6,391,005 B1 | 5/2002 | Lum et al. |
| 6,391,645 B1 | 5/2002 | Huang et al. |
| 6,402,704 B1 | 6/2002 | McMorrow |
| 6,409,679 B2 | 6/2002 | Pyo |
| 6,428,664 B1 | 8/2002 | BhulLar et al. |
| 6,449,608 B1 | 9/2002 | Morita et al. |
| 6,455,324 B1 | 9/2002 | Douglas |
| 6,493,069 B1 | 12/2002 | Nagashimada |
| 6,500,134 B1 | 12/2002 | Cassone |
| 6,520,973 B1 | 2/2003 | McGarry |
| 6,530,892 B1 | 3/2003 | Kelly |
| 6,537,243 B1 | 3/2003 | Henning et al. |
| 6,540,675 B2 | 4/2003 | Aceti et al. |
| 6,544,475 B1 | 4/2003 | Douglas et al. |
| 6,549,796 B2 | 4/2003 | Sohrab |
| 6,555,061 B1 | 4/2003 | Leong et al. |
| 6,558,624 B1 | 5/2003 | Lemmon et al. |
| 6,579,690 B1 | 6/2003 | Bonnecaze et al. |
| 6,589,260 B1 | 7/2003 | Schmelzeisen-Redeker et al. |
| 6,591,125 B1 | 7/2003 | Buse et al. |
| 6,602,205 B1 | 8/2003 | Erickson et al. |
| 6,612,111 B1 | 9/2003 | Hodges et al. |
| 6,616,616 B2 | 9/2003 | Fritz et al. |
| 6,626,874 B1 | 9/2003 | Duchamp |
| 6,656,167 B2 | 12/2003 | Numao et al. |
| 6,679,852 B1 | 1/2004 | Schmelzeisen-Redeker et al. |
| 6,706,000 B2 | 3/2004 | Perez et al. |
| 6,706,049 B2 | 3/2004 | Moerman |
| 6,706,159 B2 | 3/2004 | Moerman et al. |
| 6,740,800 B1 | 5/2004 | Cunningham |
| 6,743,635 B2 | 6/2004 | Neel et al. |
| 6,748,275 B2 | 6/2004 | Lattner et al. |
| 6,753,187 B2 | 6/2004 | Cizdziel et al. |
| 6,766,817 B2 | 7/2004 | da Silva |
| 6,793,633 B2 | 9/2004 | Douglas et al. |
| 6,830,669 B2 | 12/2004 | Miyazaki et al. |
| 6,836,678 B2 | 12/2004 | Tu |
| 6,837,858 B2 | 1/2005 | Cunningham et al. |
| 6,847,451 B2 | 1/2005 | Pugh |
| 6,849,052 B2 | 2/2005 | Uchigaki et al. |
| 6,896,850 B2 | 5/2005 | Subramanian et al. |
| 6,918,404 B2 | 7/2005 | Dias da Silva |
| 6,919,960 B2 | 7/2005 | Hansen et al. |
| 6,923,764 B2 | 8/2005 | Aceti et al. |
| 6,936,476 B1 | 8/2005 | Anderson et al. |
| D511,214 S | 11/2005 | Sasano et al. |
| 6,988,996 B2 | 1/2006 | Roe et al. |
| 7,004,928 B2 * | 2/2006 | Aceti ............... A61B 5/1411 600/575 |
| 7,011,630 B2 | 3/2006 | Desai et al. |
| 7,025,774 B2 | 4/2006 | Freeman et al. |
| D519,868 S | 5/2006 | Sasano et al. |
| 7,052,652 B2 | 5/2006 | Zanzucchi et al. |
| 7,066,586 B2 | 6/2006 | Da Silva |
| 7,066,890 B1 | 6/2006 | Lam et al. |
| 7,141,058 B2 | 11/2006 | Briggs et al. |
| 7,156,809 B2 | 1/2007 | Quy |
| 7,163,616 B2 | 1/2007 | Vreeke et al. |
| 7,192,061 B2 | 3/2007 | Martin |
| D540,343 S | 4/2007 | Cummins |
| 7,223,365 B2 | 5/2007 | Freiherr Von Der Goltz |
| 7,225,008 B1 | 5/2007 | Ward et al. |
| 7,226,461 B2 | 6/2007 | Boecker et al. |
| 7,258,673 B2 | 8/2007 | Racchini et al. |
| D551,243 S | 9/2007 | Young |
| 7,270,970 B2 | 9/2007 | Anderson et al. |
| 7,297,151 B2 | 11/2007 | Boecker et al. |
| 7,299,081 B2 | 11/2007 | Mace et al. |
| 7,343,188 B2 | 3/2008 | Sohrab |
| 7,344,507 B2 | 3/2008 | Briggs et al. |
| 7,379,167 B2 | 5/2008 | Mawhirt et al. |
| 7,427,377 B2 | 9/2008 | Zanzucchi et al. |
| D580,068 S | 11/2008 | Shigesada et al. |
| D580,558 S | 11/2008 | Shigesada et al. |
| D599,373 S | 9/2009 | Kobayashi et al. |
| D601,257 S | 9/2009 | Berlinger |
| 7,585,278 B2 | 9/2009 | Aceti et al. |
| D601,444 S | 10/2009 | Jones et al. |
| D601,578 S | 10/2009 | Poulet et al. |
| 7,682,318 B2 | 3/2010 | Alden et al. |
| D622,393 S | 8/2010 | Gatrall et al. |
| 7,780,631 B2 | 8/2010 | Lum et al. |
| 7,803,123 B2 | 9/2010 | Perez et al. |
| 7,850,621 B2 * | 12/2010 | Briggs ............. A61B 5/150022 600/573 |
| 7,879,058 B2 | 2/2011 | Ikeda |
| 7,887,494 B2 | 2/2011 | Emery et al. |
| D642,191 S | 7/2011 | Barnett et al. |
| 7,988,644 B2 | 8/2011 | Freeman et al. |
| 8,012,103 B2 | 9/2011 | Escutia et al. |
| 8,012,104 B2 | 9/2011 | Escutia et al. |
| 8,105,849 B2 | 1/2012 | McDevitt et al. |
| D654,926 S | 2/2012 | Lipman et al. |
| 8,173,439 B2 | 5/2012 | Petrich et al. |
| 8,184,273 B2 | 5/2012 | Dosmann et al. |
| 8,231,832 B2 | 7/2012 | Zanzucchi et al. |
| 8,251,920 B2 | 8/2012 | Vreeke et al. |
| 8,298,255 B2 | 10/2012 | Conway et al. |
| 8,303,518 B2 | 11/2012 | Aceti et al. |
| 8,360,993 B2 | 1/2013 | Escutia et al. |
| 8,360,994 B2 | 1/2013 | Escutia et al. |
| 8,372,015 B2 | 2/2013 | Escutia et al. |
| 8,376,959 B2 | 2/2013 | Deck |
| 8,382,681 B2 | 2/2013 | Escutia et al. |
| 8,391,940 B2 | 3/2013 | Matzinger et al. |
| D691,174 S | 10/2013 | Lipman et al. |
| 8,574,168 B2 | 11/2013 | Freeman et al. |
| 8,702,624 B2 | 4/2014 | Alden |
| 8,795,201 B2 | 8/2014 | Escutia et al. |
| 8,801,631 B2 | 8/2014 | Escutia et al. |
| 8,919,605 B2 | 12/2014 | Lipman et al. |
| 8,969,097 B2 | 3/2015 | Emery et al. |
| 9,060,723 B2 | 6/2015 | Escutia et al. |
| 9,060,727 B2 | 6/2015 | Saikley et al. |
| 9,095,292 B2 | 8/2015 | Zanzucchi et al. |
| 9,149,215 B2 | 10/2015 | Werner et al. |

(56) References Cited

U.S. PATENT DOCUMENTS

| | | | |
|---|---|---|---|
| 9,366,636 B2 | 6/2016 | Emery et al. |
| 9,380,974 B2 | 7/2016 | Emery et al. |
| 9,603,562 B2 | 3/2017 | Aceti et al. |
| 2001/0001034 A1 | 5/2001 | Douglas |
| 2001/0027277 A1 | 10/2001 | Klitmose |
| 2001/0027328 A1 | 10/2001 | Lum et al. |
| 2001/0053891 A1 | 12/2001 | Ackley |
| 2002/0002326 A1 | 1/2002 | Causey, III et al. |
| 2002/0002344 A1 | 1/2002 | Douglas et al. |
| 2002/0004640 A1 | 1/2002 | Conn et al. |
| 2002/0006355 A1 | 1/2002 | Whitson |
| 2002/0016568 A1 | 2/2002 | Lebel et al. |
| 2002/0020688 A1 | 2/2002 | Sherman et al. |
| 2002/0022934 A1 | 2/2002 | Vogel et al. |
| 2002/0023852 A1 | 2/2002 | Mcivor et al. |
| 2002/0042594 A1 | 4/2002 | Lum et al. |
| 2002/0052618 A1 | 5/2002 | Haar et al. |
| 2002/0087056 A1 | 7/2002 | Aceti et al. |
| 2002/0136667 A1 | 9/2002 | Subramanian et al. |
| 2002/0137998 A1 | 9/2002 | Smart et al. |
| 2002/0160520 A1 | 10/2002 | Orloff et al. |
| 2002/0168290 A1 | 11/2002 | Yuzhakov et al. |
| 2002/0169394 A1 | 11/2002 | Eppstein et al. |
| 2002/0169411 A1 | 11/2002 | Sherman et al. |
| 2002/0177761 A1 | 11/2002 | Orloff et al. |
| 2002/0177764 A1 | 11/2002 | Sohrab |
| 2002/0183102 A1 | 12/2002 | Withers et al. |
| 2002/0188223 A1 | 12/2002 | Perez et al. |
| 2002/0198444 A1 | 12/2002 | Uchigaki et al. |
| 2003/0012693 A1 | 1/2003 | Otillar et al. |
| 2003/0028087 A1 | 2/2003 | Yuzhakov et al. |
| 2003/0028125 A1 | 2/2003 | Yuzhakov et al. |
| 2003/0039587 A1 | 2/2003 | Niermann |
| 2003/0060730 A1 | 3/2003 | Perez |
| 2003/0083685 A1 | 5/2003 | Freeman et al. |
| 2003/0083686 A1 | 5/2003 | Freeman et al. |
| 2003/0105961 A1 | 6/2003 | Zatloukal et al. |
| 2003/0116596 A1 | 6/2003 | Terasawa |
| 2003/0135166 A1 | 7/2003 | Gonnelli |
| 2003/0135333 A1 | 7/2003 | Aceti |
| 2003/0143746 A1 | 7/2003 | Sage |
| 2003/0153844 A1 | 8/2003 | Smith et al. |
| 2003/0153900 A1 | 8/2003 | Aceti et al. |
| 2003/0175987 A1 | 9/2003 | Verdonk et al. |
| 2003/0206302 A1 | 11/2003 | Pugh |
| 2003/0207441 A1 | 11/2003 | Eyster et al. |
| 2003/0208113 A1 | 11/2003 | Mault et al. |
| 2003/0211619 A1 | 11/2003 | Olson et al. |
| 2003/0212344 A1 | 11/2003 | Yuzhakov et al. |
| 2003/0212345 A1 | 11/2003 | McAllister et al. |
| 2003/0212347 A1 | 11/2003 | Sohrab |
| 2003/0216628 A1 | 11/2003 | Bortz et al. |
| 2004/0010207 A1 | 1/2004 | Flaherty et al. |
| 2004/0030353 A1 | 2/2004 | Schmelzeisen-redeker et al. |
| 2004/0039303 A1 | 2/2004 | Wurster et al. |
| 2004/0049219 A1 | 3/2004 | Briggs et al. |
| 2004/0059256 A1 | 3/2004 | Perez |
| 2004/0072357 A1 | 4/2004 | Stiene et al. |
| 2004/0073140 A1 | 4/2004 | Douglas |
| 2004/0092842 A1 | 5/2004 | Boecker et al. |
| 2004/0092995 A1 | 5/2004 | Boecker et al. |
| 2004/0094432 A1 | 5/2004 | Neel et al. |
| 2004/0096959 A1 | 5/2004 | Stiene et al. |
| 2004/0097796 A1 | 5/2004 | Berman et al. |
| 2004/0098009 A1 | 5/2004 | Boecker et al. |
| 2004/0102803 A1 | 5/2004 | Boecker et al. |
| 2004/0122339 A1 | 6/2004 | Roe et al. |
| 2004/0132167 A1 | 7/2004 | Rule et al. |
| 2004/0138588 A1 | 7/2004 | Saikley et al. |
| 2004/0155084 A1 | 8/2004 | Brown |
| 2004/0157339 A1 | 8/2004 | Burke et al. |
| 2004/0178218 A1 | 9/2004 | Schomakers et al. |
| 2004/0186394 A1 | 9/2004 | Roe et al. |
| 2004/0191119 A1 | 9/2004 | Zanzucchi et al. |
| 2004/0202576 A1 | 10/2004 | Aceti et al. |
| 2004/0230216 A1 | 11/2004 | LeVaughn et al. |
| 2004/0232180 A1 | 11/2004 | Badillo |
| 2004/0236251 A1 | 11/2004 | Roe et al. |
| 2004/0238675 A1 | 12/2004 | Banaszkiewicz et al. |
| 2004/0242982 A1 | 12/2004 | Sakata et al. |
| 2004/0249253 A1 | 12/2004 | Racchini et al. |
| 2004/0259180 A1 | 12/2004 | Burke et al. |
| 2005/0004494 A1 | 1/2005 | Perez et al. |
| 2005/0010134 A1 | 1/2005 | Douglas et al. |
| 2005/0015020 A1 | 1/2005 | LeVaughn et al. |
| 2005/0027182 A1 | 2/2005 | Siddiqui et al. |
| 2005/0070819 A1 | 3/2005 | Poux et al. |
| 2005/0096686 A1 | 5/2005 | Allen |
| 2005/0106713 A1 | 5/2005 | Phan et al. |
| 2005/0109386 A1 | 5/2005 | Marshall |
| 2005/0159678 A1 | 7/2005 | Taniike et al. |
| 2005/0187532 A1 | 8/2005 | Thurau et al. |
| 2005/0202567 A1 | 9/2005 | Zanzucchi et al. |
| 2005/0202733 A1 | 9/2005 | Yoshimura et al. |
| 2005/0209518 A1 | 9/2005 | Sage, Jr. et al. |
| 2005/0215872 A1 | 9/2005 | Berner et al. |
| 2005/0215923 A1 | 9/2005 | Wiegel |
| 2005/0234494 A1 | 10/2005 | Conway et al. |
| 2005/0245844 A1 | 11/2005 | Mace et al. |
| 2005/0255001 A1 | 11/2005 | Padmaabhan et al. |
| 2005/0277972 A1 | 12/2005 | Wong et al. |
| 2006/0008389 A1 | 1/2006 | Sacherer et al. |
| 2006/0036134 A1 | 2/2006 | Tarassenko et al. |
| 2006/0052724 A1 | 3/2006 | Roe |
| 2006/0064035 A1 | 3/2006 | Wang et al. |
| 2006/0094985 A1 | 5/2006 | Aceti et al. |
| 2006/0117616 A1 | 6/2006 | Jones et al. |
| 2006/0122536 A1 | 6/2006 | Haar et al. |
| 2006/0135873 A1 | 6/2006 | Karo et al. |
| 2006/0155317 A1 | 7/2006 | List |
| 2006/0161078 A1 | 7/2006 | Schraga |
| 2006/0178600 A1 | 8/2006 | Kennedy et al. |
| 2006/0189908 A1 | 8/2006 | Kennedy |
| 2006/0204399 A1 | 9/2006 | Freeman et al. |
| 2006/0229533 A1 | 10/2006 | Hoenes et al. |
| 2006/0241517 A1 | 10/2006 | Fowler et al. |
| 2006/0257993 A1 | 11/2006 | Mcdevitt et al. |
| 2006/0259102 A1 | 11/2006 | Slatkine |
| 2006/0281187 A1 | 12/2006 | Emery et al. |
| 2007/0016104 A1 | 1/2007 | Jansen et al. |
| 2007/0017824 A1 | 1/2007 | Rippeth et al. |
| 2007/0060842 A1 | 3/2007 | Alvarez-Icaza et al. |
| 2007/0078313 A1 | 4/2007 | Emery et al. |
| 2007/0078358 A1 | 4/2007 | Escutia et al. |
| 2007/0083131 A1 | 4/2007 | Escutia et al. |
| 2007/0112281 A1 | 5/2007 | Olson |
| 2007/0179404 A1 | 8/2007 | Escutia et al. |
| 2007/0179405 A1* | 8/2007 | Emery et al. .............. 600/583 |
| 2007/0255181 A1 | 11/2007 | Alvarez-Icaza et al. |
| 2007/0255302 A1 | 11/2007 | Koeppel et al. |
| 2008/0046831 A1 | 2/2008 | Imai et al. |
| 2008/0077048 A1 | 3/2008 | Escutia et al. |
| 2008/0194934 A1 | 8/2008 | Ray et al. |
| 2008/0269625 A1* | 10/2008 | Halperin et al. .......... 600/508 |
| 2009/0054810 A1 | 2/2009 | Zanzucchi et al. |
| 2009/0156923 A1 | 6/2009 | Power et al. |
| 2009/0292489 A1 | 11/2009 | Burke et al. |
| 2009/0301899 A1 | 12/2009 | Hodges et al. |
| 2010/0010374 A1 | 1/2010 | Escutia et al. |
| 2010/0021947 A1 | 1/2010 | Emery et al. |
| 2010/0021948 A1 | 1/2010 | Lipman et al. |
| 2010/0095229 A1 | 4/2010 | Dixon et al. |
| 2010/0174211 A1* | 7/2010 | Frey et al. .................. 600/583 |
| 2010/0185120 A1 | 7/2010 | Sacherer et al. |
| 2010/0217155 A1 | 8/2010 | Poux et al. |
| 2010/0331650 A1 | 12/2010 | Batman et al. |
| 2011/0098599 A1 | 4/2011 | Emery et al. |
| 2011/0105872 A1 | 5/2011 | Chickering et al. |
| 2011/0201909 A1 | 8/2011 | Emery et al. |
| 2011/0294152 A1 | 12/2011 | Lipman et al. |
| 2012/0166090 A1 | 6/2012 | Lipman et al. |
| 2012/0296179 A1 | 11/2012 | Zanzucchi et al. |
| 2013/0110516 A1 | 5/2013 | Abulhaj et al. |
| 2013/0158430 A1 | 6/2013 | Aceti et al. |

(56) References Cited

U.S. PATENT DOCUMENTS

| | | |
|---|---|---|
| 2013/0158432 A1 | 6/2013 | Escutia et al. |
| 2013/0274568 A1 | 10/2013 | Escutia et al. |
| 2013/0274579 A1 | 10/2013 | Richter et al. |
| 2014/0316301 A1 | 10/2014 | Escutia et al. |
| 2014/0336480 A1 | 11/2014 | Escutia et al. |
| 2014/0376762 A1 | 12/2014 | Lipman et al. |
| 2015/0037898 A1 | 2/2015 | Baldus et al. |
| 2015/0153351 A1 | 6/2015 | Lipman et al. |
| 2015/0212006 A1 | 7/2015 | Emery et al. |
| 2016/0038066 A1 | 2/2016 | Escutia et al. |

FOREIGN PATENT DOCUMENTS

| | | |
|---|---|---|
| DE | 197 05 091 A1 | 2/1999 |
| DE | 199 22 413 A1 | 11/2000 |
| DE | 103 02-501 A1 | 8/2004 |
| EP | 0 103 426 A2 | 3/1984 |
| EP | 0 256 806 A2 | 2/1988 |
| EP | 0 396 016 A2 | 11/1990 |
| EP | 0 396 016 A3 | 11/1990 |
| EP | 0397424 | 11/1990 |
| EP | 0 255 338 A2 | 2/1998 |
| EP | 0 849 584 A2 | 6/1998 |
| EP | 1 266 607 A2 | 12/2002 |
| EP | 1 266 607 A3 | 12/2002 |
| EP | 1 369 688 A2 | 10/2003 |
| EP | 1 369 688 A3 | 10/2003 |
| EP | 1 360 934 A1 | 11/2003 |
| EP | 1 360 934 B1 | 11/2003 |
| EP | 1 486 766 A1 | 12/2004 |
| EP | 1 486 766 B1 | 12/2004 |
| EP | 1 529 489 A1 | 5/2005 |
| EP | 1 529 489 B1 | 5/2005 |
| EP | 1 769 735 A1 | 4/2007 |
| JP | 63-305841 A | 12/1988 |
| JP | 3-63570 A | 3/1991 |
| JP | 03093189 A | 4/1991 |
| JP | 7-67861 A | 3/1995 |
| JP | 7-213925 A | 8/1995 |
| JP | 9-168530 A | 6/1997 |
| JP | 9-313465 A | 9/1997 |
| JP | 9-266889 A | 10/1997 |
| JP | 9-294737 A | 11/1997 |
| JP | 10-024028 A | 1/1998 |
| JP | 10-505258 A | 5/1998 |
| JP | 10508518 A | 8/1998 |
| JP | 10-318970 A | 12/1998 |
| JP | 11056822 A | 3/1999 |
| JP | 11281779 A | 10/1999 |
| JP | 2000-126161 A | 5/2000 |
| JP | 2000-168754 A | 6/2000 |
| JP | 2000-254111 A | 9/2000 |
| JP | 2001-159618 A | 6/2001 |
| JP | 2001-515203 A | 9/2001 |
| JP | 2001-305096 A | 10/2001 |
| JP | 2001-330581 A | 11/2001 |
| JP | 2002-502045 A | 1/2002 |
| JP | 2002-085384 A | 3/2002 |
| JP | 2002-514453 A | 5/2002 |
| JP | 2003-507719 A | 2/2003 |
| JP | 2003-108679 A | 4/2003 |
| JP | 2003-180417 A2 | 7/2003 |
| JP | 2004-000598 A | 1/2004 |
| JP | 2004-500948 A | 1/2004 |
| JP | 2004-117339 A | 4/2004 |
| JP | 2004-202256 A | 7/2004 |
| JP | 2004-209266 A | 7/2004 |
| JP | 2004-519302 A | 7/2004 |
| JP | 2004-522500 A | 7/2004 |
| JP | 2004-528936 A | 9/2004 |
| JP | 2005-503538 A | 2/2005 |
| JP | 2005-087613 A | 4/2005 |
| JP | 2006-512969 A | 4/2005 |
| JP | 3638958 B2 | 4/2005 |
| JP | 2005-525149 A | 8/2005 |
| JP | 2005-237938 A | 9/2005 |
| JP | 2005-525846 A | 9/2005 |
| JP | 2005-527254 A | 9/2005 |
| JP | 2006-506185 A | 2/2006 |
| JP | 2006-512974 A | 4/2006 |
| JP | 2006-516723 A | 7/2006 |
| JP | 2006-521555 A | 9/2006 |
| JP | 2006-527013 A | 11/2006 |
| JP | 2007-014381 A | 1/2007 |
| JP | 2007-054407 A | 3/2007 |
| JP | 2007-136198 A | 6/2007 |
| JP | 2007-521031 A | 8/2007 |
| JP | 2007-537804 A | 12/2007 |
| JP | 2008-125813 A | 6/2008 |
| WO | WO-86/05966 A1 | 10/1986 |
| WO | WO-88/00812 A1 | 2/1988 |
| WO | WO-88/07666 | 10/1988 |
| WO | WO-91/14212 A1 | 9/1991 |
| WO | WO-94/13203 A1 | 6/1994 |
| WO | WO-95/10223 A2 | 4/1995 |
| WO | WO-95/10223 A3 | 4/1995 |
| WO | WO-96/04857 A1 | 2/1996 |
| WO | WO-96/07907 A1 | 3/1996 |
| WO | WO-96/14026 A1 | 5/1996 |
| WO | WO-96/25088 A1 | 8/1996 |
| WO | WO-97/04707 A1 | 2/1997 |
| WO | WO-97/15227 A1 | 5/1997 |
| WO | WO-97/29847 A1 | 8/1997 |
| WO | WO-97/30344 A1 | 8/1997 |
| WO | WO-97/41421 A1 | 11/1997 |
| WO | WO-97/42885 A1 | 11/1997 |
| WO | WO-97/42888 A1 | 11/1997 |
| WO | WO-97/43962 A1 | 11/1997 |
| WO | WO-98/00193 A1 | 1/1998 |
| WO | WO-98/31275 A1 | 7/1998 |
| WO | WO-98/35225 A1 | 8/1998 |
| WO | WO-99/12008 A1 | 3/1999 |
| WO | WO-99/23492 A1 | 5/1999 |
| WO | WO-99/44508 A1 | 9/1999 |
| WO | WO-99/56954 | 11/1999 |
| WO | WO-99/58051 A1 | 11/1999 |
| WO | WO-99/62576 A1 | 12/1999 |
| WO | WO-00/09184 A1 | 2/2000 |
| WO | WO-00/13573 A1 | 3/2000 |
| WO | WO-00/14269 A1 | 3/2000 |
| WO | WO-00/14535 A1 | 3/2000 |
| WO | WO-00/18449 A2 | 4/2000 |
| WO | WO-00/18449 A3 | 4/2000 |
| WO | WO-00/36400 A1 | 6/2000 |
| WO | WO-00/42422 A1 | 7/2000 |
| WO | WO-00/74763 A2 | 12/2000 |
| WO | WO-00/74763 A3 | 12/2000 |
| WO | WO-00/78208 A1 | 12/2000 |
| WO | WO-01/13795 A1 | 3/2001 |
| WO | WO-01/16575 A1 | 3/2001 |
| WO | WO-01/52727 A1 | 7/2001 |
| WO | WO-01/64105 A1 | 9/2001 |
| WO | WO-01/64105 C2 | 9/2001 |
| WO | WO-01/72220 A1 | 10/2001 |
| WO | WO-01/80728 A1 | 11/2001 |
| WO | WO-01/85233 A2 | 11/2001 |
| WO | WO-01/85233 A3 | 11/2001 |
| WO | WO-01/91634 A2 | 12/2001 |
| WO | WO-01/91634 A3 | 12/2001 |
| WO | WO-02/00101 A2 | 1/2002 |
| WO | WO-02/00101 A3 | 1/2002 |
| WO | WO-02/49507 A1 | 6/2002 |
| WO | WO-02/49509 A2 | 6/2002 |
| WO | WO-02/49509 A3 | 6/2002 |
| WO | WO-02/078533 A2 | 10/2002 |
| WO | WO-02/078533 A3 | 10/2002 |
| WO | WO-02/082052 A2 | 10/2002 |
| WO | WO-02/082052 A3 | 10/2002 |
| WO | WO-02/093144 A1 | 11/2002 |
| WO | WO-02/100251 A2 | 12/2002 |
| WO | WO-02/100251 A3 | 12/2002 |
| WO | WO-02/101359 A2 | 12/2002 |
| WO | WO-02/101359 A3 | 12/2002 |
| WO | WO-03/007819 A1 | 1/2003 |

(56) References Cited

FOREIGN PATENT DOCUMENTS

| | | |
|---|---|---|
| WO | WO-03/030984 A1 | 4/2003 |
| WO | WO-03/066128 A2 | 8/2003 |
| WO | WO-03/066128 A3 | 8/2003 |
| WO | WO-03/070099 A1 | 8/2003 |
| WO | WO-03/071940 A1 | 9/2003 |
| WO | WO-03/071940 C1 | 9/2003 |
| WO | WO-2004/045375 A2 | 6/2004 |
| WO | WO-2004/045375 A3 | 6/2004 |
| WO | WO-2004/062499 A1 | 7/2004 |
| WO | WO-2004/062500 A1 | 7/2004 |
| WO | WO-2004/062500 C1 | 7/2004 |
| WO | WO-2004/064636 A1 | 8/2004 |
| WO | WO-2004/085995 A2 | 10/2004 |
| WO | WO-2004/085995 A3 | 10/2004 |
| WO | WO-2004/091693 A2 | 10/2004 |
| WO | WO-2004/091693 A3 | 10/2004 |
| WO | WO-2004/105827 A2 | 12/2004 |
| WO | WO-2004/105827 A3 | 12/2004 |
| WO | WO-2005/006939 A2 | 1/2005 |
| WO | WO-2005/006939 A3 | 1/2005 |
| WO | WO-2005/009238 A1 | 2/2005 |
| WO | WO-2005/013824 A1 | 2/2005 |
| WO | WO-2005/018709 A2 | 3/2005 |
| WO | WO-2005/018709 A3 | 3/2005 |
| WO | WO-2005/018710 A2 | 3/2005 |
| WO | WO-2005/018710 A3 | 3/2005 |
| WO | WO-2005/084543 A1 | 9/2005 |
| WO | WO-2005/084546 A2 | 9/2005 |
| WO | WO-2005/084546 A3 | 9/2005 |
| WO | WO-2005/085995 A1 | 9/2005 |
| WO | WO-2005/112763 A1 | 12/2005 |
| WO | WO-2006/138226 A2 | 12/2006 |
| WO | WO-2006/138226 A3 | 12/2006 |
| WO | WO-2007/041062 A2 | 4/2007 |
| WO | WO-2007/041062 A3 | 4/2007 |
| WO | WO-2007/041063 A2 | 4/2007 |
| WO | WO-2007/041063 A3 | 4/2007 |
| WO | WO-2007/041244 A2 | 4/2007 |
| WO | WO-2007/041244 A3 | 4/2007 |
| WO | WO-2007/041287 A2 | 4/2007 |
| WO | WO-2007/041287 A3 | 4/2007 |
| WO | WO-2007/041355 A2 | 4/2007 |
| WO | WO-2007/041355 A3 | 4/2007 |
| WO | WO-2007/108519 A1 | 9/2007 |
| WO | WO-2007/112034 A2 | 10/2007 |
| WO | WO-2007/112034 A3 | 10/2007 |
| WO | WO-2008/027319 A2 | 3/2008 |
| WO | WO-2008/027319 A3 | 3/2008 |
| WO | WO-2008/062648 A1 | 5/2008 |
| WO | WO-2009/145920 A1 | 12/2009 |
| WO | WO-2009/148624 A1 | 12/2009 |
| WO | WO-2009/148626 A1 | 12/2009 |
| WO | WO-2011/065981 A1 | 6/2011 |
| WO | WO-2011/162823 A1 | 12/2011 |
| WO | WO-2013/020103 A1 | 2/2013 |
| WO | WO-2014/205412 A1 | 12/2014 |

OTHER PUBLICATIONS

ADA (Jan. 1994). "Self-Monitoring of Blood Glucose," Consensus Statement *Diabetes Care* 17(1):81-86.

Anonymous. (Sep. 30, 1993). "The Effect of Intensive Treatment of Diabetes on the Development and Progression of Long-Term Complications in Insulin-Dependent Diabetes Mellitus." *The New England Journal of Medicine* 329(14):977-986.

Anonymous. (Jun. 23, 1998). Taking the "Ouch" Out of Needles: Arrays of "Microneedles" Offer New Techniques for Drug Delivery, *Science Daily*, located at <http:www.sciencedaily.com/releases/1998/06/980623045850.htm>, last visited Jan. 14, 2014, 3 pages.

Beregszàszi, M. et al. (Jul. 1997). "Nocturnal Hypoglycemia in Children and Adolescents with Insulin-Dependent Diabetes Mellitus: Prevalence and Risk Factors," *J. Pediatrics* 131(1 Pt. 1):27-33.

Brazzle, J. et al. Active Microneedles with Integrated Functionality, Solid-State Sensor and Actuator Workshop, Hilton Head Island, South Carolina, Jun. 4-8, 2000, Technical Digest, 199-202.

Chase, H.P. et al. (Feb. 2001). "Continuous Subcutaneous Glucose Monitoring in Children with Type 1 Diabetes," *Pediatrics* 107(2):222-226.

Clarke, W.L. et al. (Sep.-Oct. 1981). "Evaluation of a New Reflectance Photometer for Use in Home Blood Glucose Monitoring," *Diabetes Care*, 4(5):547-550.

Clarke, W.L. et al. (Sep.-Oct. 1987). "Evaluating Clinical Accuracy of Systems for Self-Monitoring of Blood Glucose," *Diabetes Care* 10(5):622-628.

Collison, M.E. et al. (Sep. 1999). "Analytical Characterization of Electrochemical Biosensor Test Strips for Measurement of Glucose in Low-Volume Interstitial Fluid Samples," *Clinical Chemistry* 45(9):1665-1673.

Coster, S. et al. (2000). "Monitoring Blood Glucose Control in Diabetes Mellitus: A Systematic Review." *Health Technology Assessment* 4(12):1-93.

Cox, D.J. et al. (Jun. 1997). "Understanding Error Grid Analysis," *Diabetes Care* 20(6):911-912.

D'Arrigo, T.D. (Mar. 2000). "GlucoWatch Monitor Poised for Approval," *Diabetes Forecast*, 53(3):43-44.

Feldman, B. et al. (2000). "FreeStyle™: A Small-Volume Electrochemical Glucose Sensor for Home Blood Glucose Testing," *Diabetes Technology and Therapeutics*, 2(2):221-229.

INTEG. (2000). "LifeGuide™ Glucose Meter. No Lancets. No Blood," located at <http://www.integonline.com>, last visited May 1, 2000, 10 pages.

Johnson, R.N. et al. (Jan. 1998). "Accuracy of Devices Used for Self-Monitoring of Blood Glucose," *Annals of Clinical Biochemistry* 35(1):68-74.

Johnson, R.N. et al. (Jan. 1999). "Analytical Error of Home Glucose Monitors: A Comparison of 18 Systems," *Annals of Clinical Biochemistry* 36(1):72-79.

Johnson, R.N. et al. (2001). "Error Detection and Measurement in Glucose Monitors," *Clinica Chimica Acta* 307:61-67.

Kumetrix, Inc. (Dec. 1999). "Painless Blood Glucose Monitoring, Courtesy of the Mosquito," *Start-Up* pp. 27-28.

Lee, S-C. (Jun. 1999). "Light Scattering by Closely Spaced Parallel Cylinders Embedded in a Finite Dielectric Slab," *Journal of the Optical Society of America A* 16(6):1350-1361.

McGarraugh, G. et al. (2001). "Physiological Influences on Off-Finger Glucose Testing," *Diabetes Technology & Therapeutics* 3(3):367-376.

McNichols, R.J. et al. (Jan. 2000). "Optical Glucose Sensing in Biological Fluids: An Overview," *Journal of Biomedical Optics*, 5(1):5-16.

Mahler, R.J. et al. (1999). "Clinical Review 102, Type 2 Diabetes Melitus: Update on Diagnosis Pathophysiology, and Treatment," *The Journal of Clinical Endocrinology and Metabolism* 84(4):1165-1171.

Medline Plus. (Jun. 17, 2008). , Medical Encyclopedia, Monitor Blood Glucose-Series: Part 1-4, 6 pages.

Neeley, W.E. et al. (1981). "An Instrument for Digital Matrix Photometry," *Clinical Chemistry* 27(10): 1665-1668.

Neeley, W.E. (1983). "Reflectance Digital Matrix Photometry," *Clinical Chemistry* 29(6):1038-1041.

Neeley, W.E. (1983). "Multilayer Film Analysis for Glucose in 1-μL Samples of Plasma," *Clinical Chemistry* 29(12):2103-2105.

Neeley, W.E. (1988). "A Reflectance Photometer with a Square Photodiode Array Detector for Use on Multilayer Dry-Film Slides," *Clinical Chemistry* 34(11):2367-2370.

Otto, E. et al. (2000). "An Intelligent Diabetes Software Prototype: Predicting Blood Glucose Levels and Recommending Regimen Changes," *Diabetes Technology and Therapeutics* 2(4):569-576.

Pfohl, M. et al. (2000). "Spot Glucose Measurement in Epidermal Interstitial Fluid—An Alternative to Capillary Blood Glucose Estimation," *Experimental and Clinical Endocrinology & Diabetes* 108(1):1-4.

Princen, H.M. (May 1969). "Capillary Phenomena in Assemblies of Parallel Cylinders, I. Capillary Rise Between Two Cylinders," *Journal of Colloid and Interface Science* 30(1):69-75.

(56) References Cited

OTHER PUBLICATIONS

Princen, H.M. (Jul. 1969). "Capillary Phenomena in Assemblies of Parallel Cylinders, II. Capillary Rise in Systems with More Than Two Cylinders," *Journal of Colloid and Interface Science* 30(3):359-371.

Rebrin, K. et al. (Sep. 1999). "Subcutaneous Glucose Predicts Plasma Glucose Independent of Insulin: Implications for Continuous Monitoring," *American Journal of Physiology* 277(3):E561-E571.

Rosen, S. (1999). "Road to New-Age Glucose Monitoring Still Rocky," *Diagnostic Insight*, pp. 4-5, 12-13, 16.

Smart, W.H. et al. (2000). "The Use of Silicon Microfabrication Technology in Painless Glucose Monitoring," *Diabetes Technology & Therapeutics* 2(4):549-559.

Spielman, A. et al. (2001). *Mosquito: A Natural History of Our Most Persistent and Deadly Foe*, First Edition, Hyperion, New York, NY, 3 pages. (Table of Contents Only).

Sonntag, O. (1993). Ektachem. Dry Chemistry, Analysis With Carrier-Bound Reagents, Elsevier Science Publishers, 57 pages.

Svedman, C. et al. (Apr. 1999). "Skin Mini-Erosion Technique for Monitoring Metabolites in Interstitial Fluid: Its Feasibility Demonstrated by OGTT Results in Diabetic and Non-Diabetic Subjects," *Scand. J. Clin. Lab. Invest.* 59(2):115-123.

Tietz, N.W. (1986). Textbook of Clinical Chemistry, W.B. Saunders Company, pp. 1533 and 1556.

Trinder, P. (1969). "Determination of Glucose in Blood Using Glucose Oxidase with an Alternate Oxygen Acceptor," *Annals of Clinical Biochemistry* 6:24-28.

Yum, S. I. et al. (Nov. 1, 1999). "Capillary Blood Sampling for Self-Monitoring of Blood Glucose," *Diabetes Technology & Therapeutics*, 1(1):29-37.

Advisory Action dated Feb. 2, 2009, for U.S. appl. No. 11/529,613, filed Sep. 29, 2006, 3 pages.

Advisory Action dated Apr. 8, 2010, for U.S. Appl. No. 11/529,613, filed Sep. 29, 2006, 3 pages.

Canadian Examination Report dated Mar. 4, 2011, for Canadian Patent Application No. 2,519,628, filed on Mar. 24, 2004, 3 pages.

European Office Action dated Jan. 7, 2014 for EP Patent Application No. 12192620.8, filed on Nov. 14, 2012, 6 pages.

Extended European Search Report dated Apr. 19, 2011, for EP Application No. 10 18 0848.3 filed Sep. 28, 2010, 5 pages.

Extended European Search Report dated Feb. 22, 2012, for EP Application No. EP 10 18 1155.2, filed Sep. 28, 2010, six pages.

Extended European Search Report dated Jan. 22, 2013, for EP Application No. 12182900.6, filed on Sep. 29, 2006, 6 pages.

Extended European Search Report dated Apr. 29, 2013 for EP Patent Application No. 12192620.8, filed on Nov. 14, 2012, 8 pages.

Final Office Action dated Jul. 9, 2008, for U.S. Appl. No. 11/529,613, filed Sep. 29, 2006, 19 pages.

Final Office Action dated Nov. 23, 2009, for U.S. Appl. No. 11/529,613, filed Sep. 29, 2006, 20 pages.

Final Office Action dated Jan. 21, 2011, for U.S. Appl. No. 11/529,613, filed Sep. 29, 2006, 7 pages.

Final Office Action dated Aug. 15, 2013 for U.S. Appl. No. 13/562,129, filed Jul. 30, 2012, 12 pages.

International Search Report dated Dec. 3, 2004, for PCT Application No. PCT/US2004/08798, filed on Mar. 24, 2004, 3 pages.

International Search Report dated May 2, 2007, for PCT Application No. PCT/US2006/37923, filed on Sep. 9, 2006, 1 page.

International Search Report dated Aug. 16, 2007 for PCT Application No. PCT/US2006/038163, filed on Sep. 29, 2006, 1 page.

International Search Report dated Aug. 7, 2007 for PCT/US2006/38049, filed on Sep. 29, 2006, 1 page.

International Search Report dated Oct. 19, 2012 for PCT Application No. PCT/US2012/049629, filed on Aug. 3, 2012, 4 pages.

Interview Summary dated Jan. 13, 2009, for U.S. Appl. No. 11/529,613, filed Sep. 29, 2006, 4 pages.

Interview Summary dated Nov. 1, 2010, for U.S. Appl. No. 11/529,613, filed Sep. 29, 2006, 3 pages.

Interview Summary dated May 17, 2012, for U.S. Appl. No. 13/197,592, filed Aug. 3, 2011, 3 pages.

Interview Summary dated May 17, 2012, for U.S. Appl. No. 13/197,603, filed Aug. 3, 2011, 3 pages.

Interview Summary dated Aug. 27, 2012, for U.S. Appl. No. 13/197,592, filed Aug. 3, 2011, 3 pages.

Interview Summary dated Aug. 27, 2012, for U.S. Appl. No. 13/197,603, filed Aug. 3, 2011, 3 pages.

Non-Final Office Action dated Dec. 12, 2007, for U.S. Appl. No. 11/529,613, filed Sep. 29, 2006, 13 pages.

Non-Final Office Action dated Apr. 28, 2009, for U.S. Appl. No. 11/529,613, filed Sep. 29, 2006, 21 pages.

Non-Final Office Action dated Jun. 4, 2010, for U.S. Appl. No. 11/529,613, filed Sep. 29, 2006, 23 pages.

Non-Final Office Action dated Mar. 23, 2012, for U.S. Appl. No. 13/197,592, filed Aug. 3, 2011, 7 pages.

Non-Final Office Action dated Mar. 23, 2012, for U.S. Appl. No. 13/197,603, filed Aug. 3, 2011, 6 pages.

Non-Final Office Action dated Nov. 26, 2012 for U.S. Appl. No. 13/562,129, filed Jul. 30, 2012, 9 pages.

Notice of Allowance dated May 3, 2011, for U.S. Appl. No. 11/529,613, filed Sep. 29, 2006, 12 pages.

Request for Continued Examination filed on Feb. 4, 2009, for U.S. Appl. No. 11/529,613, filed Sep. 29, 2006, 2 pages.

Request for Continued Examination filed on Apr. 23, 2010, for U.S. Appl. No. 11/529,613, filed Sep. 29, 2006, 2 pages.

Response to Non-Final Office Action filed on Apr. 11, 2008, for U.S. Appl. No. 11/529,613, filed Sep. 29, 2006, 18 pages.

Response to Non-Final Office Action filed on Jul. 28, 2009, for U.S. Appl. No. 11/529,613, filed Sep. 29, 2006, 27 pages.

Response to Non-Final Office Action filed on Nov. 4, 2010 for U.S. Appl. No. 11/529,613, filed Sep. 29, 2006, 18 pages.

Response to Non-Final Office Action filed on Aug. 23, 2012 for U.S. Appl. No. 13/197,592, filed Aug. 3, 2011, 7 pages.

Response to Non-Final Office Action filed on Aug. 23, 2012 for U.S. Appl. No. 13/197,603, filed Aug. 3, 2011, 7 pages.

Response to Final Office Action filed on Jan. 9, 2009, for U.S. Appl. No. 11/529,613, filed Sep. 29, 2006, 23 pages.

Response to Final Office Action filed on Mar. 23, 2010, for U.S. Appl. No. 11/529,613, filed Sep. 29, 2006, 25 pages.

Response to Final Office Action filed on Apr. 12, 2011, for U.S. Appl. No. 11/529,613, filed Sep. 29, 2006, 11 pages.

Written Opinion dated Dec. 3, 2004, for PCT Application No. PCT/US2004/08798, filed on Mar. 24, 2004, 4 pages.

Written Opinion dated May 2, 2007, for PCT Application No. PCT/US2006/37923, filed on Sep. 9, 2006, 5 pages.

Written Opinion dated Aug. 7, 2007 for PCT/US2006/38049, filed on Sep. 29, 2006, 6 pages.

Written Opinion dated Aug. 16, 2007 for PCT Application No. PCT/US2006/038163, filed on Sep. 29, 2006, 4 pages.

Written Opinion dated Oct. 19, 2012 for PCT Application No. PCT/US2012/049629, filed on Aug. 3, 2012, 7 pages.

Burge, M.R., (Aug. 2001). "Lack of Compliance with Home Blood Glucose Monitoring Predicts Hospitalization in Diabetes", *Diabetes Care* 24(8): 1502-1503.

European Office Action dated Oct. 26, 2015, for EP Patent Application 12820723.0, filed on Aug. 3, 2012. 4 pages.

Final Office Action dated Apr. 13, 2016, for U.S. Appl. No. 13/669,366, filed Nov. 5, 2012, 31 pages.

Final Office Action dated Aug. 15, 2013, for U.S. Appl. No. 13/562,129, filed Jul. 30, 2012, 12 pages.

Final Office Action dated Aug. 28, 2014, for U.S. Appl. No. 13/562,129, filed Jul. 30, 2012, 11 pages.

Final Office Action dated Dec. 26, 2014, for U.S. Appl. No. 13/669,366, filed Nov. 5, 2012, 9 pages.

Final Office Action dated Jan. 22, 2014, for U.S. Appl. No. 13/669,366, filed Nov. 5, 2012, 8 pages.

Final Office Action dated Jun. 30, 2010, for U.S. Appl. No. 11/529,612, filed Sep. 29, 2006, 11 pages.

Final Office Action dated May 30, 2007, for U.S. Appl. No. 11/125,107, filed May 10, 2005, 11 pages.

Final Office Action dated Nov. 1, 2010, for U.S. Appl. No. 11/311,667, filed Dec. 20, 2005, 9 pages.

(56) References Cited

OTHER PUBLICATIONS

Final Office Action dated Nov. 21, 2011, for U.S. Appl. No. 11/311,667, filed Dec. 20, 2005, 8 pages.
Final Office Action dated Jun. 11, 2010, for U.S. Appl. No. 11/529,614, filed Sep. 29, 2006, 16 pages.
Final Office Action dated Mar. 10, 2015, for U.S. Appl. No. 11/529,614, filed Sep. 29, 2006, 24 pages.
Hemmerich, K.J. et al. (Apr. 1995)."Guide to Engineering Thermoplastics," Medical Devices and Diagnostic Industry pp. 39-59.
Ishii H. et al., (Aug. 2001). "Seasonal Variation of Glycemic Control in Type 2 Diabetic Patients", *Diabetes Care* 24(8): 1503.
Massey V. et al. (Aug. 1960). "Studies on the Reaction Mechanism of Lipoyl Dehydrogenase" *Biochim. Biophys.* Acta 48: 33-47.
Non Final Office Action dated Apr. 12, 2011, for U.S. Appl. No. 11/311,667, filed Dec. 20, 2005, 7 pages.
Non Final Office Action dated Aug. 5, 2014, for U.S. Appl. No. 13/669,366, filed Nov. 5, 2012, 8 pages.
Non Final Office Action dated Dec. 5, 2014, for U.S. Appl. No. 13/562,129, filed Jul. 30, 2012, 7 pages.
Non Final Office Action dated Jan. 12, 2009, for U.S. Appl. No. 11/529,612, filed Sep. 29, 2006, 9 pages.
Non Final Office Action dated Jan. 21, 2011, for U.S. Appl. No. 11/529,612, filed Sep. 29, 2006, 9 pages.
Non Final Office Action dated Jul. 13, 2010, for U.S. Appl. No. 12/222,724, filed Aug. 14, 2008, 11 pages.
Non Final Office Action dated Jul. 31, 2015, for U.S. Appl. No. 13/669,366, filed Nov. 5, 2012, 16 pages.
Non Final Office Action dated Mar. 21, 2014, for U.S. Appl. No. 13/562,129, filed Jul. 30, 2012, 12 pages.
Non Final Office Action dated Mar. 25, 2011, for U.S. Appl. No. 12/222,724, filed Aug. 14, 2008, 13 pages.
Non Final Office Action dated Mar. 5, 2010, for U.S. Appl. No. 11/311,667, filed Dec. 20, 2005, 8 pages.
Non Final Office Action dated May 14, 2008, for U.S. Appl. No. 11/529,612, filed Sep. 29, 2006, 9 pages.
Non Final Office Action dated May 16, 2013, for U.S. Appl. No. 13/669,366, filed Nov. 5, 2012, 8 pages.
Non Final Office Action dated May 5, 2005, for U.S. Appl. No. 10/131,268, filed Apr. 23, 2002, 8 pages.
Non Final Office Action dated Nov. 2, 2006, for U.S. Appl. No. 11/125,107, filed May 10, 2005, 10 pages.
Non Final Office Action dated Nov. 26, 2012, for U.S. Appl. No. 13/562,129, filed Jul. 30, 2012, 9 pages.
Non Final Office Action dated Oct. 14, 2009, for U.S. Appl. No. 11/529,612, filed Sep. 29, 2006, 10 pages.
Non Final Office Action dated Oct. 3, 2008, for U.S. Appl. No. 10/722,074, filed Nov. 24, 2003, 10 pages.
Non-Final Office Action dated Dec. 17, 2015, for U.S. Appl. No. 11/529,614, filed Sep. 29, 2006, 6 pages.
Non Final Office Action dated Dec. 2, 2004, for U.S. Appl. No. 10/347,620, filed Jan. 22, 2003, 8 pages.
Non-Final Office Action dated Jan. 27, 2009, for U.S. Appl. No. 11/529,614, filed Sep. 29, 2006, 17 pages.
Non-Final Office Action dated Jan. 6, 2014, for U.S. Appl. No. 11/529,614, filed Sep. 29, 2006, 12 pages.
Non-Final Office Action dated Jun. 21, 2013, for U.S. Appl. No. 13/752,261, filed Jan. 28, 2013, 12 pages.
Non-Final Office Action dated Jun. 6, 2008, for U.S. Appl. No. 11/529,614, filed Sep. 29, 2006, 17 pages.
Non-Final Office Action dated Oct. 9, 2014, for U.S. Appl. No. 14/446,262, filed Jul. 29, 2014, 15 pages.
Non Final Office Action dated Sep. 29, 2004, for U.S. Appl. No. 10/394,230, filed Mar. 24, 2003, 10 pages.
Notice of Allowance dated Apr. 18, 2012, for U.S. Appl. No. 11/529,612, filed Sep. 29, 2006, 8 pages.
Notice of Allowance dated Apr. 19, 2010, for U.S. Appl. No. 29/338,117, filed Jun. 4, 2009, 4 pages.
Notice of Allowance dated Aug. 3, 2012, for U.S. Appl. No. 11/529,612, filed Sep. 29, 2006, 5 pages.
Notice of Allowance dated Jan. 14, 2010, for U.S. Appl. No. 29/338,117, filed Jun. 4, 2009, 4 pages.
Notice of Allowance dated Jun. 29, 2012, for U.S. Appl. No. 11/311,667, filed Dec. 20, 2005, 5 pages.
Notice of Allowance dated Mar. 14, 2012, for U.S. Appl. No. 12/222,724, filed Aug. 14, 2008, 7 pages.
Notice of Allowance dated Mar. 27, 2015, for U.S. Appl. No. 13/562,129, filed Jul. 30, 2012, 7 pages.
Notice of Allowance dated Mar. 31, 2005, for U.S. Appl. No. 10/394,230, filed Mar. 24, 2003, 10 pages.
Notice of Allowance dated May 15, 2008, for U.S. Appl. No. 11/125,107, filed May 10, 2005, 7 pages.
Notice of Allowance dated May 18, 2009, for U.S. Appl. No. 29/300,934, filed May 30, 2008, 4 pages.
Notice of Allowance dated May 28, 2009, for U.S. Appl. No. 29/300,933, filed May 30, 2008, 6 pages.
Notice of Allowance dated Nov. 23, 2011, for U.S. Appl. No. 12/222,724, filed Aug. 14, 2008, 7 pages.
Notice of Allowance dated Nov. 27, 2012, for U.S. Appl. No. 11/529,612, filed Sep. 29, 2006, 5 pages.
Notice of Allowance dated Nov. 29, 2005, for U.S. Appl. No. 10/131,268, filed Apr. 23, 2002, 6 pages.
Notice of Allowance dated Oct. 12, 2011, for U.S. Appl. No. 11/529,612, filed Sep. 29, 2006, 8 pages.
Notice of Allowance dated Feb. 23, 2015, for U.S. Appl. No. 14/446,262, filed Jul. 29, 2014, 8 pages.
Notice of Allowance dated Feb. 5, 2014, for U.S. Appl. No. 13/752,261, filed Jan. 28, 2013, 9 pages.
Notice of Allowance dated Jun. 15, 2009, for U.S. Appl. No. 10/722,074, filed Nov. 24, 2003, 6 pages.
Notice of Allowance dated Mar. 2, 2016, for U.S. Appl. No. 11/529,614, filed Sep. 29, 2006, 12 pages.
Notice of Allowance dated Mar. 28, 2005, for U.S. Appl. No. 10/347,620, filed Jan. 22, 2003, 6 pages.
Response After Final filed Oct. 28, 2014, for U.S. Appl. No. 13/562,129, filed Jul. 30, 2012, 13 pages.
Response to Final Office Action filed Apr. 22, 2014, for U.S. Appl. No. 13/669,366, filed Nov. 5, 2012, 9 pages.
Response to Final Office Action filed Apr. 23, 2012, for U.S. Appl. No. 11/311,667, filed Dec. 20, 2005, 13 pages.
Response to Final Office Action filed Mar. 1, 2011, for U.S. Appl. No. 11/311,667, filed Dec. 20, 2005, 13 pages.
Response to Final Office Action filed May 26, 2015, for U.S. Appl. No. 13/669,366, filed Nov. 5, 2012, 11 pages.
Response to Final Office Action filed Nov. 1, 2010, for U.S. Appl. No. 11/529,612, filed Sep. 29, 2006, 20 pages.
Response to Final Office Action filed on Aug. 10, 2015, for U.S. Appl. No. 11/529,614, filed Sep. 29, 2006, 8 pages.
Response to Final Office Action filed on Nov. 12, 2010, for U.S. Appl. No. 11/529,614, filed Sep. 29, 2006, 9 pages.
Response to Final Office Action filed Sep. 21, 2007, for U.S. Appl. No. 11/125,107, filed May 10, 2005, 11 pages.
Response to Non Final Office Action filed Sep. 8, 2005, for U.S. Appl. No. 10/131,268, filed Apr. 23, 2002, 11 pages.
Response to Non Final Office Action filed Apr. 14, 2010, for U.S. Appl. No. 11/529,612, filed Sep. 29, 2006, 9 pages.
Response to Non Final Office Action filed Aug. 25, 2011, for U.S. Appl. No. 12/222,724, filed Aug. 14, 2008, 9 pages.
Response to Non Final Office Action filed Dec. 31, 2015, for U.S. Appl. No. 13/669,366, filed Nov. 5, 2012, 13 pages.
Response to Non Final Office Action filed Feb. 28, 2005, for U.S. Appl. No. 10/394,230, filed Mar. 24, 2003, 11 pages.
Response to Non Final Office Action filed Feb. 28, 2007, for U.S. Appl. No. 11/125,107, filed May 10, 2005, 22 pages.
Response to Non Final Office Action filed Jan. 13, 2011, for U.S. Appl. No. 12/222,724, filed Aug. 14, 2008, 17 pages.
Response to Non Final Office Action filed Jul. 21, 2011, for U.S. Appl. No. 11/529,612, filed Sep. 29, 2006, 9 pages.
Response to Non Final Office Action filed Jun. 12, 2009, for U.S. Appl. No. 11/529,612, filed Sep. 29, 2006, 14 pages.
Response to Non Final Office Action filed Jun. 23, 2014, for U.S. Appl. No. 13/562,129, filed Jul. 30, 2012, 14 pages.

(56) References Cited

OTHER PUBLICATIONS

Response to Non Final Office Action filed Mar. 5, 2015, for U.S. Appl. No. 13/562,129, filed Jul. 30, 2012, 9 pages.
Response to Non Final Office Action filed May 28, 2013, for U.S. Appl. No. 13/562,129, filed Jul. 30, 2012, 8 pages.
Response to Non Final Office Action filed Nov. 18, 2013, for U.S. Appl. No. 13/669,366, filed Nov. 5, 2012, 7 pages.
Response to Non Final Office Action filed Nov. 5, 2014, for U.S. Appl. No. 13/669,366, filed Nov. 5, 2012, 13 pages.
Response to Non-Final Office Action filed on Apr. 3, 2014, for U.S. Appl. No. 11/529,614, filed Sep. 29, 2006, 13 pages.
Response to Non-Final Office Action filed on Aug. 18, 2014, for U.S. Appl. No. 11/529,614, filed Sep. 29, 2006, 4 pages.
Response to Non-Final Office Action filed on Dec. 23, 2013, for U.S. Appl. No. 13/752,261, filed Jan. 28, 2013, 8 pages.
Response to Non Final Office Action filed on Feb. 16, 2005 for U.S. Appl. No. 10/347,620, filed Jan. 22, 2003, 24 pages.
Response to Non-Final Office Action filed on Feb. 16, 2016, for U.S. Appl. No. 11/529,614, filed Sep. 29, 2006, 6 pages.
Response to Non Final Office Action filed on Feb. 3, 2009, for U.S. Appl. No. 10/722,074, filed Nov. 24, 2003, 11 pages.
Response to Non-Final Office Action filed on Jan. 9, 2015, for U.S. Appl. No. 14/446,262, filed Jul. 29, 2014, 13 pages.
Response to Non-Final Office Action filed on Jul. 23, 2009, for U.S. Appl. No. 11/529,614, filed Sep. 29, 2006, 14 pages.
Response to Non-Final Office Action filed on Oct. 6, 2008, for U.S. Appl. No. 11/529,614, filed Sep. 29, 2006, 7 pages.
Response to Non Final Office Action filed Sep. 12, 2011, for U.S. Appl. No. 11/311,667, filed Dec. 20, 2005, 9 pages.
Response to Non Final Office Action filed Sep. 15, 2008, for U.S. Appl. No. 11/529,612, filed Sep. 29, 2006, 12 pages.
Response to Non Final Office Action filed Sep. 2, 2010, for U.S. Appl. No. 11/311,667, filed Dec. 20, 2005, 14 pages.
Straub F.B. (Mar. 1939). "Isolation and Properties of a flavoprotien from Heart Muscle Tissue", *Biochemical Journal* 33: 787-792.
Supplemental Response filed on Jun. 12, 2012, for U.S. Appl. No. 11/311,667, filed Dec. 20, 2005, 6 pages.
Supplemental Response filed on Sep. 8, 2010, for U.S. Appl. No. 11/311,667, filed Dec. 20, 2005, 6 pages.
Supplemental Response filed on May 26, 2009, for U.S. Appl. No. 10/722,074, filed Nov. 24, 2003, 11 pages.
U.S. Precision Lens, Inc. (1983).The Handbook of Plastic Optics.
Extended European Search Report dated Nov. 8, 2016 from the European Patent Office for Application No. 16167087.2, filed Aug. 3, 2012, 6 pages.
Non-Final Office Action dated Mar. 20, 2017, by the United States Patent and Trademark Office for U.S. Appl. No. 15/191,434, filed Jun. 23, 2016, 20 pages.

* cited by examiner

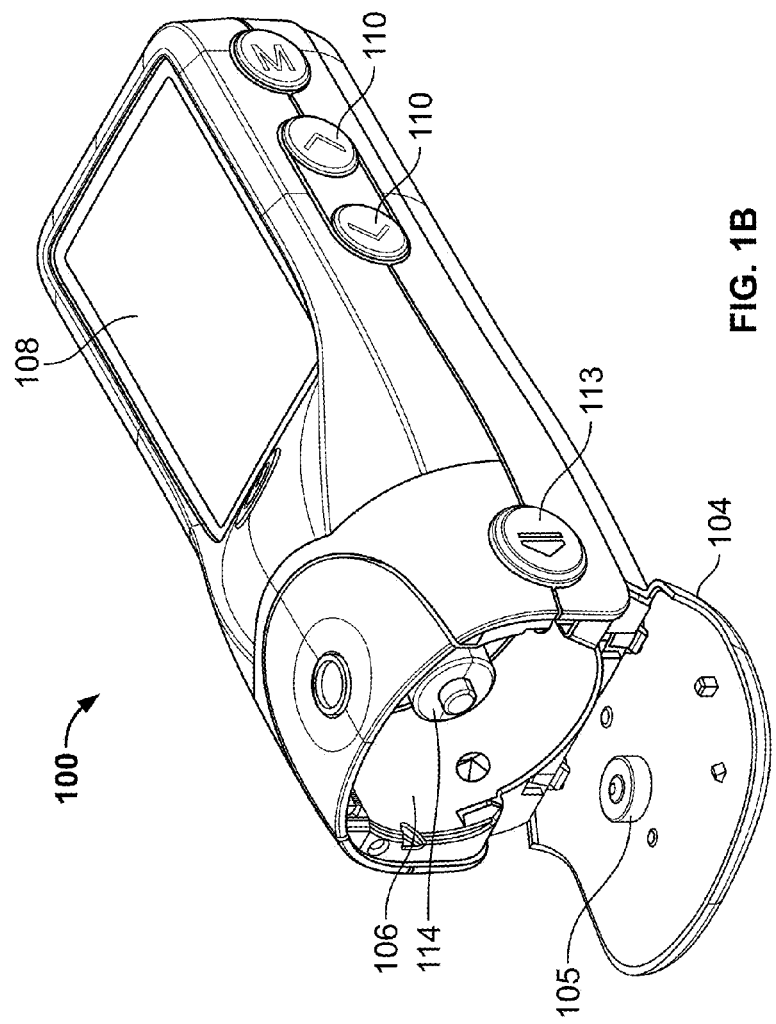
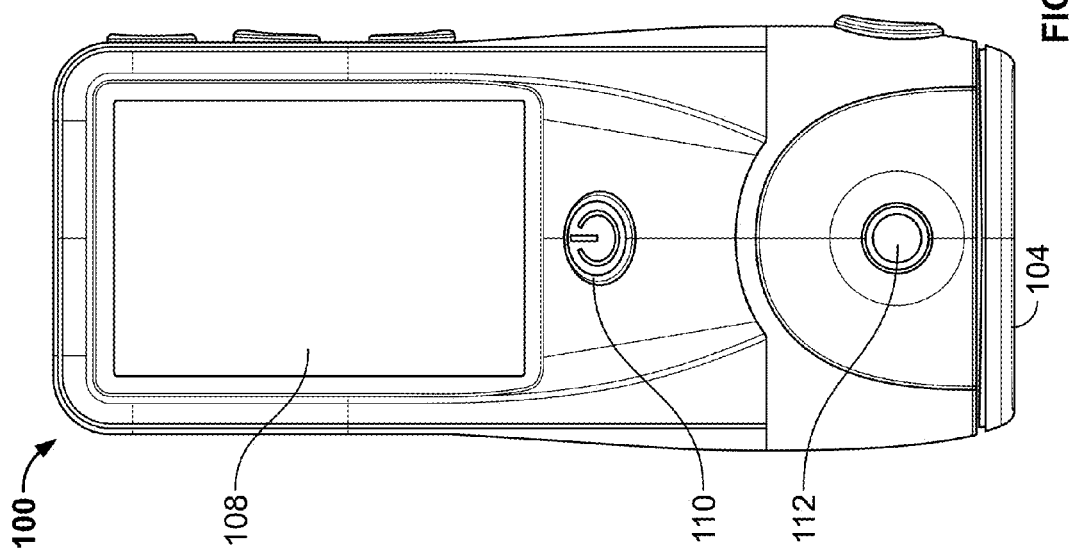
FIG. 1B
FIG. 1A

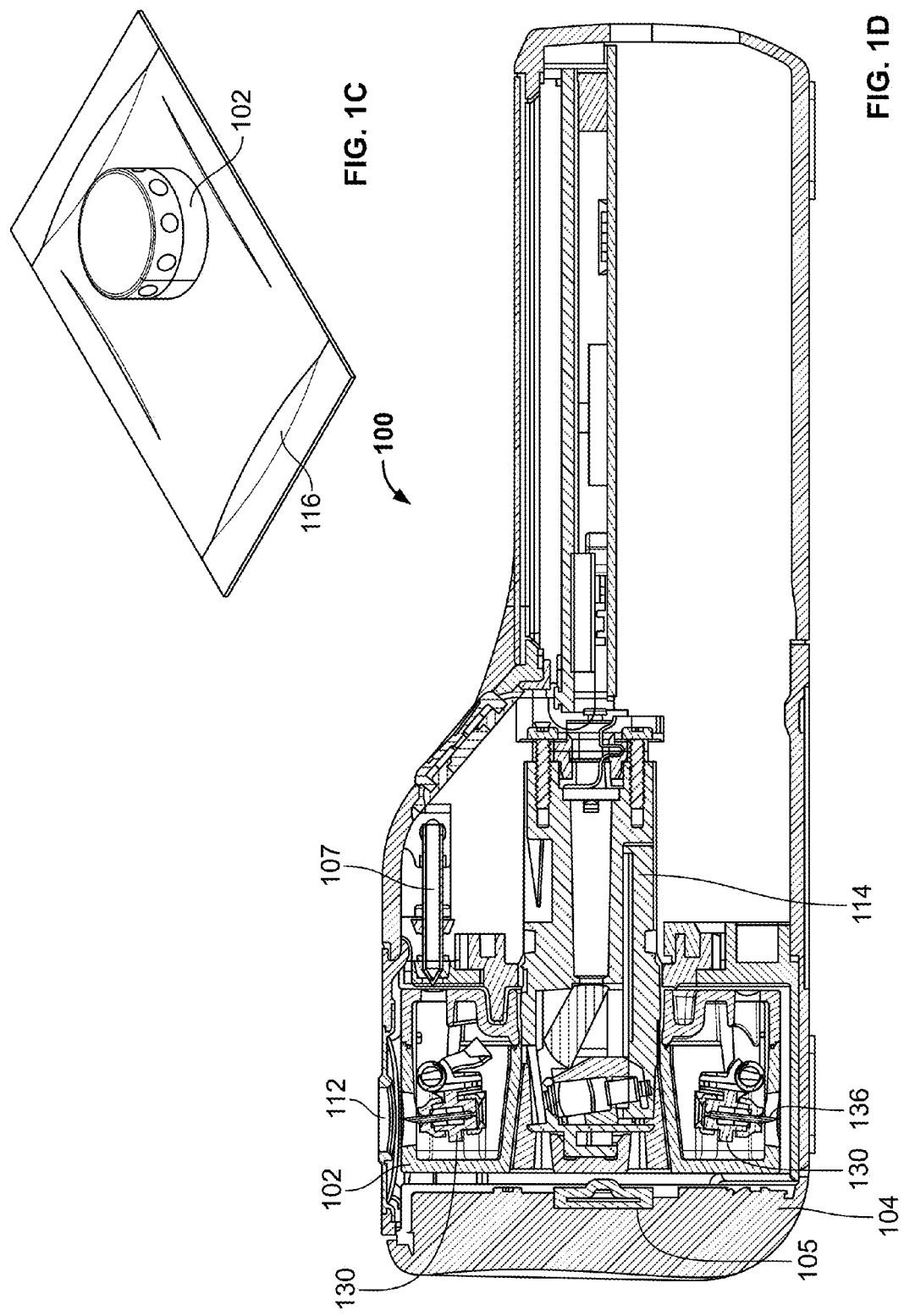

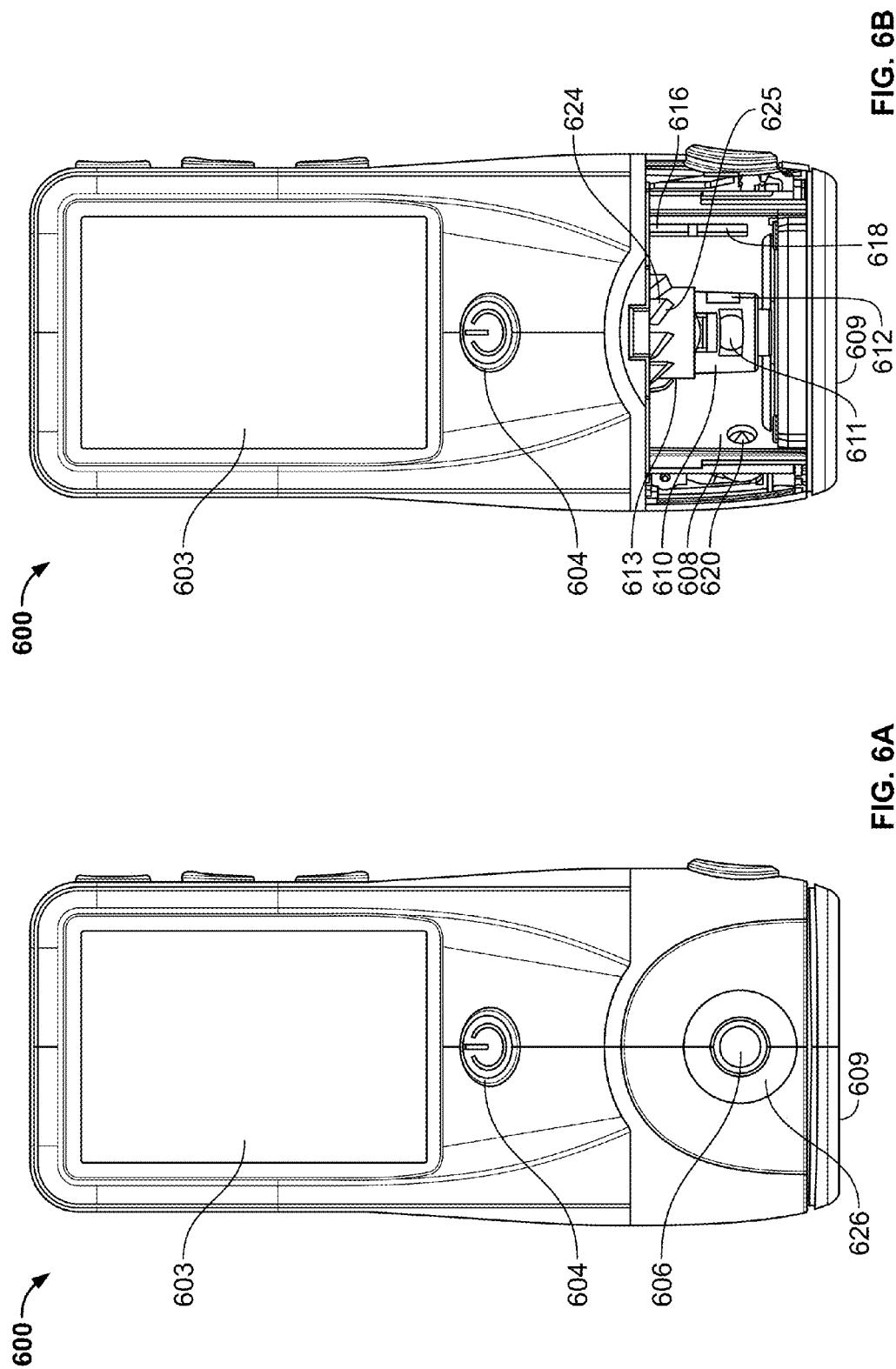

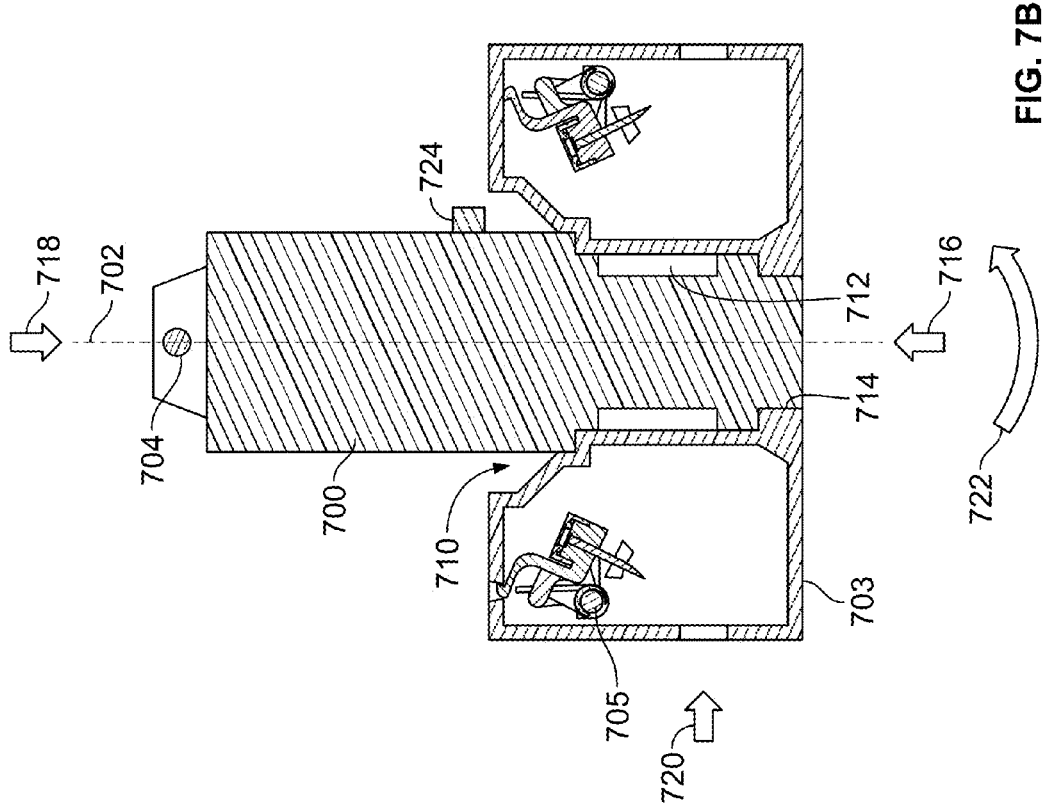
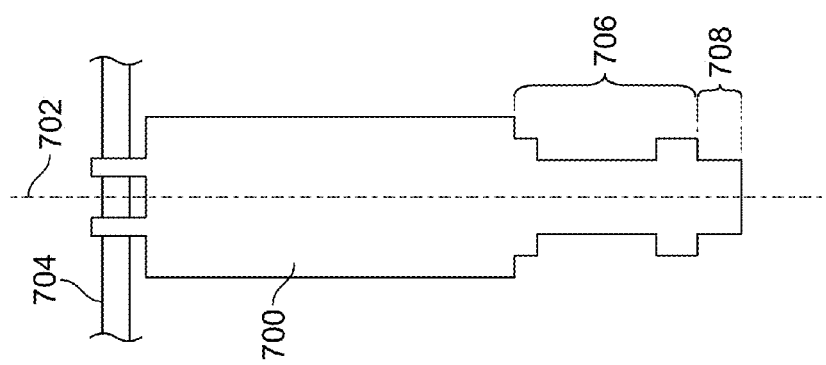
FIG. 7B
FIG. 7A

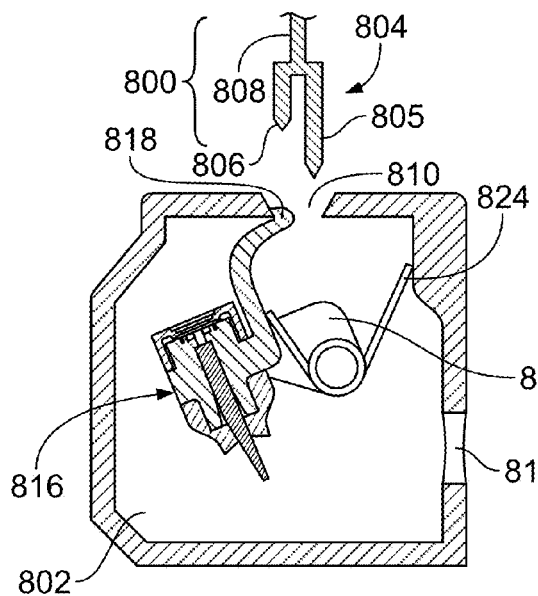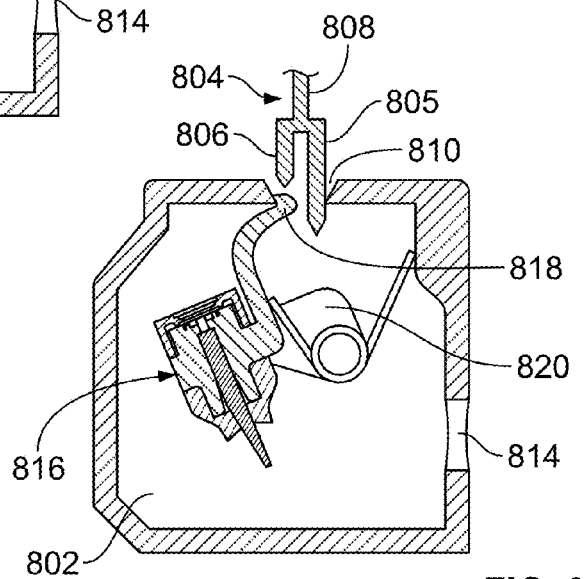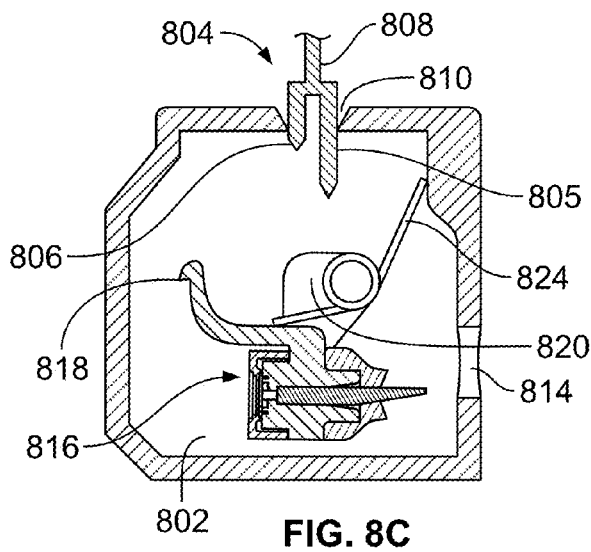

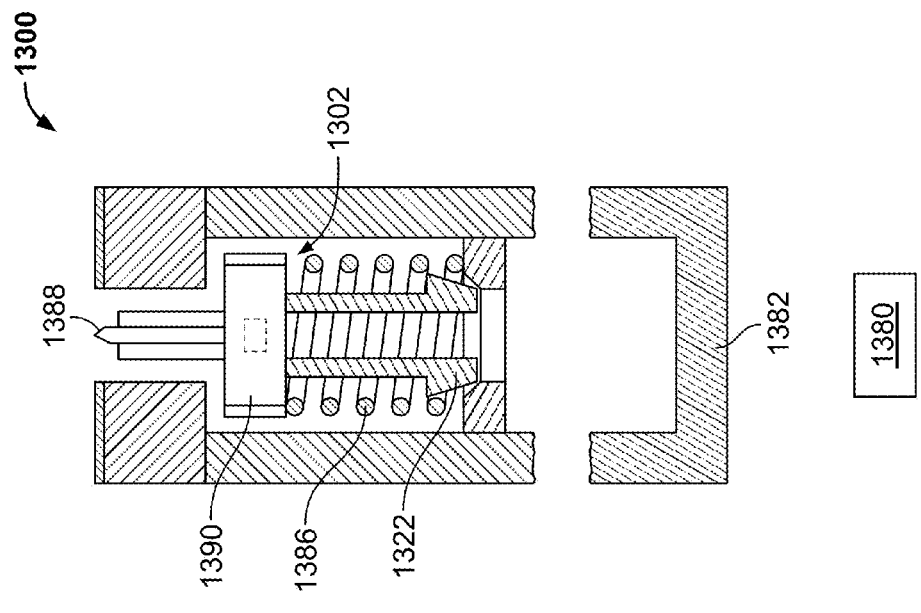
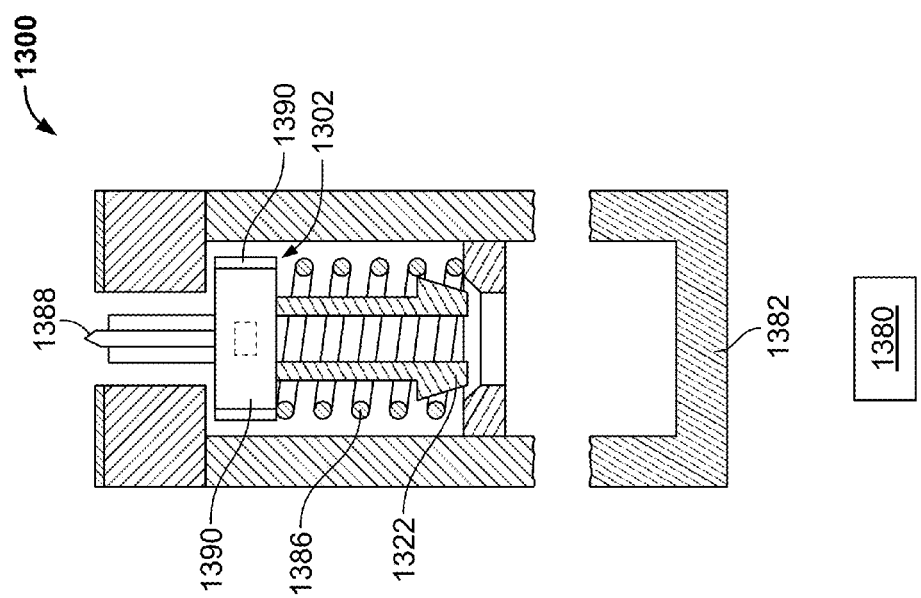
FIG. 13B
FIG. 13C

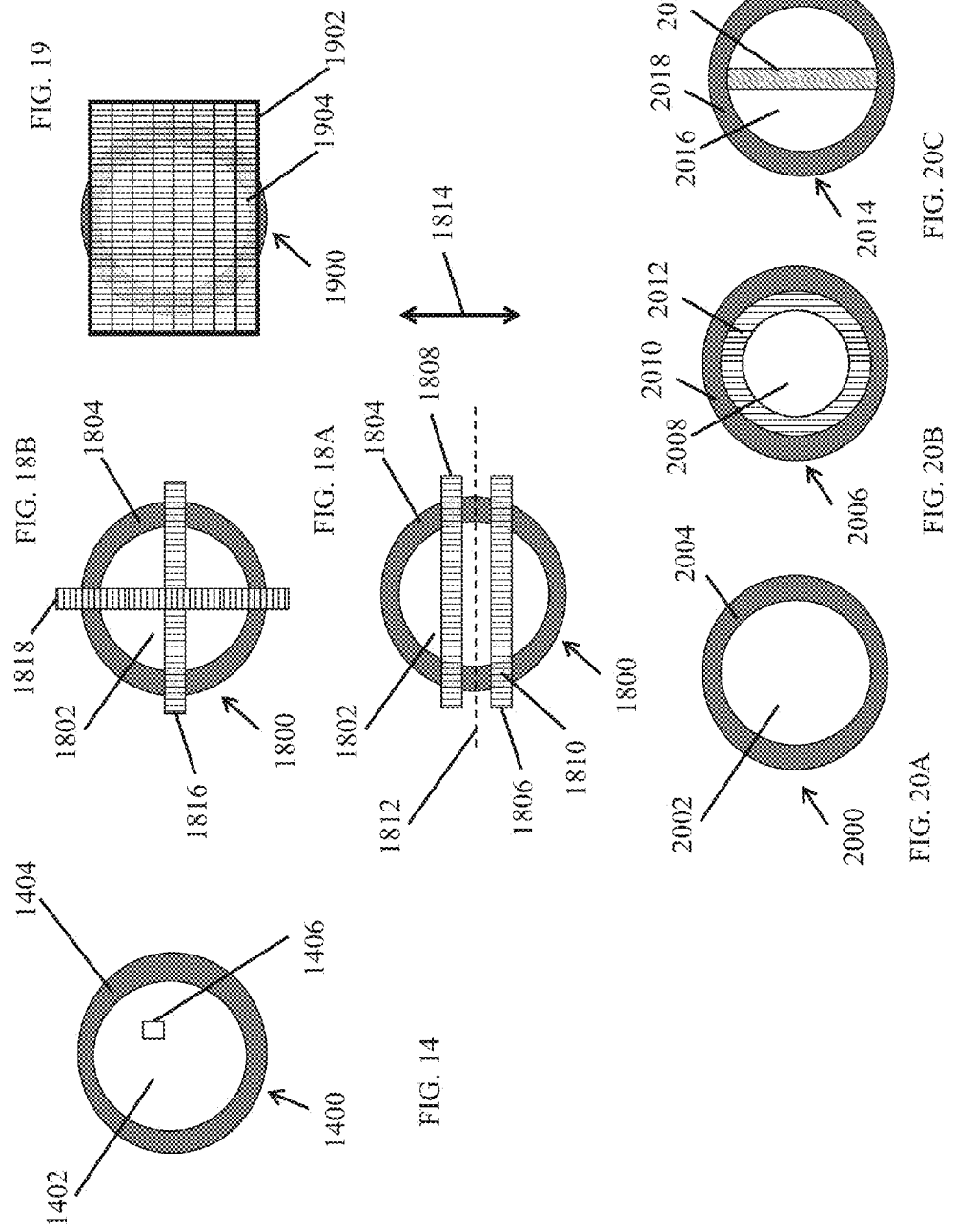

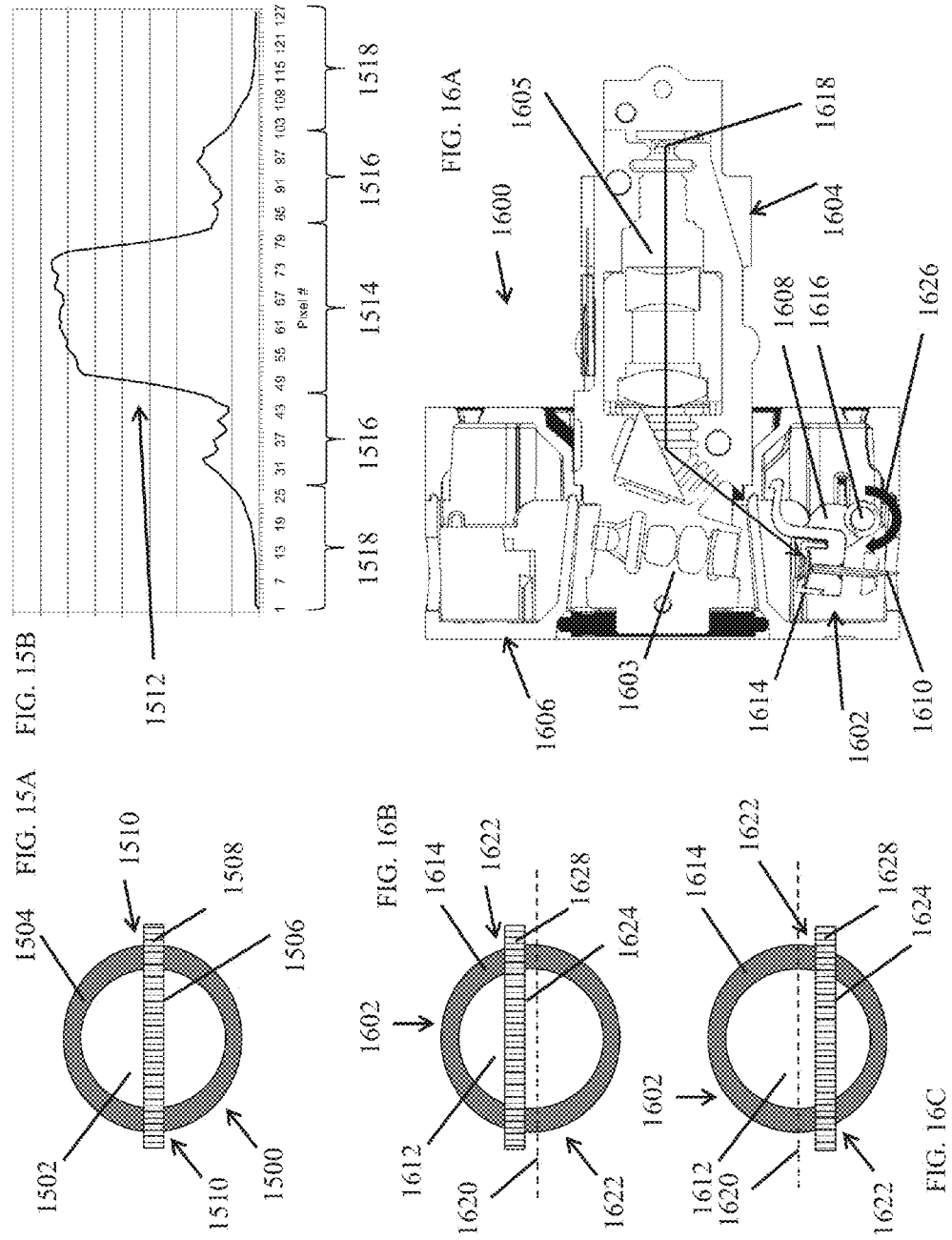

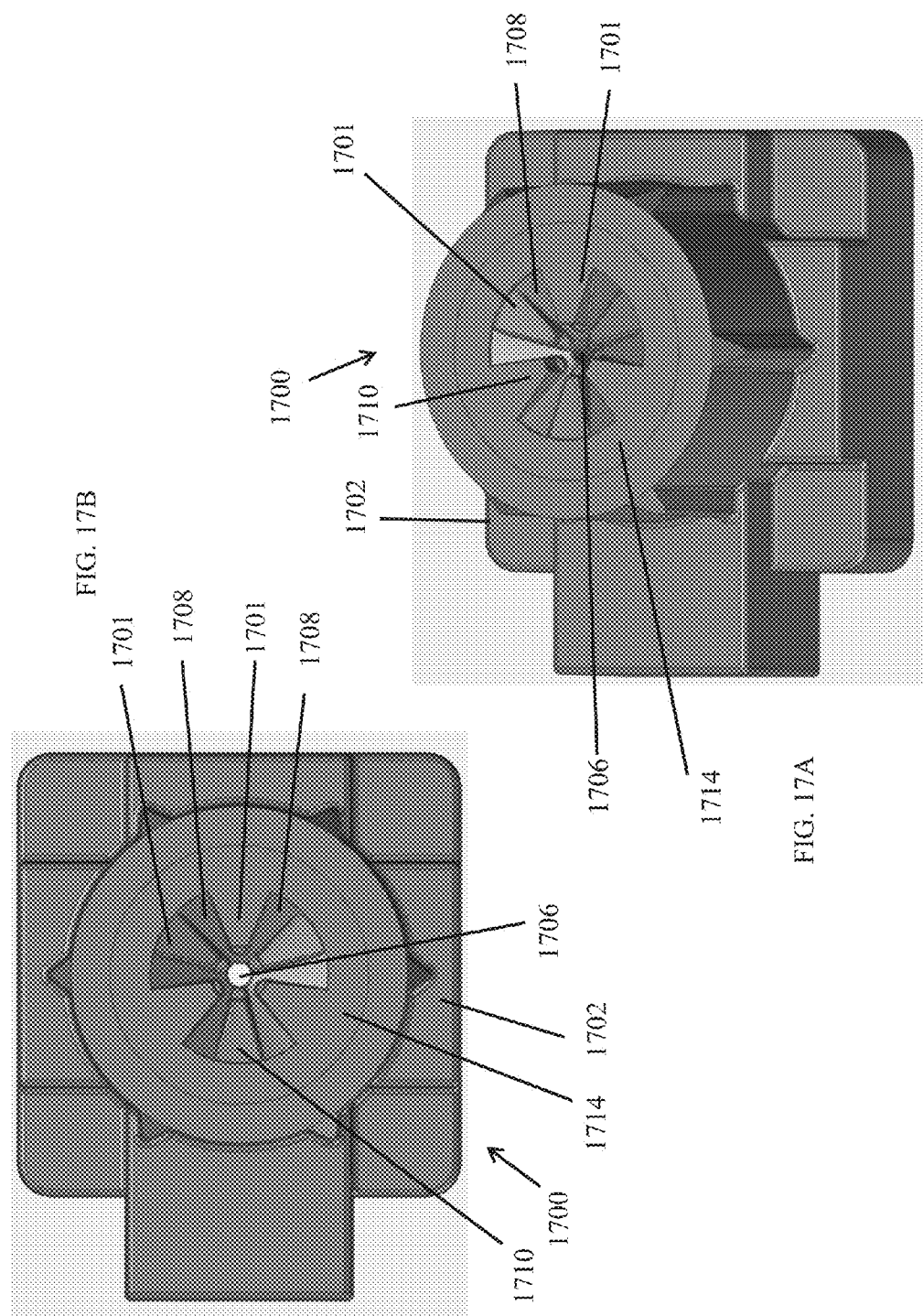

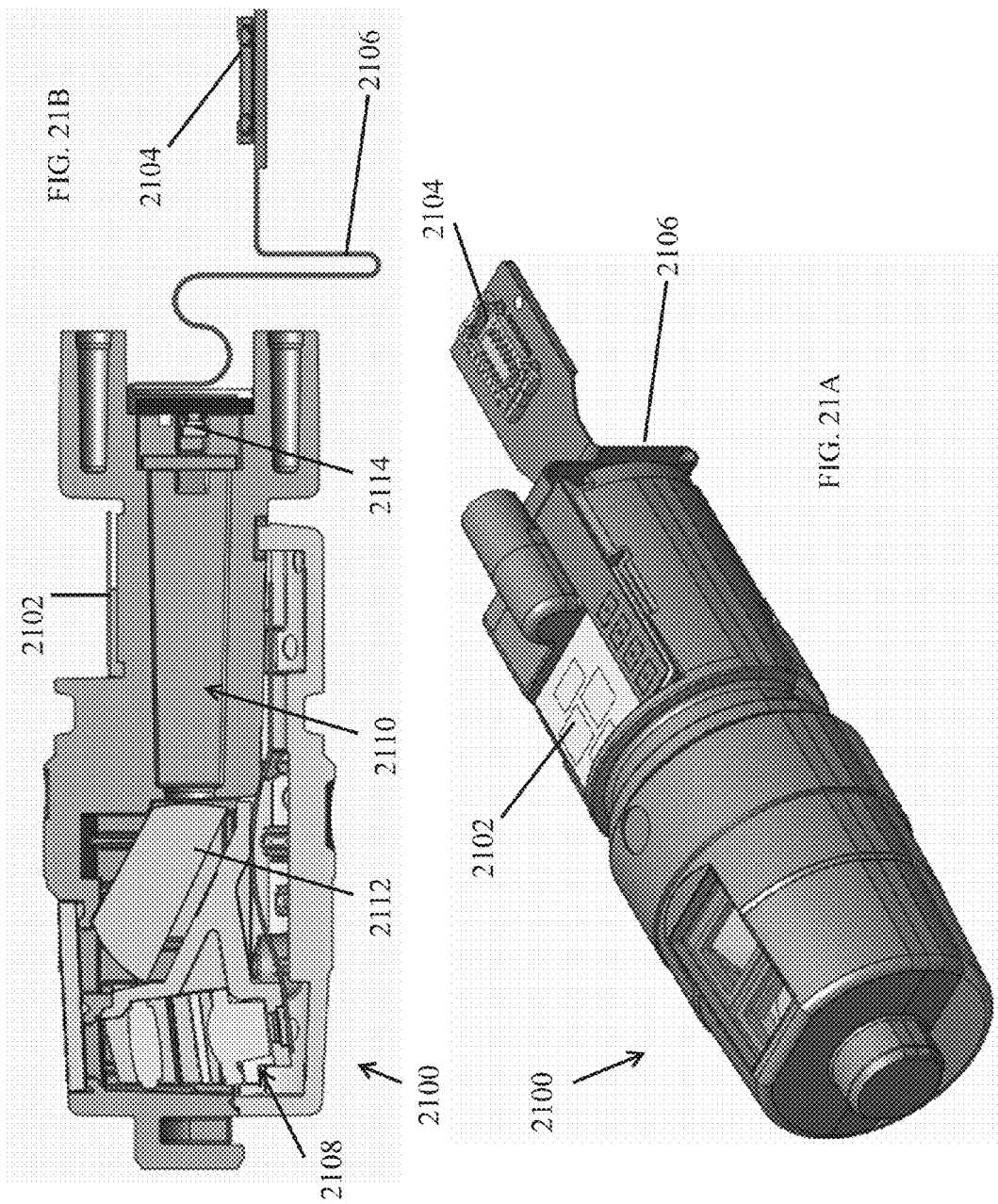

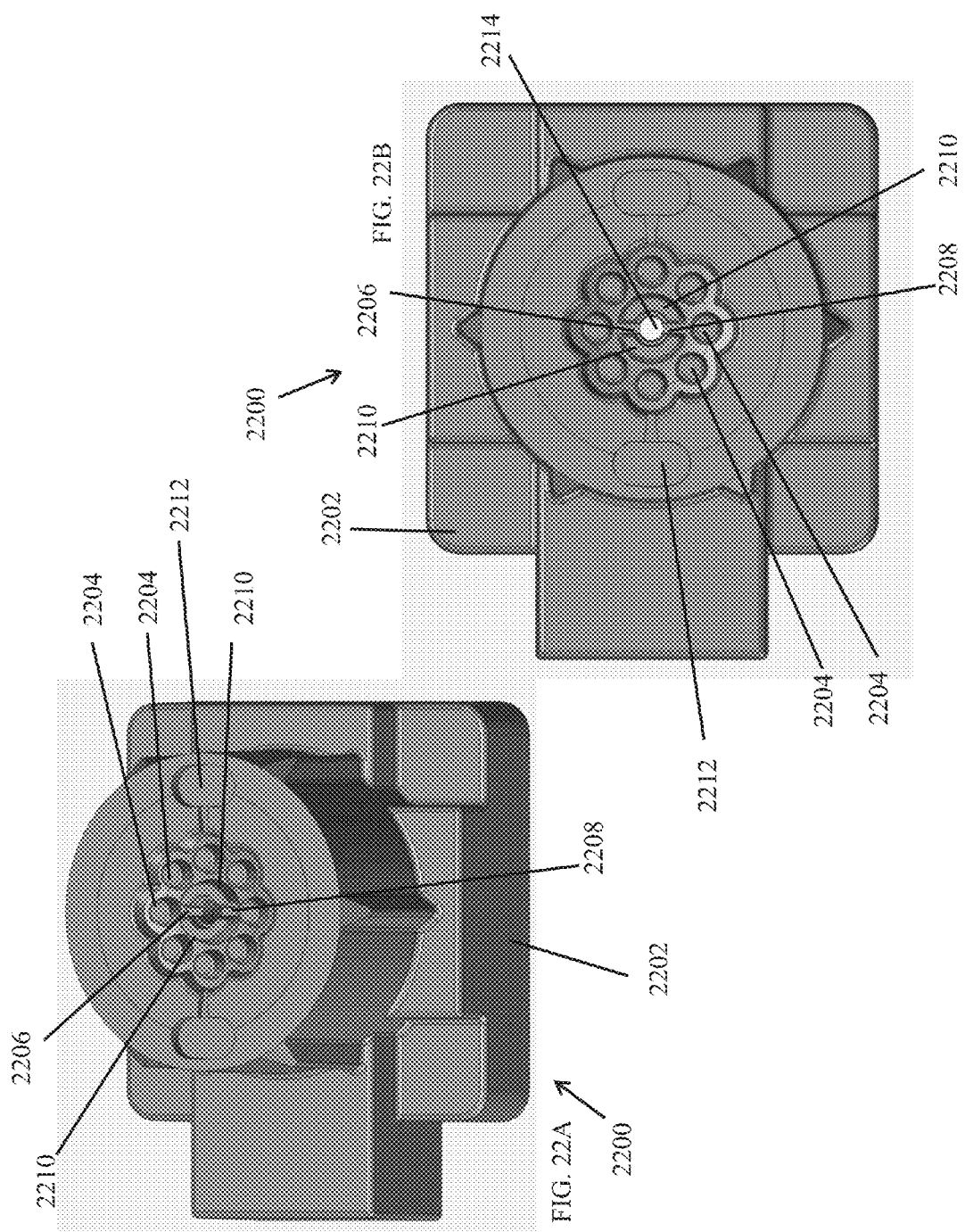

DEVICES AND METHODS FOR BODY FLUID SAMPLING AND ANALYSIS

CROSS-REFERENCE TO RELATED APPLICATIONS

This application claims priority to U.S. Provisional Application Ser. No. 61/514,872, filed on Aug. 3, 2011, which is hereby incorporated by reference in its entirety.

FIELD

The present invention relates to devices and methods for sampling, collecting, and analyzing a fluid sample (e.g., one or more body fluids)

BACKGROUND

Diabetes is a widespread condition, affecting millions worldwide. In the United States alone, an estimated 23.6 million people, or 7.8% of the population, have the condition. Diabetes accounts for an estimated $174 billion annually in direct and indirect medical costs. Depending on the type (Type 1, Type 2, and the like), diabetes may be associated with one or more symptoms such as fatigue, blurred vision, and unexplained weight loss, and may further be associated with one more complications such as hypoglycemia, hyperglycemia, ketoacidosis, neuropathy, and nephropathy.

To help prevent these undesirable complications, it may be necessary for people with diabetes to monitor one or more blood analyte levels, such as blood glucose. Glucose testing allows a patient to ensure that his or her blood glucose is at a safe level, which in turn may help monitor the effectiveness of diet, medication, and exercise in controlling the patient's diabetes, and may also help reduce the risk of developing one or more diabetes-related conditions (e.g., blindness, kidney damage and nerve damage). Many of the currently available glucose meters, however, require numerous components and complicated steps to complete a test, and often do not allow for discreet testing. This may reduce the likelihood of user compliance. As such, it may be desirable to produce safe and effective analyte concentration meters that may make sampling discrete and easier for the user and reduces the number of separate components a patient must carry.

BRIEF SUMMARY

Described here are meters and methods for sampling, transporting and/or analyzing a fluid sample. In some variations, a meter as described here may comprise a meter housing and a cartridge. In some of these variations, the cartridge and/or the meter housing may be reusable. In other variations, the cartridge and/or the meter housing may be disposable.

The cartridges described here may comprise at least one cell. In some variations, a cartridge may comprise a single cell. In other variations, a cartridge may comprise a plurality of cells. One or more portions of the cartridge may be covered by one or more covering materials. In some variations, the covering material may be opaque or otherwise light-blocking. One or more walls of the cartridge may comprise one or more transparent viewing windows, which may allow light to enter and/or exit one or more cells. The cartridge may comprise one or more recesses or other structures for receiving a portion of the meter housing.

The cartridges may comprise at least one sampling arrangements. In some variations, a cartridge may comprise a single sampling arrangement. In other variations, the cartridge may comprise a plurality of sampling arrangements. When a cartridge includes a plurality of sampling arrangements, the sampling arrangements may be positioned in one or more cells. In some variations, each of the plurality of sampling arrangements is located in a different cell. In some variations, a cartridge comprises one or more cell housing two or more sampling arrangements. In some variations, the sampling arrangements may comprise a member for collecting a fluid sample. In some of these variations, the member may comprise a penetration member (e.g., a needle, a solid lancet, or the like). The sampling arrangements may comprise a hub. The hub may be configured to connect the sampling arrangement to the cartridge. In some variations, the hub may comprise one or more pins rotatably connecting the sampling arrangement to the cartridge. In some variations, the sampling arrangement comprises a spring (e.g., a torsional spring, a linear spring, leaf spring) or another actuator that may move the sampling arrangement relative to the cartridge. In some variations, the sampling arrangement may comprise a quantification member. In some variations, the quantification member may comprise a reagent pad.

In some variations, the hub may comprise a patterned surface. In some variations, the patterned surface may comprise a fluid inlet. The fluid inlet may be fluidly connected to a penetration member or other fluid source. In some variations, the patterned surface may comprise a plurality of posts configured to spread fluid received from the fluid inlet. In some variations, the patterned surface comprises a plurality of channels and a plurality of flow diverters, wherein each channel is positioned between two of the plurality of flow diverters.

The meter housings described here may be configured to engage with and/or hold a cartridge. In some variations, a cartridge may be inserted into a cartridge-receiving chamber of the meter housing. In some instances, insertion of a cartridge into a meter housing may cause the cartridge to engage a tower within the meter housing. In some variations, the tower may be fixed relative to the rest of the meter housing. In other variations, the tower may be movable relative to the rest of the meter housing. For example, in some of these variations, the tower may be rotatably coupled to a pin, which is slidably coupled to a portion of the meter housing. In some of these variations, a spring may bias the moveable tower toward one end of the meter housing.

In some instances, insertion of a cartridge into a meter housing may place a cartridge cell between a light source and a light detector. In these variations, the light source may direct light through a viewing window of the cartridge and into the cartridge cell, and the light detector may be configured to detect any light passing through the cartridge cell (e.g., by one or more breaks or imperfections in a covering material).

The meters described here may be used to sample and analyze one or more fluid samples (e.g., blood) to determine the concentration of one or more analytes (e.g., glucose) contained therein. In some variations, a user may initiate a testing procedure by placing pressure against a port. In some of these variations, application of pressure to the port (e.g. via a contact pad) causes a cartridge and tower to move relative to the meter housing. In some instances, this movement may cause the cartridge and/or tower to engage an activation element, which may then initiate a testing procedure. During a testing procedure, a sampling arrangement may be activated to collect, transport and/or react with a fluid sample, as will be described in more detail below.

In some variations, a meter may comprise a meter housing comprising a tower and an imaging system; and a cartridge insertable into the meter housing and comprising a plurality of sampling arrangements. In some variations, the tower may be held inside the meter housing, and the tower may be configured to engage the cartridge. In some of these variations, at least a portion of the tower may fits within a recess in the cartridge when the tower engages the cartridge. The imaging system may be housed at least partially within the tower. The imaging system may comprise a light-generating assembly and a light-receiving assembly. In some variations, the meter may be configured to position the cartridge to align a first sampling arrangement of the plurality of sampling arrangements with the imaging system. The first sampling arrangement may be moveable between a pre-fired position and a rest position. In some variations, a torsional spring may be configured to move the first sampling arrangement between the pre-fired position and a rest position. In some variations the first sampling arrangement may comprise a latch configured to hold the first sampling arrangement in the pre-fired position. In some variations the meter may further comprising a triggering mechanism to release the first sampling arrangement from the pre-fired position. In some of these variations the triggering mechanism comprises a vacuum pin.

In some variations, the light-receiving assembly may be configured to image a portion of the first sampling arrangement when the first sampling arrangement is in the rest position. In some variations, the first sampling arrangement may comprise a reagent pad having a midline, and the light-receiving assembly may be configured to image a portion of the reagent pad when the first sampling arrangement is in the rest position. In some variations the light-receiving assembly comprises a linear detector array, and the light-receiving assembly may be configured to image a linear viewing area of the reagent pad when the first sampling arrangement is in the rest position. In some of these variations, the linear viewing area may be positioned on a first side of the midline when the first sampling arrangement is in the rest position. In some variations, rotation of the first sampling arrangement from the resting position toward the pre-fired position moves the viewing area in a direction toward the midline. The first sampling arrangement may further comprise a cap positioned over at least a portion of the reagent pad, wherein the light-receiving assembly is configured to image a portion of the reagent pad and a portion of the cap. In some of these variations, the light-receiving assembly is further configured to image a portion of an open space on at least one side of the cap. In some of these variations, the meter may be configured to cancel more one or more readings from the light-receiving assembly when light received by the portion of the light-receiving assembly imaging the portion of the open space reaches a predetermined threshold.

BRIEF DESCRIPTION OF THE DRAWINGS

FIGS. 1A-1D depict an illustrative variation of the meters described here. FIGS. 1A and 1B depict front and perspective views, respectively, of an illustrative variation of a meter housing. FIG. 1C depicts a perspective view of a variation of a cartridge suitable for use with the meters described here. FIG. 1D depicts a cross-sectional side view of the meter housing of FIGS. 1A and 1B with the cartridge of FIG. 1C inserted therein.

FIG. 2A depicts a bottom perspective view of the cartridge. FIG. 2B shows a cross-sectional side view. FIGS. 2C and 2D depict a top perspective view and a partial-top perspective view, respectively.

FIGS. 3A and 3B show a side view and an exploded perspective view, respectively, of the sampling arrangement. FIGS. 3C-3E illustrate a method by which a sampling arrangement may move relative to a cartridge.

FIGS. 6A-6D illustrate one variation of a meter housing suitable for use with the meters described here. Specifically, FIGS. 6A-6C show a front view, a partial cross-sectional front view, and a cross-sectional side view, respectively, of meter housing. FIG. 6D shows a cross-sectional side view of the meter housing with a cartridge inserted therein.

FIG. 7A shows a front view of one variation of a tower suitable for use with the meters described here. FIG. 7B shows a partial cross-sectional side view of the tower of FIG. 7A engaging with a variation of a cartridge suitable for use with the meters described here.

FIGS. 8A-8C illustrate one variation of a trigger mechanism suitable for use with the meters described here.

FIGS. 13A-13C depict an illustrative variation of a cartridge comprising a single sampling arrangement.

FIG. 14 depicts a variation of a sampling arrangement depicting a viewing area that may be imaged by the imaging systems described here.

FIG. 15A depicts a variation of a sampling arrangement depicting a viewing area that may be imaged by the imaging systems described here. FIG. 15B depicts a trace that may be collected by visualization of the viewing area of FIG. 15B.

FIGS. 16A-16C illustrate a variation of meter comprising a cartridge and an imaging system.

FIGS. 17A and 17B depict a perspective view and a top view, respectively, of one variation of a hub comprising a patterned surface suitable for use with the sampling arrangements described here.

FIGS. 18A and 18B depict a variation of a sampling arrangement depicting a viewing area that may be imaged by the imaging systems described here.

FIG. 19 depicts a variation of a sampling arrangement depicting a viewing area that may be imaged by the imaging systems described here.

FIGS. 20A-20C depict variations of sampling arrangements suitable for use with the meters described here.

FIGS. 21A and 21B illustrate a perspective view and a side view, respectively, of one variation of a tower suitable for use with the meters described here.

FIGS. 22A and 22B depict a perspective view and a top view, respectively, of one variation of a hub comprising a patterned surface suitable for use with the sampling arrangements described here.

DETAILED DESCRIPTION

Figure 2A:
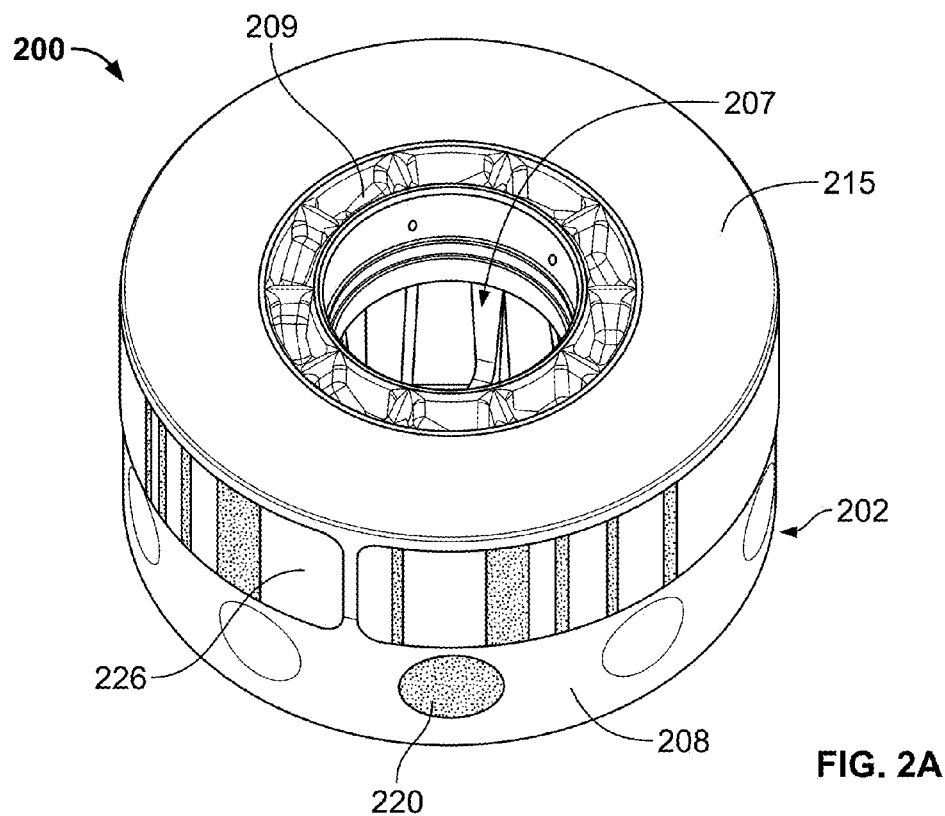
FIGS. 2A-2D illustrate a variation of a cartridge suitable for use with the meters described herein.

Described here are meters and methods for sampling, transporting and/or analyzing a fluid sample. The fluid sample may comprise any suitable fluid, such as, for example, one or more solutions (e.g., a control solution), mixtures, body fluids (e.g., blood, saliva, or the like), combinations thereof and the like. These fluid samples may be drawn from any suitable sampling site, for example, one or more body sites (e.g., fingers, toes, other skin surfaces, or the like) or one or more artificial containers (e.g., a vial holding a control solution or a body fluid sample). Once a fluid sample is collected, it may be analyzed to measure one or more parameters of the fluid sample. For example, analysis of the sample may include determining the concentration of one or more analytes in the sample. The meters may be configured to measure the concentration of any suitable analyte (e.g., hormones, proteins, enzymes, toxins, drugs, other molecules, or the like). In some variations, the meters described here may be configured to measure the glucose concentration of one or more blood samples or other glucose-containing solutions.

In some variations of the meters described here, the meter may comprise a meter housing and one or more cartridges, each of which will be described in more detail below. The meters may be fully integrated, in that the meter housing and the cartridge (or cartridges) may contain all of the components necessary for collecting, transporting, and/or analyzing a fluid sample. In some variations, the meter may be configured to collect and analyze a plurality of fluid samples. For example, in some variations, a cartridge may comprise one or more cells, some or all of which may contain one or more sampling arrangements for collecting a fluid sample, as described in more detail below. The meter may be further configured to display or otherwise provide one or more results from the sample analysis. It should be appreciated that some portions of the meter may be reusable, while other portions of the meter may be disposable. For example, in some variations the meter housing is reusable while the cartridge is disposable. In these variations, new cartridges may be inserted into or otherwise engage with a meter housing to conduct a new series of tests. In other variations, both the meter housing and the cartridge may be disposable.

FIGS. 1A-1D show an illustrative variation of the meters described here. Specifically, the meter may comprise a meter housing (100) and a cartridge (102). Specifically, FIGS. 1A and 1B show a front view and a bottom perspective view, respectively, of meter housing (100), while FIG. 1C shows a perspective view of cartridge (102). While shown in FIG. 1C as being stored in a sealable pouch (116), it should be appreciated that cartridge (102) may be stored in any suitable container, and may be removed prior to use. FIG. 1D shows a cross-sectional view of meter housing (100) with cartridge (102) placed inside of meter housing (100). As shown there, meter housing (100) may comprise a door (104) with a cartridge-engagement projection (105), a cartridge-receiving chamber (106) or cavity, triggering mechanism (107), display (108), buttons (110), port (112), and tower (114). The meters described here need not include each of these features, and it should be appreciated that the meters described here may comprise any combination of these features. Each of these features will be described in more detail below. Meter housing (100) may further comprise one or more imaging systems (not shown), and internal mechanisms or components (e.g., memory, circuitry, actuators, batteries, vacuum pumps, sensors, combinations thereof, etc.) for operating the meter and/or facilitating a testing procedure.

Door (104) may be opened to reveal cartridge-receiving chamber (106), as shown in FIG. 1B. Cartridge (102) may be placed inside of cartridge-receiving chamber (106), and door (104) may be closed to temporarily enclose cartridge (102) within the meter housing (100). When placed inside of meter housing, one or more portions of the cartridge may engage one or more components of the meter housing (100). In some variations, meter housing (100) may comprise one or more features that may facilitate self-alignment of the cartridge (102) as it is placed in the cartridge-receiving chamber (106), as will be described in more detail below. In some variations, the cartridge (102) may comprise a recess (not shown). When cartridge (102) is placed inside of cartridge-receiving chamber (106), a portion of tower (114) may fit within or otherwise engage the recess of cartridge (102). This engagement may help to hold cartridge (102) in place relative to meter housing (100). Conversely, in some variations the cartridge (102) may comprise one or more projections (not shown) that may engage one or more recesses (not shown) in the cartridge-receiving chamber (106) or other portion of the meter housing (100). Additionally or alternatively, one or more magnets may hold the cartridge in place relative to the meter housing. It should be appreciated that a cartridge need not be placed inside of a meter housing (e.g., via a cartridge-receiving chamber) to engage the meter housing. For example, in some variations, a cartridge may attach to or otherwise engage one or more external surfaces of a meter housing.

When the door (104) of a meter housing (100) comprises a cartridge-engagement projection (105). The cartridge-engagement projection (105) may press against or otherwise bias the cartridge (102) when a cartridge (102) is placed in a cartridge-receiving chamber (106) and the door (104) is closed. For example, when a portion of a tower (114) engages the cartridge (102), the cartridge-engagement projection (105) may press and hold the cartridge (102) in engagement with the tower (114). This engagement may help account for mechanical tolerances of the meter. In some variations, the cartridge-engagement projection (105) may be spring-loaded to bias the cartridge (102).

Additionally, cartridge (102) may house or otherwise hold one or more sampling arrangements (130). These sampling arrangements, as will be described in more detail below, may be contained in one or more cells of the cartridge, and may comprise one or more components for collecting, transporting, and/or reacting with a fluid sample. For example, in some variations, the sampling arrangement (130) may comprise a penetration member (136) for piecing, penetrating or otherwise puncturing a sampling site during a testing procedure. In variations where the cartridge (102) comprises a plurality of sampling arrangements, each sampling arrangement may be utilized to conduct a separate test on a different fluid sample. In variations where cartridge (102) is configured to be disposable, new cartridges may be swapped in to provide unused (e.g., unfired) sampling arrangements.

Once the cartridge (102) has been placed in operative engagement with the meter housing (100), the meter may be configured to perform one or more testing procedures, during which a fluid sample is collected and analyzed. Prior to initiating a testing sequence, the meter may first be activated by one or more of buttons (110) or another suitable switch, lever, pressure sensor, or the like. Activating the meter may comprise powering up the meter housing (100), or may comprise waking the meter from a hibernation mode.

It should be appreciated that the meter may be activated (e.g., powered up or awoken from a hibernation mode) prior to placement of cartridge (102) in meter housing. In other variations, placement of the cartridge (102) inside of the meter housing (100) may activate the meter.

Upon activation of the meter and/or placement of cartridge (102) in the meter housing (100), the meter may be configured to run one or more procedures to check the integrity of, index, and/or otherwise obtain information from the cartridge (102), as will be described in more detail below. In some of these procedures, the meter may be configured to evaluate whether individual sampling arrangements of the cartridge (102) have previously been used, fired, or otherwise actuated (intentionally or inadvertently). In variations where portions of the cartridge are sealed from the external environment, the meter may be configured to check the integrity of the seal. Additionally or alternatively, the meter housing (100) may be configured to obtain information (e.g., calibration information, expiration dates, etc.) stored on, stored in, or otherwise associated with the cartridge (102). If the meter determines that the cartridge has expired, or all of the sampling arrangements have either been used or otherwise comprised, the meter may be configured to prevent the initiation of a test, and may additionally alert the user (e.g., via one or more visual prompts, sounds, tactile stimuli, or other identifiers) to insert a new cartridge (102).

In order to insert a new cartridge, it may be first necessary to remove a cartridge that is already housed in a meter housing. A cartridge may be ejected or removed from the meter housing in any suitable manner. It should be appreciated that in some variations, the meter housing (100) may be configured to eject a used cartridge (102) without requiring direct user contact with the cartridge, which may help to reduce the risk of user exposure to potentially hazardous materials (e.g., used needles or lancets). For example, in some variations, the meter housing (100) may comprise one or more ejection buttons (113), that may be depressed or otherwise activated to eject the cartridge (102) from the meter housing (100) without requiring a user to touch the cartridge (102). In other variations, the cartridge (102) may be configured to passively fall from the cartridge housing when a door (104) of the meter housing (100) is opened. Examples of illustrative cartridge ejection mechanisms will be described in more detail below.

After any checking/indexing/information gathering procedures have been completed, the meter may enter a ready mode, in which cartridge (102) is positioned such that an un-fired sampling arrangement is in alignment with port (112), as shown in FIG. 1D. At this point, a user may initiate a testing procedure. Alternatively, the alignment of a sampling arrangement with the port (112) may not occur until after the testing procedure has been initiated. In some instances, the testing procedure may be initiated by pressing one or more of buttons (110) or activating another suitable element (e.g., one or more buttons, switches, levers, sensors, combinations thereof, and the like). In other instances, a user may activate a testing procedure by placing a sampling site (e.g., one or more skin surfaces or a fluid-filled container) against port (112), as will be described in more detail below. For example, the port (112) may comprise a moveable contact pad against which a user may press a sampling site (e.g., a skin surface), and which may contact a portion of the cartridge when a sampling site is applied thereto.

Once a testing procedure has been initiated, the meter may be configured to activate or otherwise actuate the sampling arrangement (e.g., via a trigger mechanism or the like) to pierce, puncture, or otherwise penetrate the sampling site. The sampling arrangement may further be configured to draw or otherwise collect a fluid sample from the sampling site. Additionally, vacuum, pressure, and/or heat may be applied to the sampling site before, during, or after the sampling arrangement collects the fluid sample. In variations where vacuum is applied to the sampling site, the amount of vacuum may be varied or otherwise modulated, as will be described in more detail below. Additionally or alternatively, in some variations the sampling site may be mechanically stimulated using vibrations, massage, or the like. As the fluid sample is collected, the meter may analyze the fluid sample, as will be described in more detail below. Analysis of a fluid sample may include determining the concentration of one or more target analytes (e.g., glucose) in the fluid sample. In some variations, the meter may be configured to determine whether the fluid sample collected by a sampling arrangement is a control sample. The meters described here may comprise one or more imaging systems which may image one or more portions of the sampling arrangement during analysis of the fluid sample. Specific meter components, and methods for using these meters, will be described in more detail below.

Cartridge

As mentioned above, the meters described here may comprise one or more cartridges. Generally, the cartridge may engage, fit within, and/or attach to a meter housing, and may comprise one or more sampling arrangements housed within one or more cartridge cells. As will be described in more detail below, the sampling arrangements may comprise specific components for obtaining, transporting and/or reacting with a fluid sample. Any reactions that occur between sampling arrangement and the fluid sample may be quantified or measured by one or more portions of the cartridge or the meter housing (e.g., an imaging system), as will be described in more detail below. The cartridge may be removable from the meter, or may be integrated into the meter. When the cartridge is removable from the meter, it may or may not be configured to be disposable. In some variations, one or more portions of the cartridge may be reusable. For example, a cartridge containing one or more unused sampling arrangements may be loaded into the cartridge to allow the meter to conduct additional testing procedures.

Figure 2B:
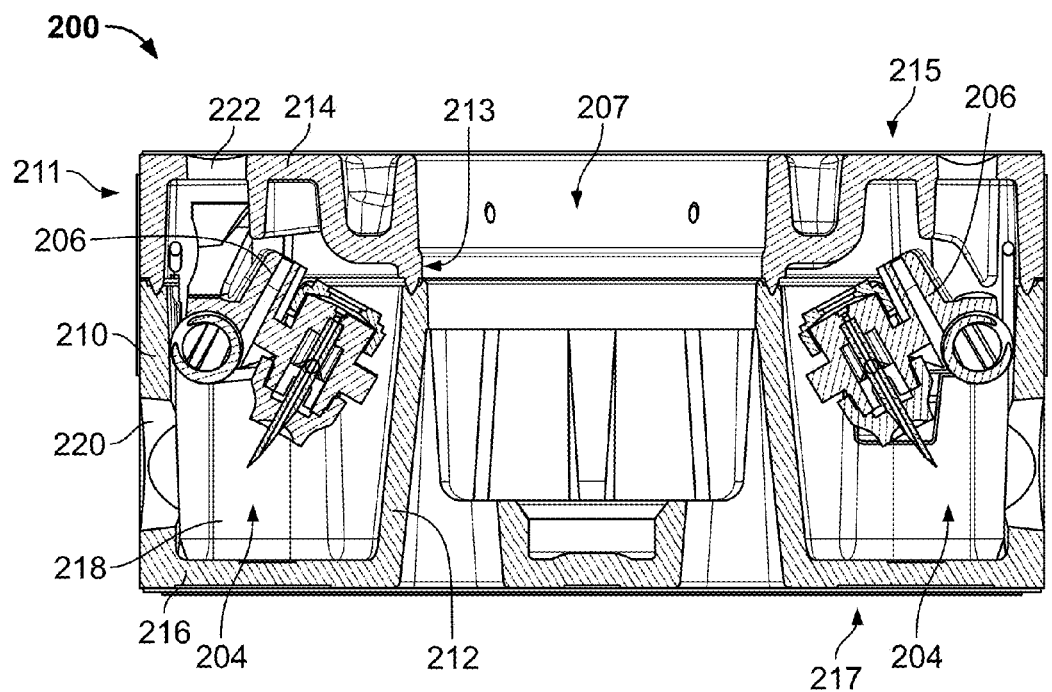
Figure 2C:
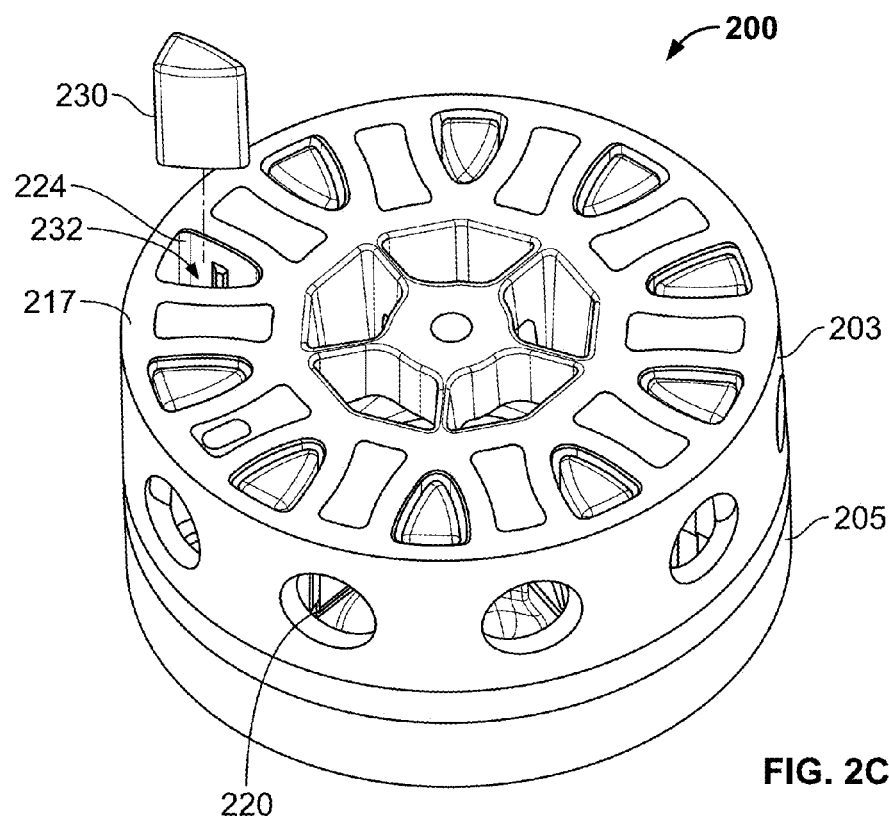
Figure 2D:
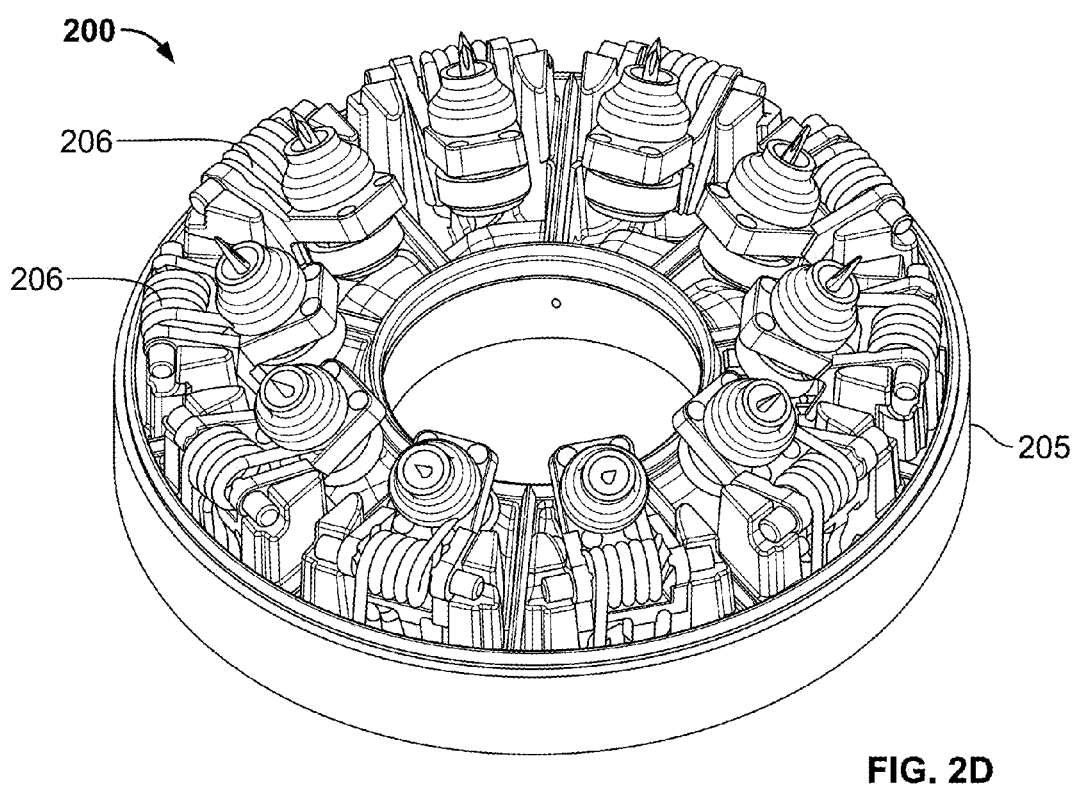

Any suitable cartridge may be used with the meters described herein. For example, in some variations, the meter may comprise one or more of the cartridges described in U.S. patent application Ser. No. 11/529,614, titled "MULTI-SITE BODY FLUID SAMPLING AND ANALYSIS CARTRIDGE," and Ser. No. 12/222,724, titled "ANALYTE CONCENTRATION DETECTION DEVICES AND METHODS," the contents of each is hereby incorporated by reference in its entirety. FIGS. 2A-2D illustrate one variation of cartridge (200) suitable for use with the meters described herein. Specifically, FIGS. 2A and 2B show bottom perspective and cross-sectional views, respectively, of cartridge (200). FIGS. 2C and 2D show a top perspective view, and a partial-top perspective view, respectively of cartridge (200). As shown in these figures, cartridge (200) may comprise a housing (202) that may be divided into a plurality of separate cells, such as cells (204). One or more of the cells (e.g., cells (204)) may comprise one or more sampling arrangements (206), such as one or more of those described in more detail below. Cartridge (200) may comprise a recess (207) extending at least partially through the cartridge housing (202). One or more portions of a meter housing may extend at least partially through the recess (207) to engage the cartridge (200), as will be described in more detail below. Housing may also comprise teeth (209), which may engage a portion of the meter housing (not shown) to help align and move the cartridge relative to the meter housing, as will be described in more detail below. Additionally, at least a portion of cartridge may be sealed, covered, or otherwise masked by one or more sections of covering material (208), as shown in FIG. 2A. Covering material (208) is not shown in FIGS. 2B-2D so as to allow for better illustration of the remaining components of the cartridge (200).

While shown in FIG. 2C as being formed from two separate pieces (top segment (203) and bottom segment (205)), it should be appreciated that housing (202) may be made from any suitable number of separate pieces (e.g., one, two, three, or four or more). FIG. 2D shows cartridge (200) with a top segment (203) of the housing (202) removed, revealing the plurality of sampling arrangements (206).

While shown in FIGS. 2A-2D as comprising a plurality of sampling arrangements (206), the cartridge may house only a single sampling arrangement (206) if desirable. In these variations, the cartridge may be configured to run a single testing procedure, at which point the cartridge may be removed and replaced with an unused cartridge, as will be described in more detail below. In variations where the cartridge (200) comprises a plurality of sampling arrangements, the cartridge may comprise any suitable number (e.g., two, three four, five, six, seven, eight, nine, ten, eleven, or twelve or more) of sampling arrangements. Different sampling arrangements within the cartridge may comprise the same elements and the same configuration of elements, or may comprise different elements or different element configurations. For example, some sampling arrangements in a cartridge may be configured to react with and allow for the measurement of a first analyte concentration in a fluid sample, while other sampling arrangements may be configured to react with and allow for the measurement of a second analyte. In other instances, some sampling arrangements may be actuated or moved by a torsional spring, while other sampling arrangements may be actuated or moved by a linear spring or leaf spring. Additionally or alternatively, one or more sampling arrangements may be actuated by an electromechanical or pneumatic actuator.

Additionally, while each sampling arrangement (206) shown in FIGS. 2A-2D is housed in a separate cell (204), it should be appreciated that in some instances multiple sampling arrangements may be placed in a single cell. For example, in some variations it may be desirable to obtain and analyze two or more fluid samples simultaneously. Furthermore, some cells may not house or otherwise comprise a sampling arrangement. For example, one or more cells may be configured to hold, house, or otherwise contain one or more memory units, an optical reference (e.g., one or more colored members), a desiccant, a sensor for determining exposure to the external environment, or the like. While shown in FIGS. 2A-2D as being substantially cylindrical, the cartridges described here may have any suitable shape. In some variations, the cartridge may be box- or disc-shaped.

The cells of the cartridge may comprise one or more walls. For example, as shown in FIG. 2B, cell (204) may comprise outer perimeter wall (210) in an outer perimeter surface (211) of the cartridge, inner perimeter wall (212) in a perimeter surface (213) of recess (207), top wall (216) in a top surface (217) of the cartridge, bottom wall (214) in a bottom surface (215) of the cartridge, and side walls (218) separating adjacent cells (204). In some variations, one or more of the walls may include one or more apertures or holes therethrough, which may allow access to the interior of the cartridge cell (204) (or may allow one or more elements of the sampling arrangement to exit the meter). For example, as shown in FIGS. 2A-2C, the outer perimeter wall (210) of each cell (204) may comprise an aperture (220). One or more portions of the sampling arrangement (206) may pass through aperture (220) during a testing procedure. Additionally or alternatively, the bottom wall (214) of a cell (204) may comprise one or more apertures, such as aperture (222) shown in FIG. 2B. In some variations, a portion of one or more vacuum sources or trigger mechanisms (not shown) may be advanced into a cell (204) through aperture (222) to apply vacuum pressure to the cell and/or to engage the sampling arrangement. Additionally or alternatively, the top wall (216) of a cell may comprise one or more apertures, such as aperture (224) shown in FIG. 2C. In some variations, one or more side walls (218) of a cell (204) may comprise an aperture (not shown), which may allow for gaseous communication between adjacent cells.

As mentioned above, one or more desiccant pieces may be packaged with and/or inside of the cartridge. The desiccant may help absorb moisture inside of the cartridge, which may help increase the shelf life of the cartridge by minimizing interaction between any moisture and one or more reagents or other chemicals housed in the cartridge. In some variations, one or more portions of the cartridge housing may be made from a desiccant material. In variations where the cartridge comprises a plurality of cells, one or more pieces of desiccant may be placed in one or more of the cartridge cells. In variations where one or more cartridge cells comprise a sampling arrangement, a piece of desiccant may be placed in the same cell as a sampling arrangement. In other variations, a piece of desiccant may be placed in a cell that does not comprise a sampling arrangement. In some of these variations, one or more apertures may connect a cell that comprises a sampling arrangement with a cell that holds a piece of desiccant, thereby providing gaseous coupling between the desiccant and the sampling arrangement. For example, in the variation of cartridge (200) described above in respect to FIGS. 2A-2D, one or more desiccant pieces (230) may be placed inside of a cartridge cell (232) via aperture (224). An aperture (not shown) may gaseously couple cell (232) and an adjoining cell (204) containing a sampling arrangement (206), which may allow the one or more desiccant pieces (230) to draw moisture from cell (204) into cell (232), where is may be absorbed by the one or more desiccant pieces (230).

In some variations each desiccant-containing cell (232) may be gaseously coupled to a single sampling arrangement-containing cell (204). In these variations, exposure of a single sampling arrangement-containing cell (204) to the environment (e.g., during a testing procedure, as will be described in more detail below) may allow other cells (204) to remain isolated from the environment. In other variations, a desiccant-containing cell (232) may be coupled to multiple sampling arrangement-containing cells (204).

In some variations, one or more portions of a cell wall may be transparent, which may allow the portion of the cell to act as a viewing window. These viewing windows may be made from any suitable transparent material or materials (e.g., glass, plastic, etc.), and may allow for visualization of the interior of the cartridge by an imaging system, such as those described in more detail below. In some variations, only a portion of a wall may be made from a transparent material. In other variations, an entire wall may be made from a transparent material or materials, and thus the entire wall may act as a viewing window. Any suitable cell wall or walls may act as a viewing window (e.g., a top wall, a bottom wall, and/or a perimeter wall). In other variations, one or more apertures in a cell wall may allow for visualization of the interior of the cartridge by an imaging system. In variations where an aperture is covered by one or more covering materials (as described immediately below), it may be necessary to first remove the covering material from the aperture for it to be used as a viewing window. In other variations, a covering material may be transparent, which may allow for visualization through the covering material.

Although shown in FIG. 2A above as comprising one or more sections of a covering material (208), cartridge (200) need not. In variations that do comprise a covering material, the covering material may be used to cover one or more surfaces and/or apertures of the cartridge housing (200). When the covering material covers the apertures of a cell, the covering material may act to form a temporary barrier between the external environment and the cartridge interior, thereby temporarily sealing the cartridge cell. By sealing the individual cells from the external environment, covering material may help prevent or minimize the risk of external stimuli (e.g., gases, moisture, etc.) affecting the shelf life of or contaminating one or more portions of the sampling arrangement. Additionally, the covering material may be used to trap one or more gases (e.g., a nitrogen-based gas or mixture) inside of the cartridge cells, which may increase the shelf life of the sealed cartridge. The covering material may at least temporarily cover any surfaces and/or apertures of the cartridge. For example, in the variation of cartridge (200) shown in FIG. 2A, covering material (208) may cover the top surface (217), outer perimeter surface (211) and bottom surface (215) of the cartridge, including apertures (220), (222), and (224) in these surfaces. In this variation, at least a portion of the transparent inner perimeter walls (212) may remain uncovered to allow visualization therethrough. Alternatively, the transparent inner perimeter walls (212) may be covered by a transparent covering material (not shown).

Covering material (208) may be made from any suitable material or materials (e.g., a metal foil such as aluminum, steel, or the like, a plastic membrane such as ethyl vinyl acetate, polyethylene, polyester, or the like, combinations or composites thereof, and the like), and may be attached to a cartridge in any suitable manner (e.g., one or more adhesives, such as a pressure-sensitive or heat-sensitive adhesive). The covering material may be made from a single or multiple layers of material. In variations in which the covering material is a multi-layered covering, the various layers may be made from different materials, but need not be. In some variations, one or more portions of the covering material may be substantially opaque or otherwise impervious to light. In these variations, the light-blocking covering material may help the meter assess the integrity of the seal provided by the covering material, as will be described in more detail below. Additionally, in some variations a single piece of covering material may be used to cover the cartridge. In other variations, different pieces of covering material may be used to cover different surfaces (or portions thereof) of the cartridge. For example, in some variations a first piece of covering material may cover a bottom surface, a second piece may cover an outer perimeter surface, and a third piece may cover a top surface of the cartridge. In some of these variations, the different pieces of covering material may be the same material or may be different materials. For example, in some variations a first piece of covering material covering a bottom surface of the cartridge may include a first layer comprising low density polyethylene (LDPE) and a second layer comprising a metal foil (e.g., aluminum foil), while a second piece of covering material covering an outer perimeter surface may include a first layer comprising ethyl vinyl acetate and a second layer comprising a metal foil (e.g., aluminum foil). In still other variations, different pieces of covering material may seal different cartridges.

During operation of the meter, one or more portions of the covering material may be punctured, moved, or otherwise removed to facilitate sampling and/or analysis of a fluid sample. For example, removal of the covering material overlying an aperture may present an unimpeded path for a portion of a sampling arrangement to pass through the aperture. In the variation of cartridge (200) shown in FIG. 2A, a portion of covering material (208) overlying aperture (220) has been removed/punctured to provide access to the interior of cartridge (204). In variations where a portion of the covering material is removed to provide access to interior of a cartridge, the covering material may be configured to aid in removal. For example, in some variations, the covering material may comprise a first layer comprising ethyl vinyl acetate and a second layer comprising a metal foil (e.g., aluminum). In these variations, the ethyl vinyl acetate may facilitate breaking or rupturing of the covering material as it is punctured or otherwise removed (e.g., via a punch, as will be described in more detail below). In other instances, a portion of a sampling arrangement may pierce or puncture the covering material upon activation of the sampling arrangement.

In still other instances, one or more vacuum tubes or triggering mechanisms may puncture the covering material to gain access to the interior of a cell. In some of these variations, the covering material may comprise one or more materials which may act to form a seal around a vacuum tube or a triggering mechanism when the tube or mechanism punctures the covering material. For example, in some variations, one or more apertures may be covered by a covering material that may comprise a first layer comprising low density polyethylene (LDPE) and a second layer comprising a metal foil (e.g., aluminum foil). In these variations, the elastic nature of the LDPE may seal around a vacuum tube or triggering mechanism as it punctures the covering material.

In some variations, a cartridge may be configured to carry information relating to the cartridge or one of the components thereof. The cartridges may carry any suitable information (e.g., calibration codes, batch information, expiration information, and the like) in any suitable manner. For example, in the variation of cartridge (200) shown in FIG. 2A, cartridge (200) may comprise one or more barcodes (226). In these variations, the meter housing (not shown) may comprise one or more barcode scanners/readers. In variations where the cartridges are cylindrical or have an otherwise rounded cross-sectional area, the cartridge may be rotated to facilitate reading the barcode. In other instances, the meter housing may be configured to move the cartridge into a position where the barcode may be read. The cartridge may comprise any suitable number of barcodes (e.g., zero, one, two, three, or four or more barcodes).

While shown in FIG. 2A as comprising a barcode (226), cartridge (200) need not. In some variations, the cartridge may comprise one or more memory chips or cards, which may convey information to the meter housing, such as, for example, through RF transmission, optical communication, or via direct electrical communication. In these variations, the meter housing may be further configured to upload/input data or other information into the cartridge memory. For example, the meter housing may upload date information in the cartridge relating to the first use of said cartridge. In this way, if the cartridge is placed in a different meter housing, the new meter housing may download the first usage date of the cartridge. This may be of particular relevance in instances where a cartridge has a limited shelf life after its first usage, or after removal from a sterile packaging. In other variations, a separate memory card or chip may be packaged and/or provided with the cartridge. This memory card or chip may be inserted into a portion of the meter to convey information to the meter. In still other variations, a user or physician may manually enter information regarding the cartridge into the meter.

Figure 13A:
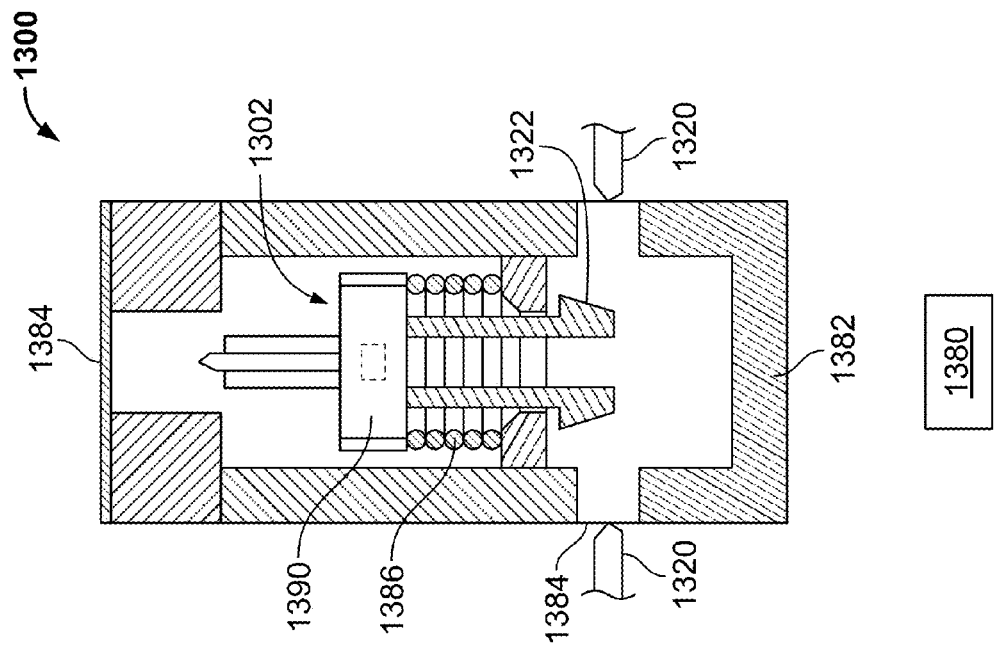

While cartridge (200) discussed above in relation to FIGS. 2A-2D comprises multiple sampling arrangements, it should be appreciated that a cartridge may comprise a single sampling arrangement. For example, FIGS. 13A-13C depict an illustrative variation of a cartridge (1300) comprising a single sampling arrangement (1302). FIGS. 13A, 13B, and 13C show a side, cross-section view of a single sampling arrangement (1302) in a loaded position, an extended position, and a rest position, respectively. While shown in FIG. 13A as having a covering material (1384), the cartridge need not. In variations of cartridges that do comprise a covering material (1384), one or more portions of the covering material (1384) may be removed and/or punctured during operation of the device. Cartridge (1302) may be loaded into a cartridge-receiving chamber of a meter housing (not shown), such as one or more of the meter housings described hereinthroughout. When placed inside of a meter housing, the cartridge (1302) may be positioned relative to an imaging system (1380) such that an interior of the cartridge (1302) may be viewed through a transparent window (1382), as described in more detail below.

While sampling arrangement (1302) is shown in FIGS. 13A-13C as having a hub (1390), penetration member (1388), and linear spring (1386), it should be appreciated that sampling arrangement (1302) may have any elements or combinations of elements as will be described in more detail below. When cartridge (1302) is in place within the meter housing, the meter may comprise one or more triggering mechanisms that may activate sampling arrangement (1302). In the variation shown in FIGS. 13A-13C, one or more trigger pins (1320) may press against one or more latches (1322) of hub (1390) to actuate the sampling arrangement (1302), which may move from a loaded position as shown in FIG. 13A to an extended position as shown in FIG. 13B, and eventually to a rest position in FIG. 13C. The sampling arrangement (1302) may be configured to collect a fluid sample when in the extended and/or rest positions, and the fluid sample may be analyzed (e.g., visualization of the sampling arrangement (1302) by the imaging system (1380) before, during, and/or after collection of the fluid sample may assist in analysis of the fluid sample). Following collection and/or analysis of the fluid sample, the cartridge (1302) may be removed from the meter housing, and a fresh cartridge with an unused sampling arrangement may be placed in the meter housing.

It should be appreciated that the cartridges suitable for use with the meters described here may comprise any combination of elements or features described above, and may comprise any sampling arrangements or combination of sampling arrangements described below.

Sampling Arrangements

The cartridges described above generally comprise one or more sampling arrangements for obtaining, transferring, and/or reacting with one or more fluid samples. Any suitable sampling arrangements may be used with the meters described here, such as those described in U.S. patent application Ser. No. 11/529,614, titled "MULTI-SITE BODY FLUID SAMPLING AND ANALYSIS CARTRIDGE," the content of which is hereby incorporated by reference in its entirety. Generally, the sampling arrangements may comprise one or more penetration members for piercing, puncturing or otherwise penetrating a sampling site (e.g., a skin surface) and/or collecting a fluid sample from the sampling site. The sampling arrangement may further comprise a hub or other structure for moving the penetration member relative to the cartridge. Additionally, the sampling arrangement may comprise a quantification member, which may react with the fluid sample to produce a measurable response (e.g., an electrochemical or photometric response) that may be indicative of one or more properties of the fluid sample.

Figure 3A:
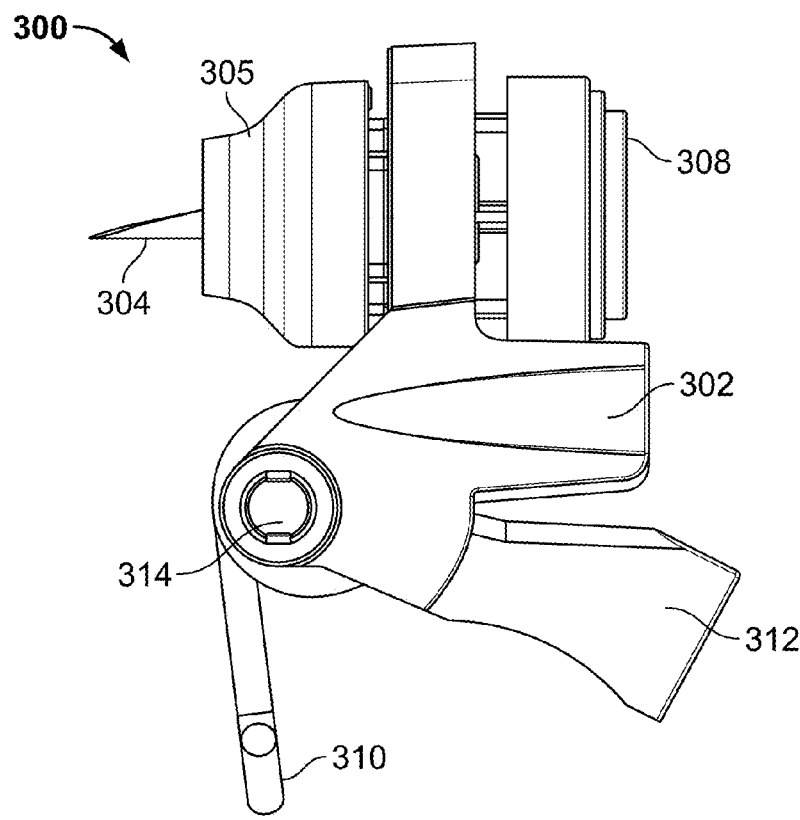
FIGS. 3A-3E illustrate a variation of a sampling arrangement suitable for use with the meters described here.
Figure 3B:
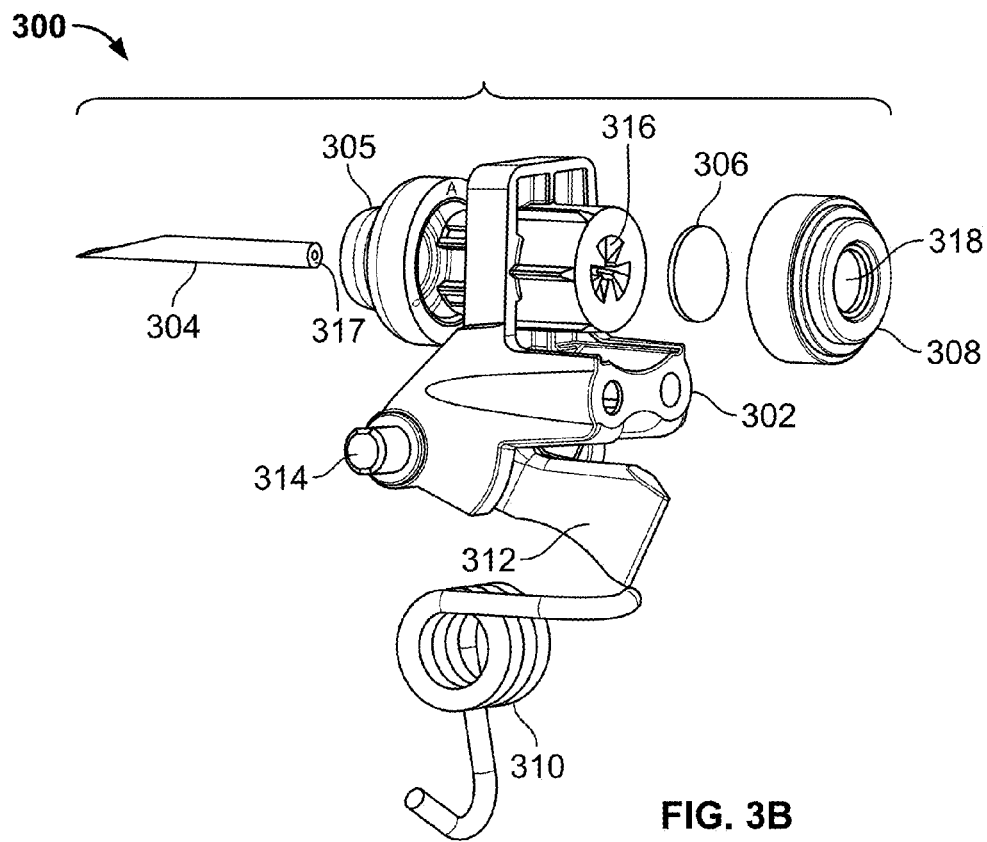

FIGS. 3A-3E illustrate a variation of a sampling arrangement (300) suitable for use with the meters described here. FIGS. 3A and 3B show a side view and an exploded perspective view, respectively, of sampling arrangement (300). Shown there are hub (302), needle (304), standoff (305), pad (306), cap (308), and torsional spring (310). Hub (302) may comprise latch (312), pivot bars (314), and a micropatterned surface (316). In this variation, hub (302) may hold needle (304) such that an interior bore (317) of the needle is in fluid communication with micropatterned surface (316). Pad (306) or another quantification member may be placed on micropatterned surface (316), and cap (308) may be placed at least partially over pad (306) to hold the pad (306) in place against the micropatterned surface (316). Cap (308) may comprise an aperture (318) or other viewing window through which the pad (306) may be viewed.

Figure 3C:
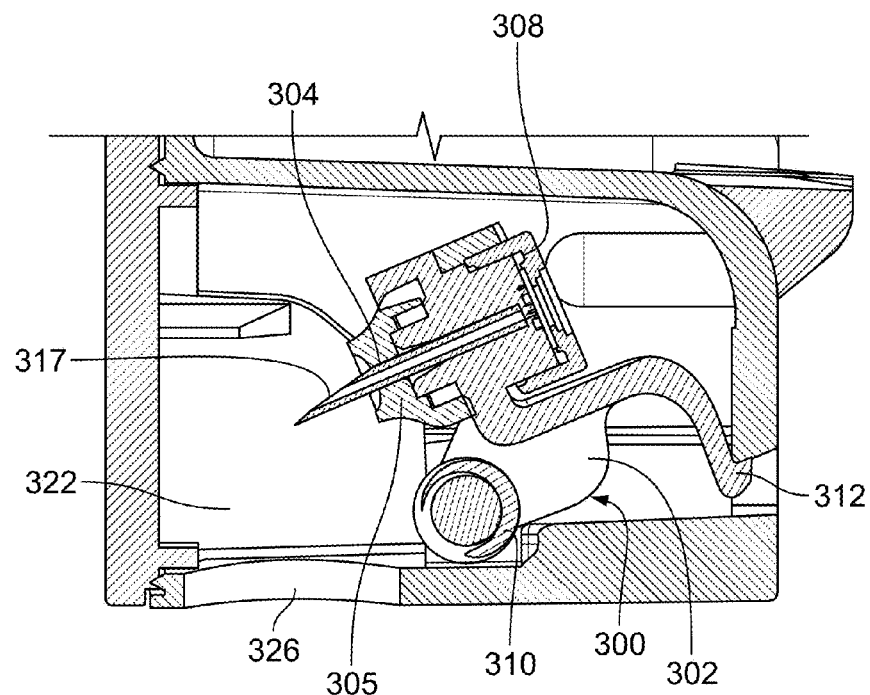
Figure 3D:
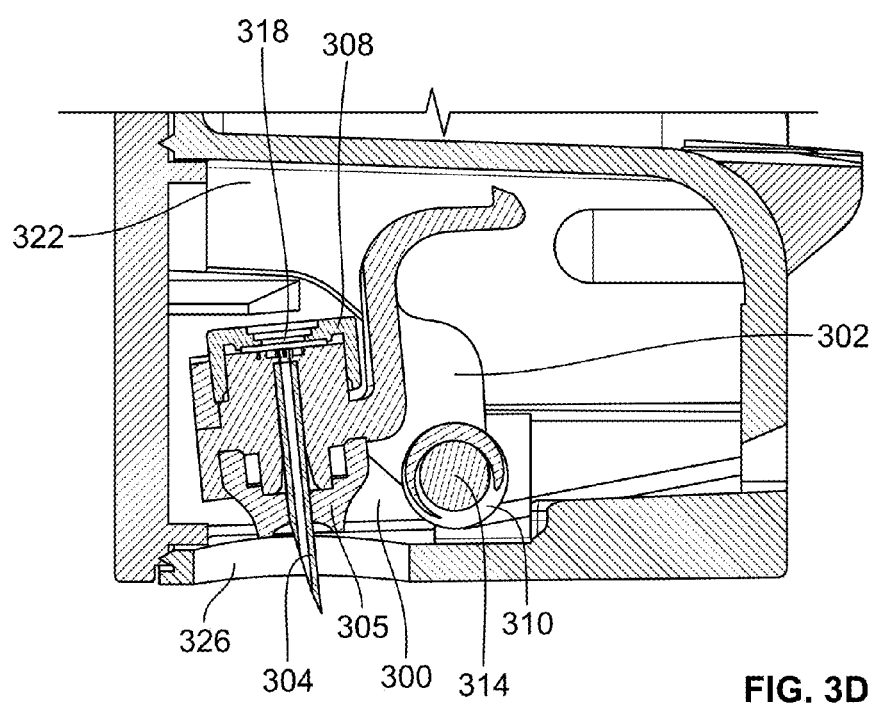
Figure 3E:
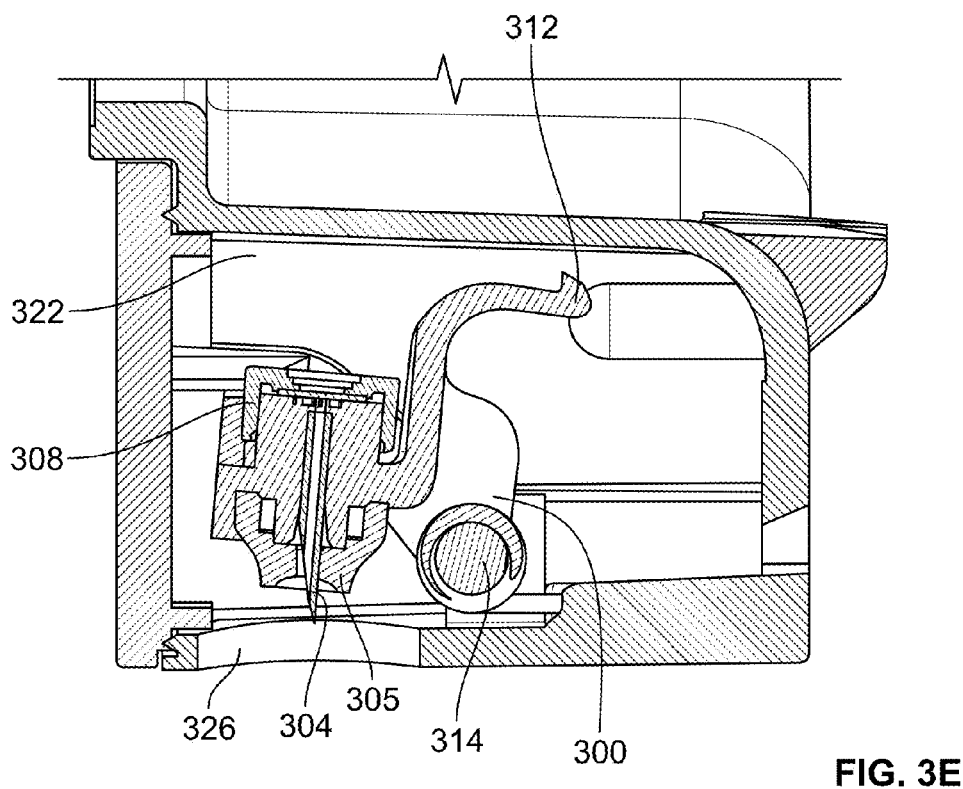

In the variation of sampling arrangement (300) described immediately above, hub (302) may be configured to rotate relative to a cartridge cell (322). FIGS. 3C-3E illustrate a method by which sampling arrangement may rotate relative to a cartridge cell (322). When positioned inside of cartridge cell (322), pivot bars (314) may engage one or more portions of the cell (322) such that the pivot bars (314) may rotate relative to the cartridge, but are otherwise held in place. As such, pivot bars (314) may act as a pivot point around which the rest of the sampling arrangement (300) may rotate. Indeed, the sampling arrangement (300) may rotate between a cocked/pre-fired position, an extended position, and a resting position, as shown in FIGS. 3C-3E, respectively. It should be appreciated that an imaging system of the meter may visualize or otherwise image one or more portions of the sampling arrangement (300) (e.g., pad (306)) when the sampling arrangement is in a stationary position, or as the sampling arrangement (300) moves between some or all of these positions.

When in a pre-fired position, the torsional spring (310) may be positioned such that it is compressed/wound, as shown in FIG. 3C. In this way, the spring may store energy that may later be used to drive the sampling arrangement (312). It should be appreciated that in some instances a spring may be stretched or bent instead of compressed. A latch (312) or similar structure may engage a portion of the cell (322), thereby temporarily locking the sampling arrangement (300) in place. During a testing procedure, a trigger mechanism or similar mechanism, as will be described in more detail below, may disengage latch (312) or otherwise release the sampling arrangement so that it is free to move. Torsional spring (310) may then decompress/unwind to rotate hub (302) around pivot bars (304). The hub may then rotate hub forward around the pivot point provided by the pivot bars (304) such that the sampling arrangement (300) enters an extended position, as illustrated in FIG. 3D.

In this position, the sampling arrangement may be positioned such that a needle (304) or other penetration member of the arrangement may pierce, penetrate or otherwise puncture a sampling site (not shown) to collect a fluid sample (not shown). In some instances, needle (304) may extend through an aperture (326) of cell (322) when in an extended position, but need not. Hub (302) may rotate back and forth harmonically, eventually coming to rest at a resting position, as shown in FIG. 3E. Because pivot bars (314) act as a pivot point around which the sampling arrangement may rotate, a needle (304) may follow a fixed path during rotation. Additionally, the sampling arrangement and/or cartridge may comprise one or more protrusions or other elements that may help limit return rotation of the hub (302), as will be described in more detail below. As shown in FIG. 3E, the needle (304) may be entirely contained within the cartridge cell (322) when in the resting position, which may help minimize the risk of accidental needle sticks following a testing procedure.

While sampling arrangement (300) is shown in FIGS. 3A-3E as being configured to rotate relative to the cartridge, it should be appreciated that the sampling arrangements described here may be configured to move in any suitable manner relative to the cartridge. For example, in some variations, a sampling arrangement may be configured to slide or otherwise move in a linear fashion relative to the cell. In some of these variations, a portion of the sampling arrangement (e.g., a hub) may comprise one or more protrusions (e.g., a protrusion similar to pivot bars (314) described above), which may be configured to slide or move within one or more tracks in the cartridge cell. The tracks may be straight to provide a linear path for the sampling arrangements, or may be curved/zig-zagged to provide for multi-dimensional movement of the hub. In some of these variations, the protrusions may have a non-circular or non-rounded cross-section profile (e.g., rectangular, square, or the like), which may allow the protrusion to slide within a track but may prevent rotation of the protrusion relative to the track. Additionally or alternatively, the sampling arrangement may comprise two or more protrusions disposed in a single track, which may also help to prevent rotation of the sampling arrangement relative to the cartridge. Conversely, it should be appreciated that the cartridge may comprise one or more protrusions/pivot bars, and the sampling arrangements may comprise one or more tracks which may slide along and/or rotate around the protrusions.

While sampling arrangement (300) is shown in FIGS. 3A-3E as comprising a torsional spring (310), it should be appreciated that the sampling arrangement (300) may be moved by any suitable mechanism during a testing procedure. For example, in some variations the sampling arrangements may comprise one or more springs (e.g., a torsional spring, a linear spring, a leaf spring, a conical spring or the like). In these variations, the springs may be held in a compressed or stretched configuration, the stored energy from which may act to slide, rotate, or otherwise move one or more portions of the sampling arrangement when released. In other variations, one or more one or more actuators may slide, rotate, or otherwise move the sampling arrangement relative to the cartridge. For example, in some variations a mechanically-driven arm may temporarily engage a portion of the sampling arrangement (e.g., the hub) to slide, rotate, or otherwise move the sampling arrangement.

As mentioned above, the sampling arrangements described here may comprise one or more penetration members for facilitating collection of a fluid sample. The penetration member may be any suitable structure capable of piercing, puncturing, or otherwise penetrating a sampling surface. For example, in some variations the penetration member may comprise a hollow needle or microneedle. The needle may have any suitable outer diameter (e.g., about 300-600 µm, about 500 µm, etc.) or gauge (20-25, 26-36, etc.), and any suitable inner diameter (e.g., about 25-250 µm). In some variations, the hollow needle may be configured to collect and transport a fluid sample through the bore of the needle. In some instances, the diameter of the bore is sufficiently small to draw fluid into the needle by capillary action. In other variations, the penetration member may comprise a solid lancet. In these variations, the lancet may comprise one or more channels/microchannels on a surface thereof for transporting a fluid along a surface thereof. The penetration members described here may be made of any suitable material or combination of materials (e.g., one or more metals, plastics, glasses, or the like), and may additionally comprise one or more coatings (e.g., polydimethylsiloxane, Silwet™, or the like) and/or surface texturing to help promote fluid flow relative to the penetration member. In some variations, one or more coatings may comprise heparin or another anticoagulant to help prevent blood from clotting in or on the penetration member.

As mentioned above, the sampling arrangement may comprise one or more standoffs, such as standoff (305) shown in FIGS. 3A-3E. The standoff may be attached to and/or at least partially circumscribe a portion of the penetration member (e.g., a needle or solid lancet). A standoff may serve a number of useful functions. In some variations, the standoff may act to help block light from entering a cartridge cell. For example, in the variation of sampling arrangement (300) described above, when sampling arrangement (300) is placed in an extended position or a resting position (as shown in FIGS. 3D and 3E respectively), the standoff (305) may at least partially block or cover aperture (326). In this way, standoff (305) may substantially prevent light from entering the cartridge cell, which may help to minimize stray light from entering the optical system of the meter. In some variations, standoff (305) may be made from a matte or light-absorbing material that helps prevent light from reflecting off standoff (305) into the cartridge.

In other instances, the standoff (305) may aid in collection of a fluid sample. Specifically, in some variations at least a portion of the standoff (305) may be concave. During a testing procedure, a user may apply a portion of a fluid sample to the concave surface of the standoff (305) (e.g., by milking a drop of blood onto the standoff). The fluid may naturally settle to the bottom of the concave surface, where it may enter a lumen (not shown) of needle (304). The standoff may further comprise one or more grooves or channels, and/or one or more hydrophobic coatings to help direct blood toward needle (304)

In still other instances, the standoff (305) may affect or control the depth and/or rate of penetration of a sampling site during a testing procedure. As the penetration member pierces a sampling site during a testing procedure, the standoff may engage the sampling site to prevent further advancement of the penetration member. It should be appreciated that in some instances, the depth of penetration will be naturally controlled and/or limited by the movement path of the sampling arrangement. In some variations, the standoff may act to limit the penetration depth of the penetration member. In some of these variations, the standoff may be made of a compressible material, which may compress against skin during penetration. This compression may help slow the penetration member as it penetrates a sampling site, which may help to reduce pain associated with the penetration of the penetration member. Additionally, energy stored in the compressed standoff may push against the sampling site, and may increase the speed at which the penetration member exits tissue. Additionally or alternatively, the standoff may be slidable relative to the penetration member. In these variations, the standoff may come into contact with the skin during penetration, which may cause the standoff to slide relative to the penetration member. One or more frictional forces that may result from the relative movement between the standoff and the penetration member may act to limit or resist forward movement of the penetration member. It should also be appreciated that contact between the standoff and the skin may stimulate a larger area of pressure-sensing neurons, which may inhibit the transmission of pain signals from pain-sensing neurons, thereby reducing pain associated with penetration.

In variations where a spring is configured to rotate the sampling arrangement relative to a cartridge, one or more portions of the sampling arrangement (e.g., the hub) and/or cartridge may be configured to limit the rotation of the sampling arrangement. In some of these variations, one or more portions of the sampling arrangement and/or cartridge may be configured to limit forward rotation of the sampling arrangement. In variations in which a sampling arrangement comprises a standoff, the standoff may help to limit and/or control the forward rotation of the hub, as described immediately above. In other variations, one or more portions of the hub may interact with a portion of the cartridge to limit and/or control forward rotation of the hub. Additionally or alternatively, in other variations, one or more portions of the sampling arrangement and/or the cartridge may prevent rearward rotation of the sampling arrangement. For example, in some variations, a sampling arrangement may comprise one or more stops that may interact with one or more protrusions or other portions of a cartridge cell to prevent rearward rotation beyond the point of interaction. Specifically, when a sampling arrangement is in the cocked position, a stop may bend or flex protrusion away from an initial configuration. When fired, the stops may temporarily disengage the protrusion, which may straighten or otherwise reconfigure to enter some or all of the space previously occupied by the stops. The protrusion may then block a portion of the return path of stops, thereby limiting rearward rotation. Additionally or alternatively, one or more of the stops may be bent or flexed when a sampling arrangement is in a cocked position, and may straighten after firing. Similarly, the return path of the unbent stops may be blocked by the cartridge protrusion to prevent rearward rotation. Although the sampling arrangement may be configured to have a limited range of rotation, the sampling arrangement may be configured to stop at a resting position at one of the rotational limits, or between the rotational limits (e.g., such that the penetration member comes to rest in or directly over the puncture wound. It should also be appreciated that in variations where a sampling arrangement is moved in a linear direction, the sampling arrangement and/or cartridge may be configured to limit and/or control this linear movement.

In some variations, the sampling arrangement may be configured to transfer the fluid sample from one portion of the sampling arrangement to another portion of the sampling arrangement. For example, in the variation of sampling arrangement (300) described above, a fluid sample captured by needle (304) may pass through a bore of the needle (e.g., by capillary action) to a micropatterned surface (316) of the hub (302). This surface (316) may comprise one or more grooves, channels, and or fluid pathways for drawing the fluid sample from the needle bore and spreading it across surface (316). These surfaces may help to provide quick and even wetting of a quantification member (e.g., pad (306)). For example, in some variations the sampling arrangement comprises a reagent/assay pad that is configured to react with the fluid sample. In some of these variations, the rate at which the fluid sample spreads across the pad may be slow relative to the reaction rate between the fluid sample and the reagent(s). As such, the reaction at one point of a pad may be complete before blood may reach another portion of the pad. In some instances, it may be desirable for the fluid sample to be spread across the reagent quickly, so as to allow the reaction to occur at a similar time in different portions of the pad. This may be desirable in instances where analysis of a fluid sample comprises measuring a rate of reaction between the fluid sample and the pad. A micropatterned hub surface may help to spread the fluid sample across the surface of a quantification member more quickly. In some variations (as will be described in more detail below), the micropatterned hub surface may be configured to spread fluid across the surface prior to contacting a quantification member. In some of these variations, the fluid sample may contact different portions of the reagent pad simultaneously. In others of these variations, the fluid sample may directionally wet the reagent pad (e.g., from one side of a quantification member to a different side of a quantification member).

As mentioned above, the surface may comprise one or more grooves, channels, and or patterned fluid pathways for drawing the fluid sample from the needle bore and spreading it across the surface. These fluid pathways may provide less resistance to fluid flow, and thus the fluid may travel along these paths, where they may be absorbed by different portions of the pad. Additionally, depending on the size and spacing, the fluid pathways may be configured to actively draw fluid by capillary action, which may increase the speed or degree to which the fluid is drawn from the needle. The patterned surface may comprise any suitable configuration. In some variations, the surface may comprise one or more grooves or channels, such as those described in U.S. patent application Ser. No. 11/239,123, titled "DEVICES AND METHODS FOR FACILITATING FLUID TRANSPORT," the content of which is hereby incorporated by reference in its entirety.

Figure 4:
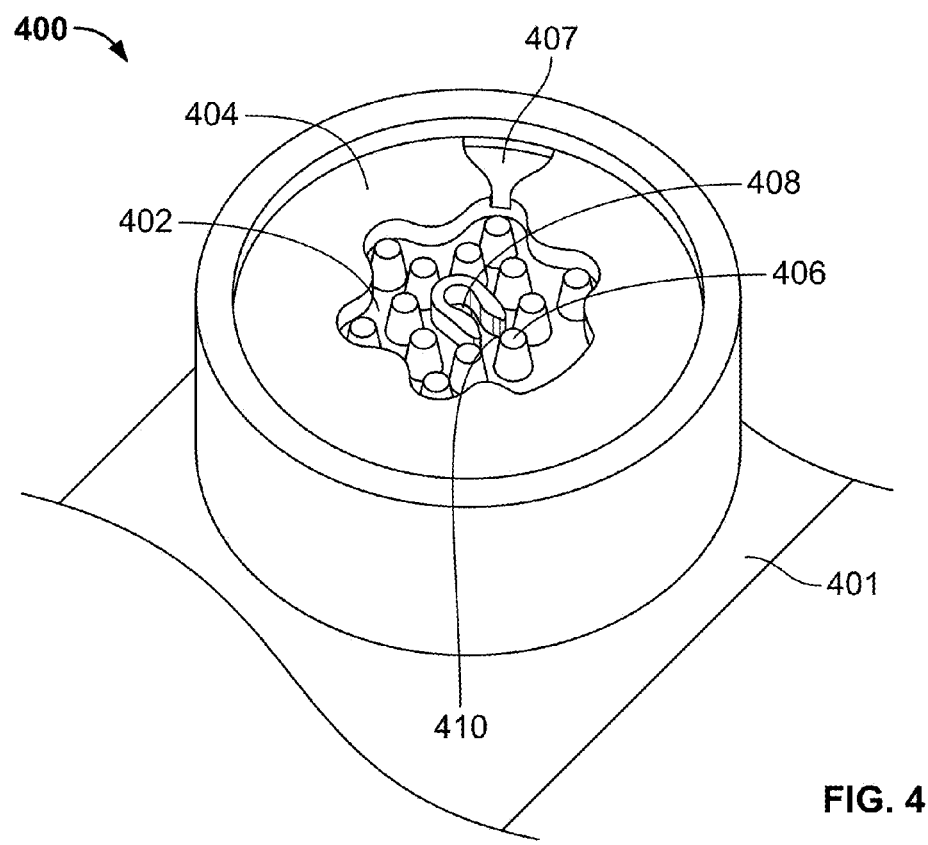
FIG. 4 illustrates one variation of a hub comprising a patterned surface suitable for use with the sampling arrangements described here.

FIG. 4 illustrates one variation of a sampling arrangement (400) comprising a hub (401) having a patterned surface. As shown there, hub (401) may comprise a lower surface (402), an upper surface (404), a plurality of posts (406) extending from the lower surface (402), and a channel (407) in the upper surface (404). When a quantification member (e.g., a reagent pad) is placed on hub (401), the quantification member (not shown) may rest on the upper surface (404) and/or the tops of posts (406). The posts (406) may be positioned such that spacing between the posts creates a capillary action that draws fluid from a fluid source (408) (e.g., the bore of a needle) from an inlet (410) and spreads the fluid across the lower surface (402). For example, in some variations the spacing between adjacent posts may be between about 0.002 and about 0.005 inches). The capillary action created by the posts creates a plurality of flow paths, and because these fluid flow paths are interconnected, blocking the space between two adjacent posts (406) (e.g., with the pad or other debris) may not substantially alter the ability of hub (401) to wick the fluid, as the sample may take one or more alternate paths to reach the same destination.

In some variations, the patterned surface may be configured to draw a certain amount of fluid into the patterned surface prior to contacting the fluid. For example, in the variation of patterned surface of hub (401) shown in FIG. 4, posts (402) may be of a sufficient height (e.g., about 0.005 inches) to allow fluid to spread across the lower surface (402) without contacting a quantification member (e.g., a reagent pad). Once the fluid sample has spread across the lower surface (402), the fluid level may rise until it reaches the level of the quantification member. At this point, the fluid sample may contact different portions of the quantification member substantially simultaneously, which may result in a more consistent and easily-measured reaction. Additionally, in some variations, lower surface (402) may be configured to collect a certain volume of fluid (e.g., an amount sufficient to complete a reaction with the quantification member) before the fluid contacts the quantification member. If an insufficient sample size is collected, fluid will not reach the quantification member (and thus no reaction will occur), at which point the meter may be configured to alert the user to apply additional fluid to the sampling arrangement.

As shown in FIG. 4, the fluid source (408) may be centrally positioned relative to the lower surface (402). In these variations, the fluid may be configured to spread out in a radial manner. In other variations, the fluid source may be located toward one end of the surface, and may be configured to draw fluid directionally away from the fluid source. The patterns described above may be formed in any suitable manner, such as, for example, molding, laser ablation, electrode-discharge machining, etching, or another suitable micro-machining technique. Additionally, the micropatterned surface may comprise one or more coatings, such as, for example, a heparin coating, a surfactant coating, a wetting agent, combinations thereof, or the like.

When a quantification member is placed over a patterned surface, gas may be trapped under the quantification member such that it is contained within the flow paths of the patterned surface. As a fluid sample is introduced to the patterned surface via a fluid source (e.g., the bore of a needle, as describe above), this trapped gas may impede the capillary action of otherwise affect the fluid flow along one or more flow paths of the patterned surface, which may further affect the ability of a fluid sample to reach and react with the quantification member. Accordingly, in some variations of the devices described here, one or more portions of the pattern surface may be fluidly connected to one or more vents or gas-collection regions. For example, in the variation of hub (401) described above in relation to FIG. 4, channel (407) in the upper surface (404) provide a flow path into which trapped gas may be pushed as fluid spreads across the lower surface (402). In some of these variations, gas may be able to pass through channel (407) and out of the sampling arrangement (400). For example, in some variations when a cap (not shown) is placed over the quantification member to hold it in place, the cap may be configured such that gas may flow from the patterned surface, through the channel, and past the cap (e.g., through one or more channels or holes in the cap, or through a space between the hub and the cap). In other variations, gas may not be able to travel past the cap, and thus gas may be collected in channel (407).

It should be appreciated that while shown in FIG. 4 as having a single channel (407), the hub (401) may comprise any suitable number of channels (e.g., zero, two, three, or four or more). Variations with multiple channels may find particular utility in instances where one or more channels becomes clogged by debris or is otherwise blocked such that gas cannot be collected therein and/or flow therethrough.

Additionally, while shown in FIG. 4 as having one fluid inlet (410) connected to the fluid source (408), the hub (401) may comprise any suitable number of inlets FIGS. 22A and 22B depict a perspective view and a top view, respectively, of a portion of a variation of a sampling arrangement (2200) comprising a hub (2202). As shown there, hub (2202) may comprise a patterned surface having a lower surface (2201), an upper surface (2203), and comprising a plurality of posts (2204), first (2206) and second (2208) fluid inlets connected by flow diverters (2210), and channels (2212). The first (2206) and second (2208) inlets and flow diverters (2210) may surround a bore (2214). The bore (2214) may be fluidly connected to a skin-penetration member, such that a fluid sample collected by the skin-penetration member may be delivered to the bore (2214). The flow diverters (2210) may be constructed and positioned such that the diameter of the bore increases between the lower surface (2201) and upper surface (2203). As the diameter of the bore increases, the capillary forces created by the bore (2214) decrease, which may promote the lateral spread of fluid. By promoting lateral spread of fluid, the hub may be configured to collect a certain amount of fluid prior to the fluid level reaching a quantification member (such as a reagent pad). Similarly, the first and second fluid inlets may get wider between the lower surface (2201) and the upper surface (2203), which may also promote the lateral spread of fluid. As described in more detail above, the posts (2204) may be positioned relative to the first (2206) and second (2208) fluid inlets to provide capillary flow around the posts (2204), such as described in more detail above. In some variations, the posts (2204) may decrease in diameter between the lower surface (2201) and upper surface (2203) which may promote lateral flow as described immediately above.

FIGS. 17A and 17B depict a perspective view and a top view, respectively, of a portion of another variation of a sampling arrangement (1700) comprising a hub (1702). As shown there, hub (1702) may comprise an upper surface (1704), a bore (1706), a plurality of fluid channels (1708) and flow diverters (1701). As shown there, each fluid channel (1708) may be positioned between two adjacent flow diverters (1701) and may include a ramped surface extending between the bore (1706) and the upper surface (1704). The fluid channels (1708) may provide capillary forces to draw fluid from the bore (1706) and deliver it to a quantification member (e.g., a reagent pad) that can be positioned over the fluid channels (1708) and flow diverters (1701) and rest at least partially on the upper surface (1704). The fluid channels (1708) may increase in width between the bore (1706) and the upper surface (1704) (as the fluid channel (1708) becomes shallower). As the width of the channel (1708) increases, the capillary forces provided by the channel (1708) may decrease. This may encourage each of the fluid channels (1708) to fill equally, which may result in a more uniform delivery of fluid to the quantification member.

In the variation of hub (1702) shown in FIGS. 17A and 17B, the flow diverters (1701) may include a first plurality of flow diverters with upper surfaces (1710) that are parallel with the upper surface (1704) of the hub (1702) and a second plurality of flow diverters with upper surfaces (1710) that are angled downward toward the bore (1706). The quantification member (not shown) may rest on the upper surfaces (1710) of the first plurality of flow diverters (which may help prevent the quantification member from bowing in towards bore (1706), while the second plurality of flow diverters may allow fluid to reach a larger area of the reagent pad. It should be appreciated, however, that in some variations the upper surfaces (1710) of each of the flow diverters (1701) may be parallel to the upper surface (1704) of the hub (1702), while in other variations the upper surfaces (1710) of each of the flow diverters (1701) may be angled toward the bore (1706).

As mentioned above, the sampling arrangements described here may comprise one or more quantification members for reacting with a fluid sample to provide a measurable result. The quantification member may be configured for electrochemical or photochemical reactions with the fluid samples. For example, in some variations, the sampling arrangement may comprise one or more reagent/assay pads, such as pad (306) depicted in FIG. 3B above. These pads may be made from one or more absorbent materials (e.g., nitrocellulose), which may contain one or more chemical reagents for reacting with the fluid sample. These chemical reagents may react with the fluid sample to produce one or more measurable parameters (e.g., a color change, an electrochemical response, or the like), which may be detected and/or measured by one or more portions of the meter. In variations where the quantification member is configured to produce a photometric response, the quantification member may be imaged using one or more imaging systems, as will be described in more detail below. In variations where the quantification member is configured to produce an electrochemical response, the sampling arrangement may comprise one or more electrodes for measuring or otherwise quantifying the electrochemical response. Additionally, it should be appreciated that any suitable photometric or electrochemical quantification member or members may be used with the sampling arrangements described here.

As mentioned briefly above, a cap or other holding structure may be used to hold the quantification member in place relative to the hub. For example, in sampling arrangement (300) described above in relation to FIGS. 3A-3E, cap (308) may hold pad (306) against micropatterned surface (316) of hub (302). As shown there, the cap (308) may comprise an aperture (318) through which the pad (306) may be viewed using one or more imaging systems, such as will be described in more detail below. This may provide particular utility in instances where is may be desirable to optically image a quantification member. While shown in FIG. 3B as having an aperture (318), the cap (308) may additionally or alternatively comprise one or more viewing windows made from a transparent material.

The caps described herein may engage a hub in any suitable manner. In some variations, the cap may be integrally formed as a part of a hub (e.g., may be formed as a flip-top lid associated with the hub). In other variations, the cap may be press fitted against a hub. In still other variations, cap may be attached to hub via one or more latches or other attachment mechanisms. In some variations, when a cap is attached to a hub, the cap may be configured to compress at least a portion of a quantification member between the cap and the hub. This compression of the quantification member may affect the member's ability to draw in or otherwise react with a fluid sample. In variations where the cap comprises a viewing window, the portion of the quantification member overlaid by the viewing window may not be compressed, and thus that portion of the quantification member may not be affected by compression. In this way, compression of an unviewed portion or portions of a quantification member may limit the fluid absorbed by the unviewed portion or portions. In variations where the cap is press fit against the hub, the cap may be adjustably pressed against the hub to adjustably compress the quantification member.

Figure 5A:
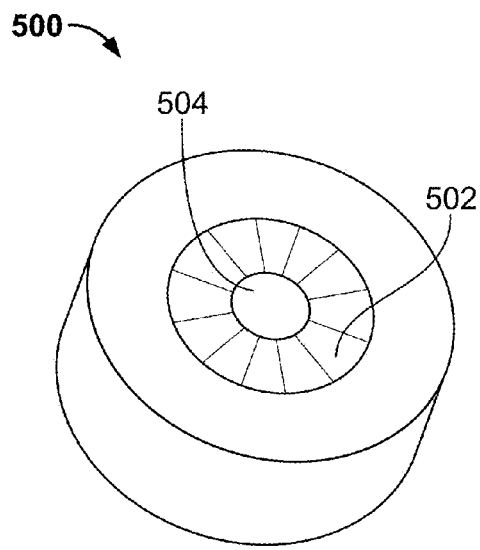
FIGS. 5A-5C illustrate different variations of caps suitable for use with the sampling arrangements described here.
Figure 5B:
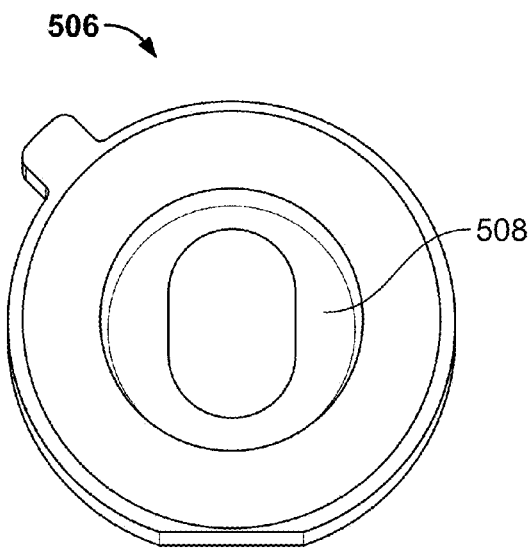
Figure 5C:
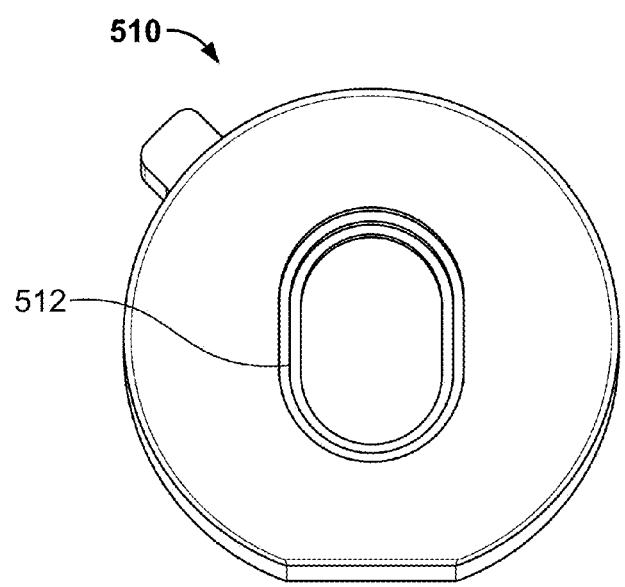

In some variations where the sampling arrangement is configured to be viewed by an imaging system, as will be described below, the cap may comprise one or more light-altering features for deflecting, absorbing or capturing stray light (e.g., stray light generated by the light source, or stray light reflected by a quantification member). FIGS. 5A-5C illustrate different variations of caps suitable for use with the sampling arrangements described here. As shown in FIG. 5A, cap (500) may comprise a tapered recess (502) surrounding aperture (504). The tapered recess (502) may act to deflect or catch stray light. While shown in FIG. 5A as being linearly tapered, the tapered recess may also follow one or more curves. For example, FIG. 5B shows another variation of cap (506) comprising a curved, tapered recess (508). Additionally or alternatively, the tapered recess may comprise one or more steps. For example, FIG. 5C shows a variation of cap (510) comprising a plurality of tapered steps (512).

Additionally, in some variations, a cap may be made of a colored material that may act as a reference color for an imaging system of the meter housing. In some variations, an optical system may use the color of the cap to calibrate color or brightness readings taken by the imaging system (e.g., by determining if the measured color of the cap is different than expected). Additionally or alternatively, the color of the cap may allow for an imaging system to identify the boundary between the cap and the quantification member. This boundary may be used as a reference position when visualizing the quantification member.

It should be appreciated that the sampling arrangements may comprise any elements or combination of elements with any suitable feature or features, such as those described above.

Meter Housing

The meters described here may comprise a meter housing. Generally, a meter housing may accept/receive one or more cartridges, such as those described in more detail above, allowing the meter to provide all of the components necessary to perform a testing procedure (e.g., collection, transport, and analysis of a fluid sample). As noted above, the meter housing may be configured to be disposable, or may be configured to be reusable (e.g., configured for use with multiple cartridges). The meter housing may be configured for handheld use, but also may be configured to temporarily attach to the body as a wearable meter. For example, in some variations the meter housing may comprise one or more straps (e.g., such as a wrist band) or other body-attachment elements.

Figure 6C:
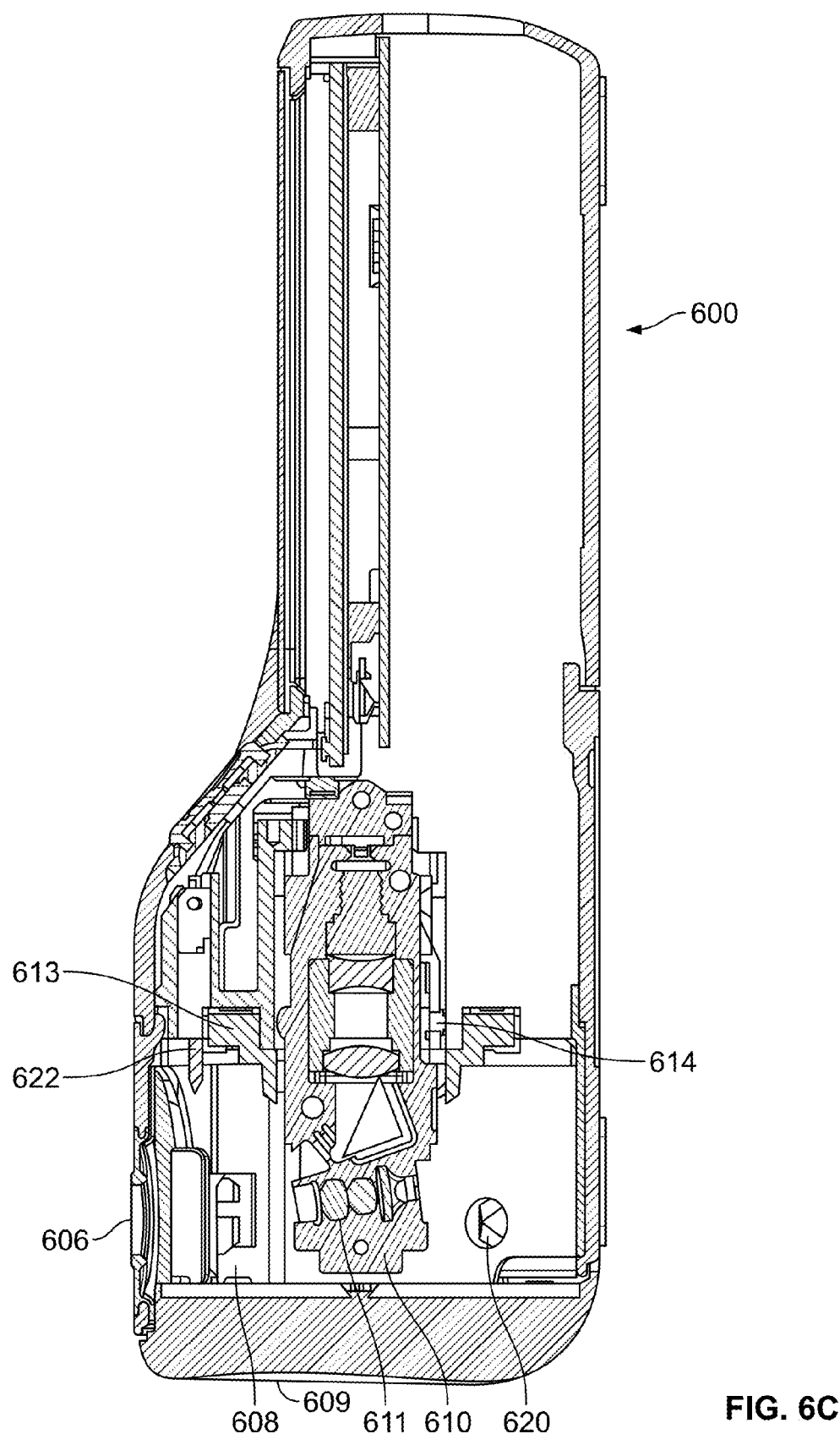
Figure 6D:
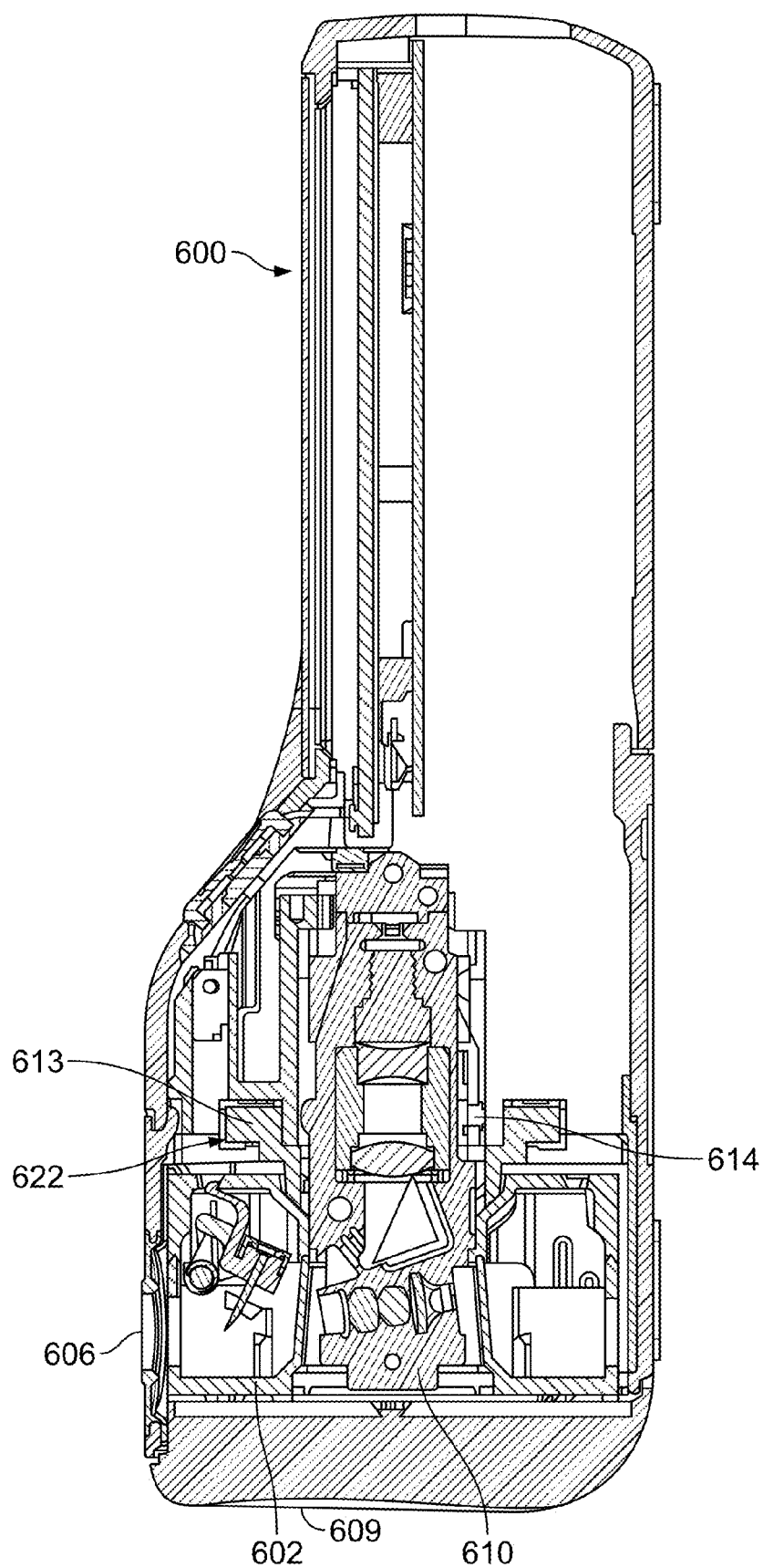

FIGS. 6A-6D illustrate one variation of a meter housing (600) suitable for use with the meters described here. Specifically, FIGS. 6A-6C show a front view, a partial cross-sectional front view, and a cross-sectional side view, respectively, of meter housing (600). FIG. 6D shows a cross-sectional meter housing (600) engaging a cartridge (602). As shown there, meter housing may comprise a display (603), button (604), port (606), cartridge-receiving chamber (608), door (609), tower (610) carrying optical system (611) and light source (612), rotating element (613), activation mechanism (614), barcode reader (616), light detector (618), foil punch (620), and trigger mechanism (622). The various components of meter housing (600) may aid in the operation of the meter, and each will be described in more detail below. Although not shown in FIGS. 6A-6C, the door (609) may comprise one or more cartridge-engagement projections, such as described in more detail above.

The meter housings described here may comprise one or more displays, such as display (603) shown in FIG. 6A.

Display (603) may be used to communicate information (e.g., battery/power information, testing results, number of available test sites, reminders/alarms, and the like) to a user. Additionally or alternatively, information may be conveyed to a user via one or more sounds or audio alerts, and/or one or more tactile alerts (e.g., a vibrational alert or the like). For example, in some variations the meter housing may comprise one or more speakers configured to relay audio information to a user (e.g., via spoken prompts or data broadcasts).

The meter housings described here may also comprise one or more buttons, levers, switches, sensors or other structures for operating the meter. For example, meter housing (600) shown in FIG. 6A may comprise a button (604). It should be appreciated that the meter housing (600) may comprise any suitable number of buttons (e.g., zero, one, two, three, or four or more). These buttons (or other structures such as those mentioned above) may be configured to serve any suitable function. In some instances, one or more buttons may be configured to turn the meter on or off, wake the meter from a hibernating state, or place the meter in a hibernating state. In other instances, one or more buttons may be used to call up information from the meter (e.g., previous testing results, information relating to the cartridge, or the like) which may be displayed on a display and/or aurally communicated. In still other instances, a button or buttons may be used to input information into the meter (e.g., calibration codes, date information, or the like), which may be stored in a memory component of the meter housing or cartridge. In still other variations, one or more buttons may be used to authenticate a particular user, as described in more detail below. Additionally or alternatively, one or more buttons may be used to initiate a testing procedure, as will be described in more detail below. It should be appreciated that one button (or a number of buttons) may serve a number of functions, such as a combinations of the actions described immediately above. Additionally, it should be appreciated that these actions may be achieved through any suitable device or structure (e.g., one or more levers, switches, toggles, touch screens, sensors, combinations thereof, and the like).

The meter housing may comprise memory or other internal circuitry for storing information (e.g., testing results, calibration codes, testing protocols, or the like). In some variations, the meter housing may be configured to transmit data to or otherwise communicate with one or more external components (e.g., a computer, a server, or the like), thereby allowing the meter to upload or otherwise transfer data (e.g., testing data) stored in the meter housing. This data may then be analyzed (manually or automatically), and may allow a user, physician or healthcare provider to evaluate the effectiveness of a given treatment, drug, diet, or exercise regime in managing one or more conditions (e.g., diabetes) of a patient. Additionally, the meter housing may be configured to download information or data (e.g., date and time information, calibration codes, sampling protocols, software updates, hardware updates, or the like) from an external source. In some variations, the meter housing may comprise a communication or data port (e.g., a USB port, a firewire port, or the like) for direct connection to a computer or other device. In other variations, the meter housing may be configured to wirelessly transmit and/or receive information from an external source, as described in U.S. patent application Ser. No. 12/457,332 and titled "MEDICAL DIAGNOSTIC DEVICES AND METHODS," the content of which is hereby incorporated by reference in its entirety. In still other variations, the meter may comprise a memory card reader. In these variations, a user may place a memory card or chip into the reader to provide data or information to the meter housing. In some instances, the memory card may contain information specific to a particular cartridge, such as calibration codes and/or expiration information.

As illustrated in FIGS. 6A and 6C, meter housing (600) may comprise one or more ports (606). Generally, a port (606) may provide an opening (624) in the meter housing (600) through which a fluid sample may be collected by a sampling arrangement of a cartridge. For example, a user may place one or more skin surfaces (e.g., a portion of a finger, palm, toe, arm, leg, stomach, or the like) or other sampling sites (e.g., a portion of a vial of control fluid) against port (606) and may initiate a testing procedure (in some instances, placing a sampling site against the port (606) may initiate the testing procedure). During the testing procedure, a penetration member of a sampling arrangement (not shown) may be driven through the opening (624) in port (606) to pierce or otherwise puncture the sampling site. Additionally or alternatively, one or more portions of the sampling site may be pressed through the opening (624), where it may be pierced by the sampling arrangement.

Port (606) may comprise any suitable structure or structures, such as one or more of the arrangements described in U.S. patent application Ser. No. 12/457,085, titled "BODY FLUID SAMPLING DEVICE—SAMPLING SITE INTERFACE," the content of which is hereby incorporated by reference in its entirety. For example, in some variations, such as meter housing (600) illustrated in FIGS. 6A and 6C, port (606) may comprise a flexible ring (626) which may flex, bend, or otherwise move when a force is applied to the port (606). These variations may find particular utility in instances where it is desirable to transmit a force via a port to another portion of the meter (e.g., a cartridge or tower), as will be described in more detail below.

One or more cartridges (602) may be placed inside the meter housing (600) via cartridge-receiving chamber (608). Specifically, door (609) of meter housing (600) may be opened to provide access to cartridge-receiving chamber (608), and cartridge (602) may then be inserted therein. The door (609) may then be closed to hold cartridge (602) in place, as shown in FIG. 6D. The meter housing may comprise one or more structures for aligning, engaging and/or holding the cartridge in place relative to the meter housing (600). For example, tower (610) may align or hold the cartridge in place relative to one or more portions of the meter housing (600). For example, in variations where tower (610) houses an imaging system (611), tower (610) may hold cartridge (602) in place relative to the imaging system (611) (e.g., via engagement between the cartridge (602) and one or more portions of the door (609), as will be described in more detail below.

The meter housings described here may comprise one or more rotation elements, which may be used to rotate a cartridge relative to one or more portions of the meter assembly. For example, in the variation of meter housing (600) shown in FIGS. 6A-6D above, meter housing (600) may comprise a rotation element (613) that is rotatable relative to the tower (610). Rotation element (613) may comprise teeth (624), cogs or other structures that may engage corresponding teeth, cogs, or similar structures of a cartridge (e.g., teeth (209) of cartridge (200) describe in more detail above in relation to FIGS. 2A-2D). Thus, when a cartridge (602) is placed within meter housing (600), as shown in FIG. 6D, engagement between the rotation element (613) and the cartridge (602) may cause the cartridge (602) to rotate as rotation element (613) is rotated relative to the meter housing (and tower (610)). Rotation of the cartridge (602) may aid in indexing the cartridge, as will be described in more detail below, and/or may place a new sampling arrangement in position for use with a testing procedure.

In some variations, a rotation member may aid in aligning a cartridge (e.g., cartridge (602)) relative to a meter housing. For example, in the variation of meter housing (600) described above with relation to FIGS. 6A-6D, when a cartridge (602) is pushed or otherwise inserted into a cartridge-receiving chamber (608), the ramped portions (625) of teeth (624) may slide along corresponding ramped portions of teeth (not show) of the cartridge (602), which may act to rotate and self-align the cartridge (602) relative to the rotation element (613). This self-aligning feature may reduce the dexterity needed to properly position a cartridge (602) relative to the rotation member. While rotation element (613) described above may rotate and align the cartridge, it should be appreciated that in other instances, separate mechanisms are used to rotate and align the cartridge. In still other variations, the meter housing may comprise an alignment mechanism without a rotation mechanism.

When a testing procedure is initiated, it may be necessary to trigger, activate, release, or otherwise move a sampling arrangement in order to collect a fluid sample. As such, the meter housing may comprise one or more trigger mechanisms for activating a sampling arrangement. In variations where a sampling arrangement is configured to be moved by a spring, the triggering mechanism may be configured to release the spring from a stretched, compressed, wound, or otherwise constrained position. In other variations, the triggering mechanism may at least temporarily engage a portion of the sampling arrangement to move between one or more positions (e.g., between a pre-firing position and an extended position).

Trigger mechanism may be any suitable mechanism, such as those described in U.S. patent application Ser. No. 11/529,614, which was previously incorporated by reference. FIGS. 8A-8C illustrate one suitable variation of a trigger mechanism (800) suitable for use with the meters described here. Specifically, FIGS. 8A-8C show a cross-sectional side view of a cartridge cell (802) and trigger mechanism (800) comprising a two-part activation member (804). As shown there, activation member (804) may comprise a vacuum tube (805) and a trigger pin (806), both attached to a base member (808). The activation member (804) may be attached to and/or moved by the meter housing (not shown). Specifically, vacuum tube (805) and trigger pin (806) may be simultaneously advanced or withdrawn via base member (808) by one or more actuation mechanisms, and may enter a cartridge cell (802) to facilitate a testing procedure. For example, activation member (804) may be moveable between three or more positions. In a first "pre-fired" position, the entirety of activation member (804) may be external to cell (802), as shown in FIG. 8A. Upon activation of a testing procedure, the activation member (804) may be moved to a second position, in which a portion of the vacuum tube (805) enters and at least partially extends into cell (802) through an aperture (810) in a wall of the cell (802). As activation member (804) moves into the second position, it should be appreciated that the vacuum tube (805) may pierce or otherwise puncture a covering material (not shown) overlying the aperture (814).

Once in the second position, vacuum tube (805) may be connected to a vacuum pump and may apply vacuum pressure to cell (802). By applying vacuum pressure to the cell (802), the vacuum tube (805) may apply vacuum pressure to a skin surface in engagement with the cell (802). After a sufficient level of vacuum has been applied to the cell (802), the activation member (804) may then be moved to a third "firing" position. In this position, trigger pin (806) may enter and at least partially extend into cell (802). As trigger pin (806) enters cell (802), trigger pin (806) may engage and move one or more portions of the sampling arrangement (816), such as latch (818) of hub (820). This may release latch (818), allowing a spring (824) to move sampling arrangement (816) relative to cell (802), as shown in FIG. 8C. The activation member (804) may then be returned to its first position, and a new cell (from the same cartridge, or a different cartridge) may be placed in alignment with the activation member (804), such that the activation member (804) may trigger another sampling arrangement.

While both vacuum tube (805) and trigger pin (806) shown in FIGS. 8A-8C are moved by base member (808), it should be appreciated that the vacuum tube (804) and trigger pin (806) may be actuated separately. In some variations, the vacuum and trigger pins may be moved independently of one another. In still other variations, the activation member comprises a single member that acts as both a vacuum tube and a trigger pin. In these variations, the single member may be moved from a first position outside of the cartridge to a second position where the member extends partially into the cartridge. In this position, the member may apply a vacuum to the cartridge. The member may then be moved to a second position inside of the cartridge (e.g., may be advanced further into in the cartridge) to trigger a sampling arrangement. For example, the trigger mechanism (107) shown in FIGS. 1A-1D and the triggering mechanism (622) shown in FIGS. 6A-6D may each comprise a member that acts as both a vacuum tube and a trigger pin, as described immediately above.

In some variations, the meter housing may comprise one or more barcode readers, but need not. For example, in the variation of meter housing (600) described above in reference to FIGS. 6A-6D, meter housing may comprise a barcode reader (616). In variations in which the cartridge comprises one or more barcodes on a surface thereof, barcode reader (616) may be configured to scan or otherwise read information contained in the barcode. When the cartridge is configured to be rotated (e.g., via rotation element (613)) or otherwise moved relative to the meter housing (600), the barcode reader may scan the barcodes as the cartridge is rotated or otherwise moved.

Additionally, in some variations, the meter housing may comprise one or more elements for puncturing, separating, moving or otherwise removing one or more portions of a covering material from a cartridge. In some variations, such as meter housing (600) shown in FIGS. 6A-6D and described in more detail above, meter housing (600) may comprise a punch (620). Punch (620) may be advanced into a cartridge cell via one or more apertures (not shown) to break, cut, remove or move the covering material (not shown) overlying the aperture. A sampling arrangement may then be advanced through the uncovered aperture to collect a fluid sample from a sampling site.

Also shown in FIG. 6B are light source (612) and light detector (618). Light source (612) may be configured to direct light in the direction of light sensor (618), and may be any suitable light source, such as those described hereinthroughout. Light detector (618) may be configured to measure the light at a given point inside of the meter housing (e.g., within the cartridge-receiving chamber). When a cartridge (602) is placed inside of the meter housing (600), as shown in FIG. 6D, the light source (612) and light detector (618) may help check the integrity of the cartridge, as will be described in more detail below.

Tower

As mentioned immediately above, the meter housings described here may comprise one or more towers or other structures for aligning or holding a cartridge in place relative to a meter housing. In variations of meter housings that do comprise a tower, the tower may be fixed relative to the meter housing, or may be movable relative to the meter housing. In variations where the tower is moveable relative to the meter housing, the tower may be moveable in any direction or directions relative to the tower. In some variations, the tower may be moveable in a lateral direction relative to the longitudinal axis of the meter housing. Additionally or alternatively, the tower may be configured to rotate relative to the longitudinal axis of the meter housing. Additionally or alternatively, the tower may be configured to rotate around the longitudinal axis of the meter housing.

FIGS. 7A and 7B show one way in which a variation of tower (700) may be configured to both move axially to and rotate relative to a longitudinal axis (702) of a meter housing (not shown). Specifically, FIG. 7A shows a front view of tower (700), while FIG. 7B shows a side view of tower (700) engaging with cartridge (703). Only a cross-section of cartridge (703) is shown in FIG. 7B, and cartridge (703) may comprise one or more sampling arrangements (705) such as those described in more detail above. As shown in FIGS. 7A and 7B, tower (700) may be rotatably coupled to a pin (704) or another linearly moveable element. Pin (704) may be slidably attached to a meter housing (not shown), such that the pin may slide axially relative to the meter housing. Due to the engagement between pin (704) and tower (700), when pin (704) slides along axis (702), tower moves along the axis (702). The pin (704), and with it tower (700) may move along any suitable axis or axes of the meter housing (e.g., a longitudinal axis of the meter). Tower (700) may also rotate around pin (704), as illustrated by arrow (722). It should be appreciated that in some instances, tower (700) may be fixedly attached to or otherwise integrated with pin (704), and both the pin (704) and tower (700) may be configured to rotate relative to a meter housing (not shown). This rotation may help initiate one or more testing procedures, as will be described in more detail below.

The towers described here may engage one or more cartridges to hold the cartridges in place relative to the meter housing. In some instances, the tower may hold the cartridge in a fixed relation relative to the entire meter housing. In variations where the tower is moveable relative to the rest of meter housing, the cartridge may be held in a fixed relation relative to the tower, and may be moveable relative to the rest of the meter housing. The towers described here may engage a cartridge in any suitable manner. In some variations, one or more portions of the tower may be configured to fit inside of one or more recesses of a cartridge.

The variation of tower (700) shown in FIGS. 7A and 7B shows one way in which the towers described here may engage a cartridge. As shown there, the distal portion of tower (700) may comprise a first section (706) and a second section (708) extending from the first section (706). First (706) and second (708) sections may be configured to extend into a recess (710) of cartridge (703) to engage the cartridge (703), as shown in FIG. 7B. In the variation of cartridge (703) shown there, recess (710) may comprise a first portion (712) having a first cross-sectional area and a second portion (714) having a second cross-sectional area. At least a portion of the first section (706) of the tower (700) may have the same exterior dimensions and/or cross-sectional shape (e.g., circle, oval, rectangular, square, or the like) as the first cross-sectional area of the first portion (712) of the recess (710). Additionally or alternatively, at least a portion of the second section (708) of the tower (700) may have the same exterior dimensions and/or cross-sectional shape (e.g., circle, oval, rectangular, square, or the like) as the second cross-sectional area of the second portion (714) of the cartridge (703). By matching the exterior of the tower (700) to the interior of the cartridge recess (710), placement of the tower into recess (710) may create a fit between the components that minimizes movement of the cartridge (703) relative to tower (700). It should be appreciated that in some instances (e.g., when tower (700) and recess (710) each have circular cross-sections), the cartridge (703) may be rotated relative to the tower (700), as will be described in more detail above. Additionally, while shown in FIGS. 7A and 7B as having first (706) and second (708) sections, it should be appreciated that the tower (700) may comprise any suitable number of sections (e.g., zero, one, two, three or four or more sections).

In some instances, the tower may comprise one or more mechanisms for limiting or otherwise preventing axial movement between cartridge and tower. For example, in some variations, one or more sections of the tower may affect axial movement relative to a cartridge. For example, in the variation of tower (700) described above, the second section (708) of tower (700) may have a smaller diameter than the first section (706) of tower (700). The second portion (714) of the cartridge recess (710) may have a diameter smaller than that of the first section (706) of the tower (700), but at least as large as the second section (708) of the tower (700). Accordingly, cartridge (703) may slide along tower (700) in the direction illustrated by arrow (716), until second section (708) of tower (700) enters second portion (714) of cartridge recess (710). Since the second portion (714) of the recess (710) is not large enough to accept the first section (706) of the tower (700), these portions may abut to prevent further axial movement toward the top of tower (700).

Additionally, one or more portions of the meter housing may prevent the cartridge (703) from disengaging from tower (700). For example, a spring (not shown) or other structure may bias or push tower (700) in a direction illustrated by arrow (718). Tower may push into recess (710) until the first section (706) of the tower (700) abuts the second portion (714) of the recess (710), which may in turn push or bias cartridge (703) in direction (718). One or more internal surfaces of the meter housing (e.g., a door or wall of a cartridge-receiving chamber) may act as a stop to block movement in direction (718). As such, the tower (700) may hold the cartridge (703) against the internal surface of the cartridge, holding the cartridge in place and preventing the cartridge (703) from disengaging the tower (700).

When cartridge (703) is held in place relative to tower (700), one or more forces may be applied to the cartridge (703) to move the tower (710) relative to the meter housing (not shown). For example, in some instances, a user may apply a force (represented by arrow (720)) to cartridge (e.g., via port)) as illustrated in FIG. 7B. This force may cause the cartridge (703) and tower (700) to rotate around pin (704) in the direction illustrated by arrow (722). This rotation may cause tower (710) to engage an activation element (724), which may in turn initiate a testing sequence, as will be described in more detail below.

As mentioned above, although a cartridge may be held in place axially and laterally relative to a tower, the cartridge may still be configured to rotate around the tower. In some variations, one or more mechanisms may be used to rotate the cartridge relative to the tower (or vice versa), as will be described in more detail below. In other variations, the cartridge may be unable to rotate relative to the tower (e.g., when both the tower and the cartridge recess comprise non-circular cross-sections). These variations may be useful in variations where an imaging system is housed separately from the tower within a meter housing. In some of these variations, one or more portions of the tower may be configured to rotate relative to the meter housing, thereby rotating the cartridge relative to the meter housing. For example, in variations where the tower is connected to the meter housing via a pin (e.g., such as tower (700) and pin (704) described above in relation to FIGS. 7A and 7B), the pin (or a portion of the meter housing holding the pin) may be configured to rotate the tower and cartridge within the meter housing. Additionally or alternatively, the tower may be divided into different segments, wherein a first segment may be configured to rotate relative to one or more other segments.

As mentioned above, a meter housing may comprise one or more activation elements for initiating a testing procedure. In some variations, an activation element may be any suitable switch or sensor capable of responding to one or more forces (or other stimuli) applied thereto. Any portion of the meter may apply a force to the activation element to initiate a testing procedure. For example, in variations where the tower is moveable relative to the meter housing, the tower may apply a force to the activation element. For example, in the variation of tower (700) shown in FIGS. 7A and 7B and described in more detail above, rotation of tower (700) around pin (704) (e.g., by application of force (720) to cartridge (703)) may press tower (700) into activation element (722). Alternatively, the activation element (722) may be positioned such that rotation of tower (700) around pin (704) may cause cartridge (703) to move into contact with the activation element (722). In still other variations, one or more activation elements may be incorporated into a port, such that when application of a force (e.g., via one or more sampling sites) to the port applies a force to the activation element. It should also be appreciated that in some variations, the meter housing need not comprise an activation element, and a testing procedure may be initiated in some other manner (e.g., by pressing one or more buttons) as will be described in more detail below.

The activation element may be any suitable structure. For example, the activation element may comprise one or more force sensors. In variations where the activation element comprises a force sensor, the force sensor may be configured to activate a testing procedure when the force within a certain range is applied thereto. In some instances it may be desirable to ensure that a user is pressing against the port with at least a minimum force level. For example, placing a skin surface against a port with a force greater than about 200 gram-force may help to increase blood flow to the area. As such, the force sensor may be configured to initiate a testing sequence once the force applied thereto indicates that the force applied to the port reaches a predetermined minimum level. Additionally, it may be desirable to set a maximum force level that will initiate a testing procedure. For example, if a skin surface is applied to a port with too high of a force (e.g., greater than about 500 gram-force) the increased pressure between the skin surface and the port may force blood away from the sampling site. Thus, in some variations, a force sensor will not initiate a testing sequence if the force applied to the force sensor is above a certain level. It should be appreciated that the force sensor may be configured to initiate a testing sequence in any suitable force range applied to the port (e.g., at least about 100 gram-force, at least about 200 gram-force, at least about 300 gram-force, between about 100 gram-force and 700 gram-force, between about 100 gram-force and about 600 gram-force, between about 200 gram-force and about 500 gram-force, between about 250 gram-force and about 450 gram-force, or the like). Any suitable force sensor may be used. In some variations, the force sensor may comprise one or more analog sensors or may comprise one or more digital sensors. In some variations, the force sensor comprises a force sensitive resistor.

In other variations, the activation element may comprise one or more switches. In these variations, a certain force applied to the switch may cause the switch to toggle/flip. The toggling of the switch may initiate one or more testing procedures. The force required to toggle the switch may be any suitable force, such as those described above. The switch may be configured to automatically toggle back once the force is removed, or the meter housing may toggle the switch back upon completion of the testing procedure. Additionally, in some variations, the activation element may comprise a second switch, which may be toggled to cancel or abort a testing procedure if a user applies too much force to the cartridge. In still other variations, the activation element may comprise one or more light beams, one or more strain gauges, one or more capacitive touch switches, one or more Hall Effect sensors, or the like.

Figure 10A:
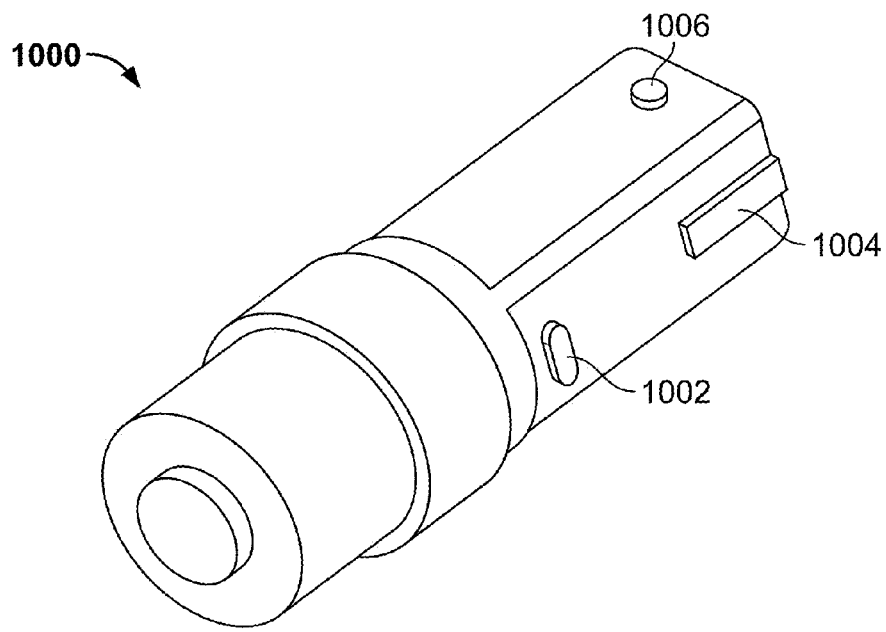
FIGS. 10A and 10B illustrate another variation of a tower suitable for use with the meters described here.
Figure 10B:
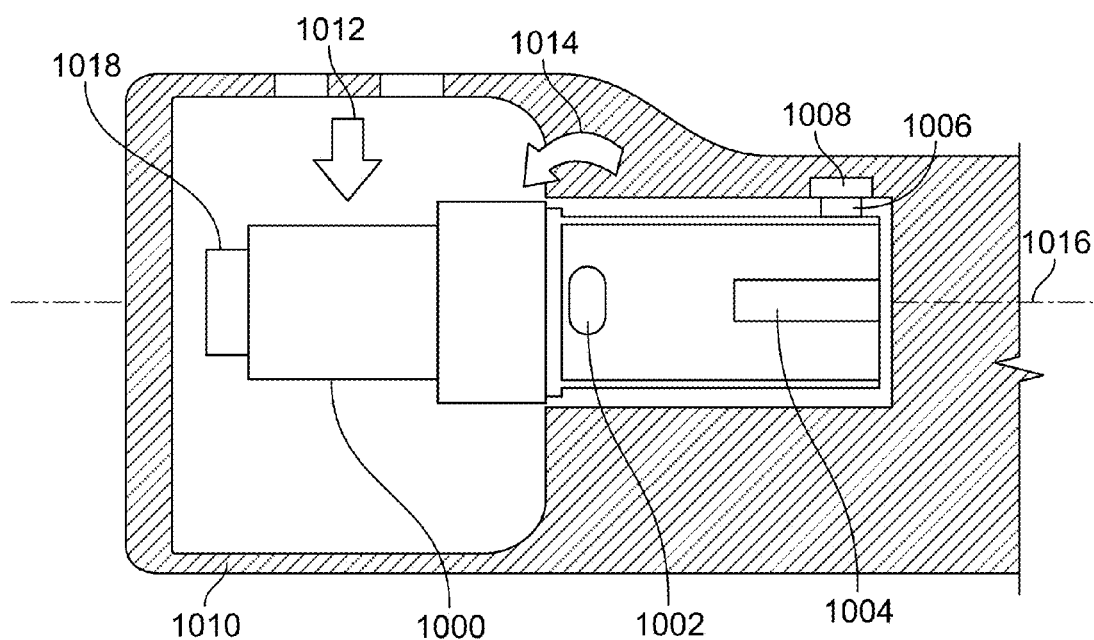

FIGS. 10A and 10B illustrate another variation of a tower that may be configured to be moveable relative to a meter housing. Specifically, FIG. 10A shows a perspective view of tower (1000). As shown there, tower may comprise central rotation pins (1002), guide protrusions (1004), and an activation protrusion (1006). As shown in FIG. 10B, tower (1000) may be placed in a meter housing (1010) such that tower (1000) may be configured to move axially and/or rotate relative to a longitudinal axis (1016) of the meter housing (1010). Specifically, central rotation pins (1002) and guide protrusions (1004) may sit within or otherwise engage one or more tracks (not shown) of the meter housing (1010). Central rotation pins (1002) may be able to rotate relative to the meter housing, thereby allowing tower (1000) to rotate relative to meter housing (1010). For example, when a force (represented by arrow (1102)) is applied to an end of tower (1000) (e.g., via a cartridge), the central rotation pins (1002) may act as an axis of rotation around which the tower (1000) may rotate (as illustrated by arrow (1014)). This rotation may place and/or press a portion of tower (1000) (e.g., activation protrusion (1006)) into operative engagement with an activation element (1008), such as those described in more detail below. Additionally, central rotation pins (1002) and guide protrusions (1004) may be configured to be axially slidable relative to the meter housing (1000), and may be biased in one direction (e.g., via one or more springs, as described in more detail above).

It should be appreciated that the central rotation pins (1002) need not be located equidistantly between the two ends of tower (1000), but may be placed along any suitable intermediate location. By placing the central rotation pins (1002) in an intermediate location, end (1018) of tower (1000) may require less lateral displacement relative to axis (1016) (i.e., in the direction of arrow (1012)) in order to place the tower (1000) in engagement with activation element (1008). This may allow for narrower tolerances between the working components of the device.

While shown in FIGS. 10A and 10B as comprising guide protrusions (1004), tower (1000) need not. In variations that do comprise guide protrusions (1004), the guide protrusions (1004) may engage with the meter housing (via one or more tracts) to limit lateral displacement of the tower and/or limit the rotation of the tower. Additionally, while shown in FIGS. 10A and 10B as comprising an activation protrusion (1006), tower (1000) need not. In variations that do comprise an activation protrusion (1006), the activation protrusion may help press or otherwise engage one or more activation elements (1008).

While the towers described above in relation to FIGS. 7A, 7B, 10A, and 10B may be moveable relative to a meter housing, it should be appreciated that a tower may be fixed relative to a meter housing. In these variations, the tower may still engage one or more cartridges, such as described above. Application of a force to the cartridge may induce a deflection, deformation, or distortion in the body of the tower. This deflection may be measured to initiate a testing procedure. Specifically, an activation mechanism comprising a strain gauge may be connected to or otherwise associated with the tower to measure the load being applied to a tower, which may be representative of the force being applied to the cartridge. The activation mechanism may comprise any suitable strain gauge (e.g., a full-bridge strain gauge, a half-bridge strain gauge, or the like). When the strain gauge determines that force being applied to the tower is within a predetermined range (and/or reaches a predetermined threshold), the meter may initiate a testing procedure. In some instances, the meter may be configured to prevent the initiation of a testing procedure if the force applied to the tower is outside of a predetermined range.

For example, FIGS. 21A and 21B illustrate a perspective view and a cross-sectional side view, respectively, of one variation of a tower (2100) which may be fixed relative to a meter housing (not shown). The tower (2100) may be fixed to the meter housing one or more threaded fasteners (not shown) or other mechanical fixation members. As shown there, the tower (2100) may comprise a strain gauge (2102), such as one or more of the strain gauges described immediately above. A cartridge (not shown) may be placed in engagement with the tower (2100), such as, for example, described above with respect to FIGS. 1A-1D and FIGS. 7A and 7B. When a force is applied to the cartridge (e.g., via a port upon application of pressure by a sampling site to the port) the engagement between the cartridge and the tower (2100) may cause deflection/deformation of the tower (2100), and this deflection may be measured by the strain gauge (2102). Data from the strain gauge (2102) may be carried to a printed circuit board assembly (2104) or other processing assembly via an optical cable (2106) or other suitable data transmission assembly. When the meter determines that force being applied to the tower/cartridge/port is within a predetermined range (and/or reaches a predetermined threshold), such as described in more detail above, the meter may initiate a testing procedure. In some instances, the meter may be configured to prevent the initiation of a testing procedure if the force applied to the tower is outside of a predetermined range. As shown in FIGS. 21A and 21B, the tower (2100) may comprise an imaging system comprising a light-generating assembly (2108) and a light-receiving assembly (2110), such as one of the imaging systems described in more detail below, but it should be appreciated that the towers described here need not include any imaging systems.

Cartridge Ejection

In some variations of the meter housings described here, the meter housing may comprise one or more mechanisms for ejecting a cartridge from the meter housing. In some variations, the cartridge-ejection mechanism may eject a cartridge without requiring direct user contact with the cartridge, which may help to reduce the risk of user exposure to potentially hazardous materials (e.g., used needles or lancets). In some variations, the cartridge may be configured to passively fall from a cartridge-receiving chamber when a door to the chamber is opened. In other variations, one or more structures may be used to push or otherwise advance the cartridge form the chamber.

Figure 12A:
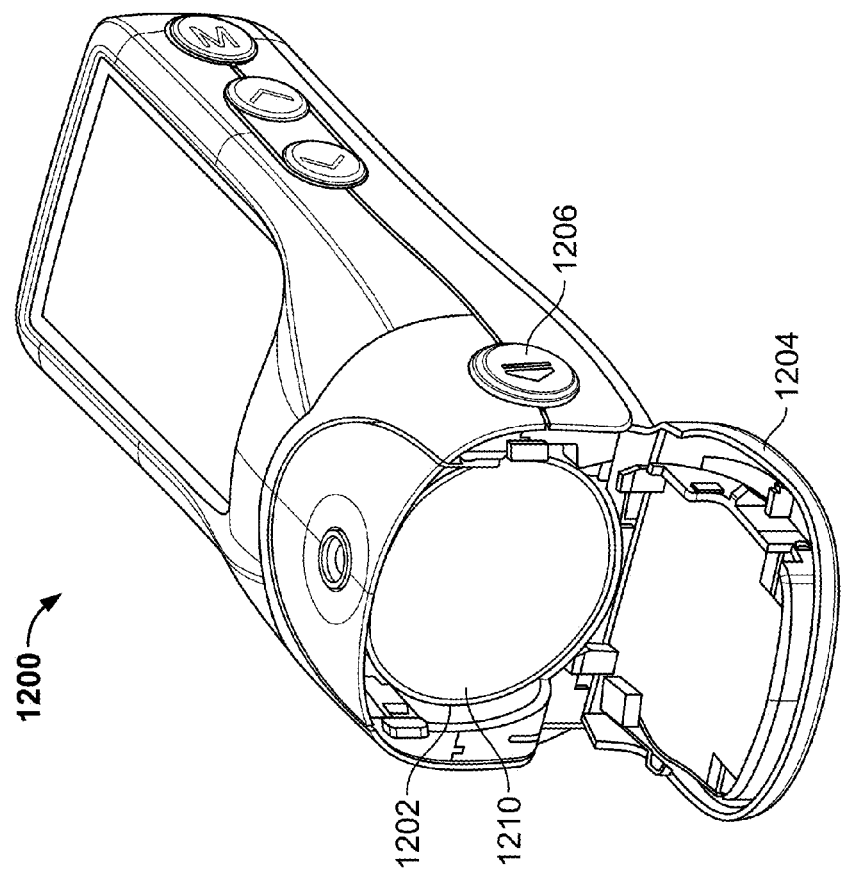
FIGS. 11, 12A and 12B illustrate variations of meter housings comprising cartridge ejection mechanisms.
Figure 12B:
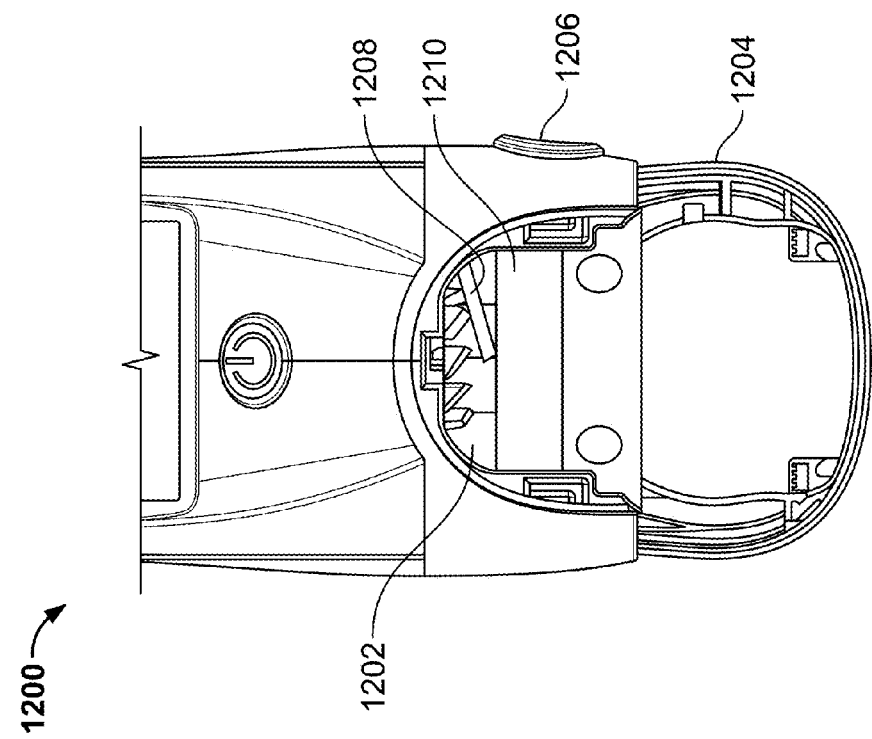

FIGS. 12A and 12B illustrate one variation of a meter housing (1200) comprising a cartridge ejection mechanism. As shown there, meter housing (1200) may comprise a cartridge-receiving chamber (1202), door (1204), and a cartridge ejection mechanism comprising button (1206) and lever (1208). In some variations the lever may have a forked or multi-pronged shape, but it should be appreciated that the lever may have any suitable size or shape. FIG. 12A shows a perspective view of meter housing (1200) with door (1204) in an open position, and cartridge (1210) placed inside of the cartridge-receiving chamber (1202). FIG. 12B shows a front view of meter housing (1200) with a portion of the meter housing removed.

To eject a cartridge (1210) from cartridge-receiving chamber (1202), button (1206) may be depressed or otherwise activated. Button (1206) may be linked to lever (1208) such that activation of the button (1206) causes lever (1208) to rotate within cartridge-receiving chamber (1202). In some variations, depression of the button (1206) mechanically actuates the movement of lever (1208). In other variations, depression of the button (1206) may provide a signal to one or more motors, cams, or other actuators which may in turn drive movement of the lever (1208). As lever (1208) rotates within cartridge-receiving chamber (1202), it may press against cartridge (1210), as shown in FIG. 12B. When door (1204) is open, rotation of the lever (1208) may push the cartridge (1210) out of the cartridge-receiving chamber (1202), thereby ejecting the cartridge (1210) from the meter housing (1200).

In some variations, button (1206) may be used to open door (1204) and to actuate lever (1208). In some of these variations, depression or activation of the button (1206) simultaneously opens door (1204) and actuates lever (1208). In other variations, the force provided by lever (1208) to cartridge (1210) may be sufficient to cause the door (1204) to unlatch or otherwise open. In other variations, the lever (1208) may not be actuated until the door (1204) is opened. In these variations, a first depression or activation of the button (1206) may open the door (1204), and a subsequent depression or activation of the button (1206) (with door (1204) open) may actuate lever (1208) to eject a cartridge. It should also be appreciated that different buttons or mechanisms may be used to open the door and to actuate the lever.

Figure 11:
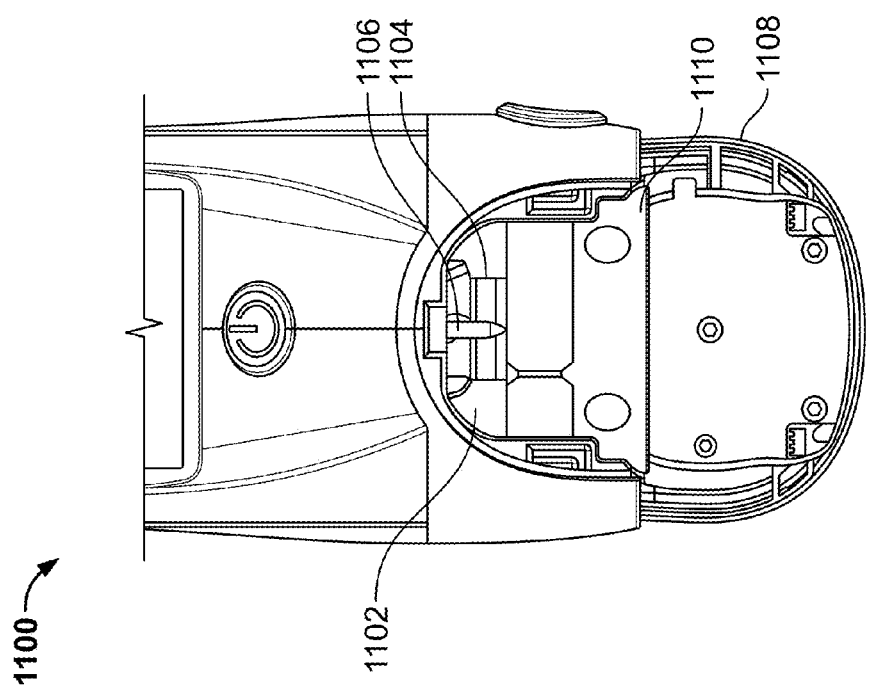

FIG. 11 depicts another variation of a meter housing (1100) comprising an cartridge-ejection mechanism. As shown there, a portion of meter housing (1100) is removed to reveal a cartridge-receiving chamber (1102), tower (1104), and a cartridge ejection mechanism comprising an ejection pin (1106). Also shown there is a door (1108) in an open position, and a cartridge (1110) placed inside of cartridge-receiving chamber (1102). To eject cartridge (1110) from cartridge-receiving chamber (1102), ejection pin (1106) may be advanced to engage cartridge (1110) and push cartridge (1110) out of the meter housing (1100). A user may initiate the movement of ejection pin by depressing or activating one or more buttons or the like, which may mechanically drive the ejection pin (1106), or may send a signal to one or more motors, cams, or actuators to drive the ejection pin (1106). In variations where a trigger pin and/or vacuum pin may enter one or more cartridge cells (e.g., to activate one or more sampling arrangements, as described in more detail above), the same trigger pin or vacuum pin may also be used to eject the cartridge. In these variations, the cartridge and pin may be aligned in a first orientation in which advancement of the pin causes the pin to enter a cartridge cell (e.g., through one or more apertures in a wall of the cell). To eject the cartridge, the cartridge and pin may be aligned in a second orientation in which advancement of the pin causes the pin to push against one of the walls of the cartridge. In other variations, a meter housing may comprise separate ejection, triggering, and/or vacuum pins.

Imaging System

As mentioned above, the meters described here may comprise one or more imaging systems, but need not. Indeed, in variations where the sampling arrangement comprises one or more electrochemical quantification members, it may not be necessary to have an imaging system. In variations where the meter housing comprises an imaging system, the imaging system may act to visualize, view, detect, or otherwise measure one or more optical parameters of a portion of the meter (e.g., a sampling arrangement). For example, in some variations, a cartridge may comprise a sampling arrangement with a reagent pad that reacts with a fluid sample (e.g., a blood sample, control solution) to cause a color change, which may be indicative of the glucose concentration of that fluid sample. An imaging system of the meter may visualize the reagent pad during this reaction to obtain or otherwise record information about the reaction (e.g., reaction rates, the amount of color change, or the like), and this data may be analyzed to determine one or more characteristics of the fluid sample, such as the sample's glucose concentration, a hematocrit level in the sample, the volume of sample applied to the pad, combinations thereof, and the like. The imaging system may also be used to determine whether a control sample has been applied to a sampling arrangement, as will be described in more detail below.

The imaging system may be housed in any suitable portion of the meter. Generally, the imaging system is at least partially contained in the meter housing, although it should be appreciated that the cartridge may comprise one or more portions of the imaging system. In variations where the meter housing comprises the imaging system, the individual components of the imaging system may be housed in any suitable portion or portions of the meter. In some of these variations, one or more components of the imaging system may be housed in a tower of the meter. In variations where a cartridge and tower are aligned or held in place relative to each other, such as tower (700) and cartridge (703) described above in relation to FIGS. 7A and 7B, this engagement between the tower and a cartridge may at least temporarily hold the cartridge in a fixed relation relative to the imaging system. This may make the imaging system less sensitive to patient movement, as it may be more difficult to move the cartridge relative to the imaging system during a testing procedure.

The imaging systems described here generally comprise a light-generating assembly and a light-receiving assembly. The light-generating and light-receiving assemblies may be positioned in any suitable portion of the meter. In variations in which a meter as described here comprises a tower (as described in more detail above), one or more of these assemblies may be partially or wholly housed in the tower. In some of these variations, both the light-generating and light-receiving assemblies may be housed within the tower. In other variations, the light-generating assembly may be housed within the tower and the light-receiving assembly may be housed within another portion of the meter housing, or vice versa.

Generally, the light-generating assembly may be configured and used to generate and direct light toward one or more portions of a meter (e.g., one or more portions of a sampling arrangement, such as a reagent pad or the like). The light-generating assembly generally comprises one or more light sources. In some instances a light-generating assembly may comprise a light source that is configured to generate light at a predetermined wavelength or within a predetermined wavelength range. Additionally or alternatively, a light-generating assembly may comprise a polychromatic light source. In other variations, a light-generating assembly may comprise a light source which may be configured to selectively generate light at two or more different predetermined wavelength or light within different predetermined wavelength ranges. For example, in some variations a light source comprises a RGB LED, which can selectively output red, green, and blue light. In some variations, a light-generating assembly may comprise two or more separate light sources, each of which may be configured to generate light at a predetermined wavelength or wavelength range. Accordingly, the light-generating assembly may be configured to produce light at a plurality of wavelengths, which may assist the imaging system and meter to determine an analyte concentration, or may assist the imaging system and meter in determining the application of a control solution, as will be described in more detail below. In some variations, a light-generating assembly may comprise a diffusor, which may spread out or otherwise scatter light generated by the light source or sources. Additionally or alternatively, a light-generating assembly may comprise a collimator, which may focus or otherwise align light generated by the light source or sources. Additionally or alternatively, a light-generating assembly may comprise baffling or other light traps, which may help trap or otherwise remove stray light generated by the light-generating assembly. It should be appreciated that some or all of the components of a light-generating assembly may be included as individual components, while other components may be combined into a multi-purpose component. For example, some variations of the light-generating assemblies described here may comprise an element that includes both a collimator and light traps.

The light-receiving assembly of the imaging systems described here may be configured to image one or more areas of the meter. For example, in variations where the meter comprises one or more sampling arrangements, such as those described above, the light-receiving assembly may be configured to image one or more components of a sampling arrangement (e.g., detect and measure light reflected off of or emitted from the sampling arrangement), as will be described in more detail below. The light-receiving assembly may comprise one or more detectors/image sensors, which may produce one or more electrical signals in response to light received by the assembly. In some variations, the light-receiving assembly may comprise one or more filters, which may filter out one or more wavelengths of light received by the light-receiving assembly. Additionally or alternatively, the light-receiving assembly may comprise one or more lenses, which may focus or otherwise redirect light within the light-receiving assembly. Additionally or alternatively, the light-receiving assembly may comprise one or more mirrors which may act to redirect light through the light-receiving assembly. Additionally or alternatively, the light-receiving assembly may comprise baffling or other light traps to capture stray light within the light-receiving assembly. It should be appreciated that some or all of the components of a light-receiving assembly may be included as individual components, while other components may be combined into a multi-purpose component. For example, in the variation of tower (2100) described above with respect to FIGS. 21A and 21B, the light-receiving assembly (2110) may comprise a molded optical element (2112), which may both focus and redirect light from a sampling arrangement toward a detector (2114).

Figure 9A:
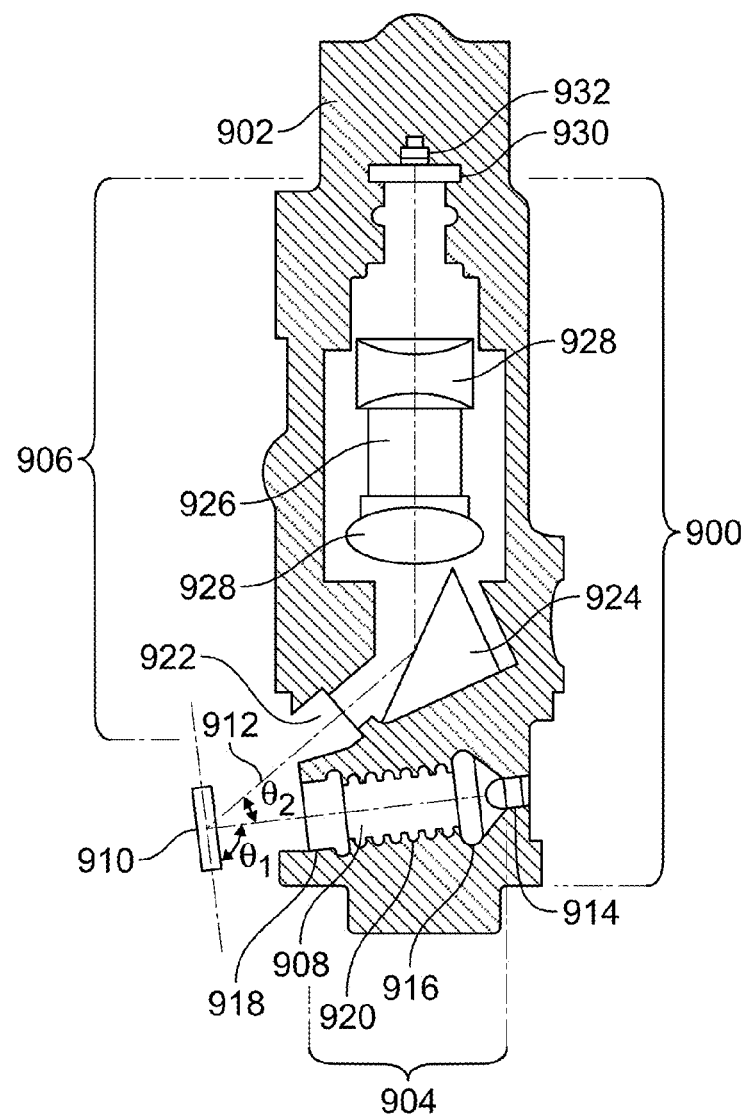
FIGS. 9A and 9B depict an illustrative variation of an imaging system suitable for use with the meters described here.
Figure 9B:
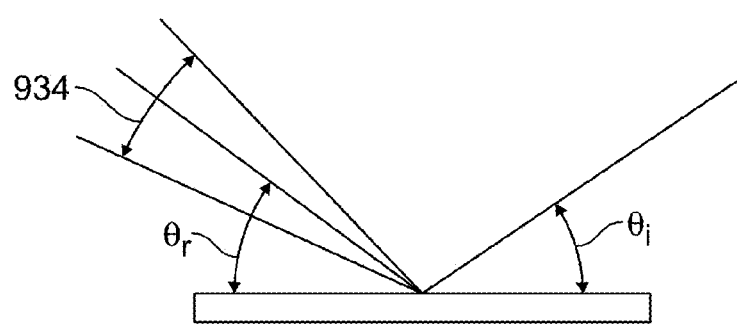

FIGS. 9A and 9B illustrate one variation of imaging system (900). As shown there, imaging system may be housed within a tower (902), and may comprise a light-generating assembly (904) and a light-receiving assembly (906). While imaging system (900) is shown in FIGS. 9A and 9B as having separate light-generating and light-receiving assemblies ((904) and (906), respectively), it should be appreciated that the imaging system may comprise an assembly that both generates and receives light. Generally, light-generating assembly (904) may be configured to generate one or more beams of light (represented by line (908)) which may reflect off of a pad (910) and/or other portions of a sampling arrangement. Some of the light reflected off pad (represented by line (912)) may enter light-receiving assembly (906), where it may be analyzed, as will be described in more detail below. While shown in FIG. 9 as reflecting off of pad (910), it should be appreciated that the imaging-system may visualize any structure that is in the viewing field of the imaging system (900) (e.g., in a position to reflect the generated light (908) into the light-receiving assembly (906)).

Light-generating (904) and light-receiving (906) assemblies may comprise any suitable elements or combination of elements. For example, as shown in FIG. 9A, light-generating assembly (904) may comprise a light source (914), diffuser (916), and collimator (918). The light source (914) may be any suitable light-generating mechanism (e.g., a light-emitting diode, gas-discharge lamp, bulb, chemical light-source, or the like). Diffuser (916) may be any suitable diffuser (e.g., a ground glass diffuser, grey glass diffuser, opal glass diffuser, a Teflon diffuser, or the like) or the like, and may scatter or otherwise spread out the light generated by the light source (914). Collimator (918) in turn may comprise one or more curved mirrors or lenses (not shown) and may act to receive the diffused light from diffuser (914) focus/align the scattered beams of light. Light-generating assembly (904) may further comprise baffling (920) or other light traps between the diffuser (914) and the collimator (918) to help remove stray light. Overall, the diffuser (914), baffling (920), and collimator (918) may transform the light from light-source (914) into a focused beam of light.

The generated light (908) may strike pad (910) at an angle ($\theta_1$) relative to the surface of the pad. In variations where the sampling arrangement is configured to rotate relative to a cartridge, such as sampling arrangement (300) described above in relation to FIGS. 3A-3E, angle ($\theta_1$) may change as the pad (910) rotates with the sampling arrangement. Thus, for the purposes of discussion, angle ($\theta_1$) will refer to the angle between generated light (908) and the surface of pad (910) when the pad is at its resting position. Angle ($\theta_1$) may have any suitable value, such as, for example, between about 85 and about 95 degrees, between about 80 degrees and about 100 degrees, and between about 75 degrees and about 105 degrees, and preferably about 90 degrees. The choice angle ($\theta_1$) may affect the placement of the light-receiving assembly (906), as will be described in more detail below.

As shown in FIG. 9A, light-receiving assembly (906) may comprise a first passage (922), mirror (924), focusing arrangement (926) comprising lenses (928), filter (930), and detector (932). Generally, first passage (922) may receive light that is reflected off of pad (910) or another structure in the viewing field of the imaging system (900). Reflected light (912) may then reflect off of mirror (924), where it may be passed into focusing arrangement (926). While shown in FIG. 9 as reflecting off a mirror (924), it should be appreciated that the reflected light (912) may travel directly to the focusing arrangement without first being reflected. In some variations, a mirror may be integrated into a surface of one or more focusing elements. Focusing arrangement (926) may comprise any suitable lens or combination of lenses (928) (e.g., one or more concave lenses and/or one or more convex lenses) capable of focusing the reflected light (912) toward detector (932).

Although shown in FIG. 9A as comprising a filter (930), light-receiving assembly (906) need not. In variations that do comprise a filter (930), filter (930) may comprise any suitable filter or filters (e.g., one or more absorptive filters, one or more dichroic filters, one or more monochromatic filters, or the like). Similarly, detector (932) may be any suitable detector element or elements. For example, in some variations, the detector may comprise one or more photo diodes, CCDs, or CMOS detector elements. In variations where the detector comprises a plurality of detector elements (e.g., a plurality of CMOS detector elements), the detector elements may be arranged into an array. The array may be a linear one-dimensional array, or may be a two-dimensional array. It should be appreciated that some or all of the components of the imaging systems may be combined or otherwise integrated with one another. For example, in some variations, a light source (e.g., a light-emitting diode) may be integrated with a diffuser. In other variations, one or more lenses may be integrated into an optical element. In still other elements, a lens element and a filter element may be combined by coloring the lens element.

When a light-receiving assembly of an imaging element is configured to image one or more portions of a sampling arrangement (e.g., a reagent pad), the light-receiving assembly may be positioned relative to the sampling assembly so as to help avoid the light-receiving assembly from receiving specular reflections when light from a light-generating assembly strikes the imaged portions of the sampling assembly. Specifically, when light hits the imaged components of a sampling arrangement (e.g., a reagent pad, a cap), specular reflectance may occur in which beams of light striking the sampling arrangement are reflected at an angle of reflectance equal to the angle of incidence. The components of the sampling arrangement may otherwise act as a diffuse reflectance surface, scattering light from a light-generating assembly uniformly. As long as the light-receiving assembly is not receiving specular reflectance, the diffuse reflectance may be constant regardless of the angle at which the light-receiving assembly receives the light. Accordingly, it may be desirable to configure the light-receiving assembly to receive the diffusely-scattered light while avoiding the specular reflectance. When a beam of collimated light (e.g., light generated by a light-generating assembly including a collimator) strikes a sampling arrangement along an axis of illumination (such as light (908) shown in FIG. 9A), the specular reflection may occur within a specific range around an axis of reflection that at an angle complementary to the axis of illumination. For example, in some variations, specular reflectance for a sampling arrangement may occur within about 20 degrees on either side of the axis of reflection.

Accordingly, in some variations, the light-receiving assembly may be positioned off the axis of reflection by at least about 20 degrees to avoid the specular reflectance.

For example, in the imaging system shown in FIGS. 9A and 9B, the first passage (922) may be configured such that only light reflected at a certain angle ($\theta_2$) (or a narrow range of angles) to the generated light (908) reaches mirror (924) (or other portions of the light-receiving assembly (906). Specifically, first passage (922) may comprise baffling or other light traps (not shown) which may act to capture stray light. Angle ($\theta_2$) may be any suitable angle, e.g., greater than about 20 degrees, greater than about 30 degrees, greater than about 40 degrees, greater than about 50 degrees, between about 15 degrees and about 25 degrees, about 25 degrees and about 35 degrees, between about 35 degrees and about 45 degrees, between about 45 degrees and about 55 degrees, and the like.

The choice of angle ($\theta_2$) may be partially determined by angle ($\theta_1$), the expected rotation of the pad (910), the physical characteristics of pad (910) and the nature of the light produced by the light-generating assembly (904). For example, angle ($\theta_2$) may be specifically chosen to minimize the chance of flaring that may occur as generated light (908) reflects off of pad (910). Specifically, when generated light (908) strikes pad (910), pad (910) may act as an imperfect lambertian surface to scatter light in every direction. As mentioned above, the apparent radiance of the pad may be independent of the angle at which it is viewed, except that specular reflectance may result in more intense reflection at or around an axis of reflection complimentary to the angle of incidence. For example, as illustrated in FIG. 9B generated light (908) may strike pad (910) at an angle of incidence ($\theta_i$). Although the apparent radiance of the pad (910) may be the same for most viewing angles, there may be some flaring (from specular reflectance) at a range (934) of angles near the angle of reflectance ($\theta_r$), in which the apparent radiance of the pad may be orders of magnitude brighter.

Because flaring may affect the ability of detector (930) to image the pad (910), it may be desirable to configure the imaging system (900) such that light-receiving assembly (904) does not receive reflected light (912) in the range (934) of flaring as described above. As such, in some variations, angle ($\theta_2$) may be determined by the following equation:

$$\theta_2 \geq 2*((90-\theta_1)+(\theta_1)+(\theta_{mr}))+\tfrac{1}{2}*(\theta_f)$$

Where angle ($\theta_{mr}$) is the maximum angle of rotation of pad relative to the extended position during visualization, and ($\theta_r$) is the range (934) of flaring as described in more detail above. The range (934) of flaring may depend on the nature of the generated light (908) as well as nature of the pad (910). For example, in some variations of the meters described here, the sampling arrangement may be configured such that once pad (910) hits its point of maximum forward rotation, it may only rotate back about 10 degrees during visualization. Additionally, in some variations the range of flaring may be the angle of ($\theta_r$)±about 15 degrees (thus ($\theta_f$) would be about 15 degrees. Thus, in variations where angle ($\theta_1$) is about 90 degrees, angle ($\theta_2$) may be greater than about 35 degrees.

Additionally, the meter may be configured such that the apparent radiance of the pad (910) as viewed by light-receiving assembly (906) does not significantly change as the pad (910) rotates. When the angle between a light source and the normal to a lambertian surface increases, the apparent brightness of the surface decreases. Thus, as pad (910) rotates away from the extended position, the apparent brightness of the pad may decrease. During rearward rotation, however, the pad (910) may be brought closer to light-generating assembly (904). Because the intensity of light increases closer to a light source, the decrease of intensity due to the rotation of the pad may be canceled by the increase of intensity as the pad approaches the light-generating assembly.

As mentioned above, the imaging systems of the meters described here may be configured to image one or more portions of a sampling arrangement. The imaged portions of the sampling arrangements may be controlled by the components of the light-receiving assembly as well as the relative positioning between the light-receiving assembly and the sampling arrangement. For example, in variations of the meters described here that comprise a sampling arrangement which is configured to rotate or otherwise move relative to a portion of the meter (as described in more detail above), the imaging assembly may image different portions of the sampling arrangement as the sampling arrangement moves.

In some variations, the light-receiving assembly of an imaging system may comprise a detector that comprises a single detector element. In these variations, the detector may image a single point on a sampling arrangement. For example, FIG. 14 depicts a partial view of a sampling arrangement (1400) comprising a reagent pad (1402) and a cap (1404). An imaging system (not shown) comprising a single-element detector may be configured to view a single-pixel viewing area (1406). The size of this viewing area (1406) may be altered using one or more lenses or other focusing elements and/or modifying the relative positioning between the sampling arrangement (1400) and the imaging system. It should be appreciated that the sampling arrangement (1400) is depicted in FIG. 14 for illustrative purposes, and a single-element detector may be used to image a portion of any suitable sampling arrangement including any components or combination of components, such as those described in more detail above.

In other variations, the light-receiving assembly of an imaging system may comprise a detector that comprises one or more linear arrays of detector elements. In these variations, a detector may include any suitable number of linear detector arrays (e.g., one linear array, two linear arrays, three or more linear arrays, or the like), and each linear array may be configured to view a multi-pixel linear viewing area. The linear detector arrays may be configured to image one or more portions of a sampling arrangement. For example, FIG. 15A depicts one variation of a sampling arrangement (1500) comprising a reagent pad (1502) and a cap (1504). Although only reagent pad (1502) and cap (1504) are shown in FIG. 15A, it should be appreciated that the sampling arrangement (1500) may comprise any additional element (e.g., a hub, a skin penetration member) or combination of elements such as those described in more detail above. As shown in FIG. 15A, an imaging system comprising a linear detector array (not shown) may be configured to image a linear viewing area (1506) divided into a plurality of pixels (1508), where each pixel (1508) corresponds to a detector element.

The viewing area (1506) of the imaging system may image any portion or portions of the sampling arrangement (1500). In some variations, the viewing area may be configured to image only a portion of reagent pad (1502). In other variations, the viewing area may be configured to image the reagent pad (1502) and the cap (1504). In still other variations (such as that illustrated in FIG. 15A), the viewing area may be configured to image the reagent pad (1502), the cap (1504), and open space (1510) around the cap (1504). While shown in FIG. 15A as imaging the open space (1510) on two sides of the cap (1504), the viewing area (1506) of the imaging system may image the open space (1510) on one side of the cap (1504). When the reagent pad (1502) and cap (1504) are illuminated using an imaging system, these components may reflect light while the space (1510) around it may not. FIG. 15B shows an example of a trace (1512) collected from the pixels (1508) of viewing area (1506), which reflects the amount of light collected from each of the detector elements when illuminated by the imaging system. As shown there, trace (1512) may include a first segment (1514) corresponding to the pixels imaging the reagent pad (1502), second and third segments (both labeled as (1516)) corresponding to the pixels imaging the cap (1504), and fourth and fifth segments (both labeled as (1518)) corresponding to the pixels imaging the open space (1510) around the cap (1504).

The meters described here may be configured to distinguish between the different segments of trace (1512) during a sampling procedure. For example, the first segment (1514) of the trace (1512) may be used in determination of the concentration of an analyte in a sample applied to the reagent pad (1502), such as described in more detail below. The second and third segments (1516) may assist in analysis of the sample. In some variations the cap (1504) may be used as a reference standard, and the first segment (1514) of the trace (1512) may be adjusted based on the values of the second and third segments (1516). For example, the cap (1504) may be formed or otherwise coated with a material having a known reflectance level. When the second and third segments (1516) (i.e., the light reflected from the cap (1504)) deviate from values expected from the known reflectance level, the first segment (1514) or another portion of the trace (1512) may be adjusted or otherwise corrected based on this deviation. While the cap (1504) may be used as a reference standard, it should be appreciated that one or more other structures may be used as a reference standard, as will be described in more detail below. In these variations, the imaging system may be configured to adjust one or more outputs of the detector based on the deviation between a measured reflectance and an expected reflectance of the reference standard component.

Additionally or alternatively, the light received from the open space (1510) may also be used to adjust the sample analysis. Because the pixels (1508) imaging the open space (1510) are not imaging the sampling arrangement (1500), light received by these pixels may be considered stray light. Too much stray light within the meter housing may affect that validity of one or more measurements from the imaging system. Accordingly, when the light received by the pixels imaging the open space (1510) (e.g., fourth and fifth segments (1518) of trace (1512)) reaches a certain threshold for a particular reading, the meter may take one or more actions. In some of these variations, the meter may be configured to cancel a testing procedure and/or return an error value to a user. In other variations, the meter may be configured to exclude specific readings in which the light received by the pixels imaging the open space (1510) exceeds a predetermined threshold.

While the viewing area (1506) is shown in FIG. 15A as imaging across a midline of the reagent pad (1502), an imaging system comprising a linear detector array may visualize any suitable portion of the pad. Additionally, in variations where a sampling arrangement is configured to move relative to the meter, movement of the pad may change the area of the sampling arrangement that is imaged. For example, FIGS. 16A-16C illustrate a variation of a meter (1600) comprising a sampling arrangement (1602) that is configured to rotate relative to the meter (1600). FIG. 16A shows a portion of the meter (1600), specifically a tower (1604) and a cartridge (1606) housing the sampling arrangement (1602), but it should be appreciated that the meter (1600) may comprise any suitable elements or combination of elements as described hereinthroughout. Also shown there is an imaging system comprising a light-generating assembly (1603) and a light-receiving assembly (1605). While both of these assemblies are shown in FIG. 16A as being housed in the tower (1604), it should be appreciated that each of the assemblies may be located in any suitable portion of the meter (1600).

A variation of the sampling arrangement (1602) is shown in FIG. 16A as comprising a hub (1608), a skin-penetration member (1610), a reagent pad (1612), and a cap (1614), but it should be appreciated that the sampling arrangement may comprise any elements or combination of elements such as described in more detail above. The sampling arrangement (1602) may be configured to rotate around a pivot point (1616) when triggered. For example, a torsional spring (not shown) may drive rotation of the sampling arrangement (1602). After the sampling arrangement (1602) has been triggered, it may be configured to settle at a rest position (such as the position of sampling arrangement (1602) in FIG. 16A) when there are no external forces (e.g., a patient's skin) acting on the sampling arrangement (1602). The light-receiving assembly (1605) may include a detector (1618) comprising a linear array of detector elements (not shown), and the light-receiving assembly (1605) may be configured to image one or more portions of the sampling arrangement (1602) when the sampling arrangement (1602) is in the rest position. It should also be appreciated that the light-receiving assembly (1605) may be able to image portions of the sampling arrangement (1602) as the sampling arrangement (1602) deviates from the rest position, although the imaged portions of the sampling arrangement (1602) may change as the sampling arrangement (1602) is rotated.

In some variations, the light-receiving assembly (1605) may be positioned and configured to image the midline (1620) of the reagent pad (1612) when the sampling assembly (1602) is in the rest position. In other variations, such as depicted in FIG. 16B, the light-receiving assembly (1605) may be positioned and configured to image the reagent pad (1612) (and optionally cap (1614) and open space (1622) around cap (1614), as described in more detail above) with a viewing area (1624) offset from the midline (1620) of the reagent pad (1612) on a first side of the midline (1620). When a user's skin contacts the skin-penetration member (1610) (such as during a sampling procedure), the contact between the skin and the skin-penetration member (1610) may cause the sampling arrangement (1602) to rotate toward the light-receiving assembly (1605) (illustrated in FIG. 16A with arrow (1626)). In these instances, the sampling arrangement (1602) and the imaging system may be configured such that rotation of the sampling arrangement (1602) toward the light-receiving assembly (1605) causes the viewing area (1624) to move toward the midline (1620) of the reagent pad (1612). Continued rotation of the reagent pad (1612) may move the viewing area (1624) past the midline (1620) to a second side of the midline (1620), as shown in FIG. 16C. Because the number of pixels (1628) of the viewing area (1624) that are imaging the reagent pad (1612) may increase as the viewing area (1624) approaches the midline of the exposed portion of the reagent pad (1612) (e.g., when the exposed portion of the reagent pad is circular or oval in shape), configuring the viewing area (1624) to transition from one side of the midline (1620) to the other as the sampling arrangement (1620) rotates may maximize the number of pixels (1628) that can image the reagent pad (1612) during this rotation.

In the variation described above with respect to FIGS. 16A-16C, the viewing area (1624) imaged by the light-receiving assembly may be parallel to an axis of rotation of the sampling arrangement. It should be appreciated, however, that the viewing area (1624) may be perpendicular to the axis of rotation of the sampling arrangement, or may be otherwise angled relative to the axis of rotation of the sampling arrangement.

In some variations, the detectors described here may comprise two or more linear arrays of detector elements. FIG. 18A shows one variation of a sampling arrangement (1800) comprising a reagent pad (1802) and a cap (1804). An imaging system (not shown) comprising two linear detector arrays (not shown) may image a first viewing area (1806) and a second viewing area (1808). Two detector arrays may increase the overall number of pixels (1810) that visualize the reagent pad (1802). The first and second viewing areas may be positioned on either side of a midline (1812) of the reagent pad (1802) when the sampling arrangement (1800) is in a rest position, which may compensate for movement in a direction indicated in by line (1814). Specifically, as one of the viewing areas moves away from the midline, the other viewing area may move toward the midline.

While the first and second viewing areas are shown in FIG. 18A as being parallel, the detector arrays may image viewing areas that a positioned at any suitable angle relative to each other. For example, FIG. 18B shows the sampling arrangement (1800) describe above with respect to FIG. 18A. As shown there, the linear detector arrays may be configured to image a first viewing area (1816) that is perpendicular to a second viewing area (1818). In these variations, the first and second viewing areas may compensate for movement in multiple directions. It should be appreciated that the detectors described above may comprise any suitable number of linear detector arrays (e.g., one, two, or three or more), and these arrays may have any suitable relative positioning between them. In still other variations, a detector may comprise a two-dimensional detector array. For example, FIG. 19 depicts a sampling arrangement (1900) that is may be imaged by a detector (not shown) comprising a two-dimensional detector array. As shown there, the detector array may image a viewing area (1902) comprising rows and columns of pixels (1904).

As mentioned above, the imaging system may be configured to use one or more imaged portions of a sampling arrangement as a reference standard. As mentioned above, the reference standard may be formed from or otherwise include a material having a known reflectance value. The meter may be configured to correct or otherwise alter one or more measurements (such as described in more detail above) based on the variation between the expected reflectance value and the actual reflectance value for the reference standard. Any suitable portion of the sampling arrangement (or other component of the meter) may be used as a reference standard. FIGS. 20A-20C depict variations of sampling arrangements in which one or more portions of the sampling arrangement may be used as a reference standard. FIG. 20A depicts one variation of a sampling arrangement (2000) comprising a reagent pad (2002) and a cap (2004), wherein the cap (2004) may be used as a reference standard. FIG. 20B depicts another variation of a sampling arrangement (2006) comprising a reagent pad (2008) and a cap (2010), in which a section (2012) of the reagent pad (2008) may be used as a reference standard. Placing the reference standard closer to the reagent pad (2008) may decrease potential illumination variations that may occur during imaging. In some variations the reference standard section of the reagent pad may be one or more films attached to the reagent pad, or the reagent pad may be partially coated or printed with a colored material. In other variations, a reference standard section of a reagent pad may comprise a reagent that produces a predetermined color change when a sample is applied to the pad, regardless of the analyte content of the sample. While the reference standard section (2012) is shown in FIG. 20B as surrounding a periphery of the exposed reagent pad (2008), it should be appreciated that the reference standard section (2012) may be on any suitable portion or portions of the reagent pad (2008). For example, FIG. 20C shows a variation of a sampling arrangement (2014) comprising a reagent pad (2016) and a cap (2018), wherein a strip (2020) extending along the reagent pad (2016) may act as a reference standard.

The imaging systems described here may be configured to measure one or more specific wavelengths (or ranges of wavelengths) when imaging one or more portions of a meter, such as a sampling arrangement. For example, in some variations, a reagent pad may be configured to produce a color change when a sample containing a target analyte is applied to the reagent pad. The imaging system may be configured to measure a first specific wavelength reflected from the reagent pad that is associated with the color change. For example, in some variations a reagent pad may contain one or more reagents which may produce a red color change when a fluid sample containing a target analyte (e.g., glucose) is applied to the reagent pad. In these variations, the meter may comprise an imaging system configured to measure this color change. Specifically, the imaging system may be configured to measure red light that is reflected off of the reagent pad. For example, the imaging system may be configured to measure light between about 625 and about 635 nanometers. In some variations, the imaging system may be configured to measure light at about 630 nanometers. The meter may use these readings to calculate the concentration of the target analyte (e.g., by using the rate of change of the color of the reagent pad).

In some variations, the meter may comprise an imaging system configured to measure two or more specific wavelengths (or ranges of wavelengths) when imaging one or more portions of the meter (e.g., a sampling arrangement). For example, in variations where a reagent pad comprises one or more reagents which may produce a red color change when a fluid sample comprising a target analyte (e.g., glucose) is applied to the reagent pad, one or more components of the fluid sample may affect the color development of the reagent pad. When the fluid sample comprises blood, red blood cells contained in the blood may contribute to the red color development, which may affect the concentration calculation of the target analyte. Because red blood cells absorb blue light, measuring the amount of blue light that is reflected off a reagent pad may allow for the meter to estimate the hematocrit (i.e., the concentration of red blood cells) of the fluid sample. The amount of blue light reflected off a reagent pad may be inversely related to the hematocrit level of the fluid sample. Accordingly, a meter may be configured to measure both red light and blue light from the reagent pad. When evaluating blue light, the meter may be configured to measure light between about 465 and about 470 nanometers. In some of these variations, the meter may be configured to measure light about 470 nanometers. The red light measured by the meter may be used to calculate a concentration of the target analyte, and the blue light measured by the meter may be used to provide a correction value that may adjust the analyte concentration measurement based on the estimated hematocrit.

In some instances, the meter may use one or more wavelengths to automatically check for the presence of a control solution applied to a sampling assembly. For example, in some variations, the reagent pad may comprise one or more reagents which produce a specific color change when the control sample is applied to the reagent pad. This color change may be used to signal to the meter that a control sample has been applied to the reagent pad (i.e., as opposed to a fluid sample for testing). For example, in some instances, the control sample may be configured to produce a blue color change in addition to a color change that may occur based on a reaction with a target analyte (e.g., a red color change when glucose is applied to the reagent pad). The meter may be configured to measure both the red light and the blue light reflected from the reagent pad. The red light may be used to calculate the concentration of a target analyte in the control sample, while the blue may indicate the presence of the control sample. While the level of the blue light may be used to perform hematocrit correction, as described in more detail above, the blue color change produced by the reaction between the control sample and the reagent pad may produce a reflectance value outside of any value expected for a body fluid sample (e.g., blood). The meter may be configured to identify the fluid sample as a control solution when the blue reflection is outside of this value range. Once the meter has identified the fluid sample as a control solution, it may compare the calculated concentration of the target analyte (e.g., the concentration calculated by the red color change) to an expected concentration for the control solution. If the calculated concentration deviates from the expected concentration by more than a certain amount, the meter may be configured to re-calibrate itself or alert the user that the control solution failed to produce a satisfactory response.

It should be appreciated that a reagent pad may create any suitable color change in the presence of a control solution. For example, in some variations the control solution may yield a color change that changes the reflectance of the pad for green wavelengths of light (e.g., about 525 nanometers), or any other suitable wavelength of light (including wavelengths in the visible spectrum, ultraviolet spectrum, infrared spectrum, and the like). It should be appreciated that different control solutions may result in different reflectance changes, such that the meter may identify different control solutions when applied to the reagent pads.

When a meter is configured to image lights of one or multiple wavelengths, the meter may be configured to achieve this in any suitable manner. When a meter is configured to image light at a first wavelength, the meter may comprise a light source that is configured to output light at the first wavelength. Additionally or alternatively, a light-receiving assembly of the meter may comprise a filter configured to filter out wavelengths other than the first wavelength that are received by the light-receiving assembly. Accordingly, the detector may receive light of the first wavelength. In some of these variations, the meter may comprise a light source that may be configured to output multiple wavelengths of light, with the additional wavelengths being removed by the filter.

When a meter is configured to image light at two or more wavelengths (for example, a first wavelength and a second wavelength), the meter may comprise a light source comprising a plurality of light-emitting components, wherein each light-emitting component is configured to output a different wavelength. Each light-emitting component may be any suitable component capable of generating a specific wavelength (e.g., a light-emitting diode or the like). For example, the light source may comprise a first light-emitting component configured to output a first wavelength and a second light-emitting component configured to output a second wavelength. The light source may selectively emit light at the first wavelength and/or the second wavelength by selectively activating the first and second light-emitting components. For example, the light source may comprise a RGB LED package which may selectively produce red, green, and blue light. In some variations, a light-receiving assembly of an imaging system of a meter may comprise one or more filters which may selectively filter light outside of the two or more wavelengths. In some variations, the meter may comprise a dual bandpass filter which may filter light other than the first and second wavelengths. In these variations, the filter may help prevent light outside of the selected wavelengths from reaching a detector of the light-receiving assembly. In some variations, the detector may comprise one or more photodetectors, which are configured to divide received light into different spectral components. For example, the detector may comprise a RGB photodetector which may measure the levels of red, blue, and green light received by the photodetector. In these variations, polychromatic light may be received by the detector, yet the meter may still be able to image using two or more wavelengths.

When a meter is configured to image light at two or more wavelengths, they may be imaged simultaneously or sequentially. For example, in variations where a light-receiving assembly of an imaging system that comprises a detector that may divide received light into different spectral components, the meter may image light at multiple wavelengths simultaneously. In some variations, the imaging system may be configured to sequentially illuminate a portion of the meter (e.g., a sampling arrangement) with lights of different wavelengths.

In some variations, the imaging system may be configured to strobe a light source of a light-generating assembly off and on during imaging. When the light source is off, light received by the detector may be stray light entering the meter. The meter may be configured to subtract the level of stray light from readings obtained from the imaging system when the light source is generating light. When a meter is configured to sequentially illuminate a sampling arrangement with a plurality of wavelengths, the light source may strobe off between illumination with each wavelength, or may strobe off after illumination with each of the wavelengths. For example, in variations where a meter is configured to illuminate using a first wavelength and a second wavelength, the meter may be configured to illuminate using the first wavelength, strobe off, illuminate using the second wavelength, and strobe off. This may be repeated as necessary during imaging. Alternatively, the meter may be configured to illuminate using the first wavelength, illuminate using the second wavelength, then strobe off. Again, this may be repeated as necessary to complete a concentration analysis.

User Verification

In some variations, the meter housing may comprise one or more user-verification mechanisms. In these variations, the meter may be configured such that it will only "unlock" (e.g., allow a user to perform one or more meter functions, such as performing a sampling procedure or accessing user data) when an authorized user properly activates the user-verification mechanism. User-verification mechanisms may be useful in instances where it may be desirable to prevent or otherwise limit a meter from being used or otherwise activated by an unintended user. In these instances, a meter may be intended to be used and/or activated by a single user, or may be intended to be used and/or activated by a specific group of users. For example, in a healthcare setting (e.g., a hospital, clinic, or the like), a group of patients may each have individual meters, and a user-verification mechanism may prevent one patient from inadvertently using another patient's meter. In other instances, it may be desirable to allow a healthcare provider to unlock a meter.

The meters described here may comprise any suitable user-verification mechanism. For example, in some variations, a meter may comprise a fingerprint scanner, and may be configured to store reference data relating to the fingerprint scans for one or more authorized users. This reference data may be obtained by scanning the fingerprints of one or more authorized users using the fingerprint scanner, or may be imported to the device memory via one or more memory cards, data connections, or the like. In order to unlock the meter, the meter may prompt a user to place a finger on the fingerprint scanner. After scanning the user's finger, the meter may compare the scanned information with the stored authorization data. If the meter determines that the scanned fingerprint is that of an authorized user, the meter may be configured to unlock.

In other variations, a meter may comprise a voice-activated user-verification mechanism. In some of these variations, the meter may be configured to obtain a voice sample from a potential user, and compare that voice samples previously collected from authorized users. In these variations, the meter may be configured to obtain the initial voice samples from the authorized users. In others of these variations, the user-verification mechanism may require a user to speak a certain word or sound (i.e., a verbal password) in order to unlock the device. In other variations, the user-verification mechanism may require a user to manually input a password or passcode (e.g., via one or more buttons, switches, or levers) to unlock the meter. In still other variations, the user-verification mechanism may utilize one or more devices that may interact with the meter. For example, in some of these variations the user-verification mechanism may require the presence of an RFID tag, key fob, or memory card/chip in order to unlock the device. Authorized users may carry one or more of these tags, fobs or cards.

When an authorized user unlocks a meter using one or more user-verification procedures, the meter may remain unlocked for a set period of time (e.g., thirty seconds, sixty seconds, or the like) at which point it may return to a locked configuration, or may remain unlocked until one or more events occur (e.g., completion of a sampling procedure, powering down of the device, a user input directing the meter to return to a locked configuration). It should be appreciated that when the device is in a locked configuration, the meter may be prevented from running an indexing or verification procedure, conducting a sampling procedure, allowing a user to access stored data, and/or allowing a user to change one or more device settings (e.g., changing the authorized user or users).

It should be appreciated that the meters described here may comprise any suitable number of user-verification mechanisms (e.g., zero, one, two, three, or more). In variations where a meter comprises multiple user-verification mechanisms, the meter may be configured to unlock only when all of the user-verification mechanisms have been activated or may be configured to unlock when a subset of user-verification mechanisms are activated. For example, in variations where a meter comprises a fingerprint scanner and a password based user-verification mechanism, the meter may be configured to unlock upon entry of a correct password or the scanning of an authorized fingerprint, or may be configured to require both the entry of a correct password and the scanning of an authorized fingerprint.

As mentioned briefly above, in some instances a meter may be intended for use by a single user. One or more of the user-verification mechanisms may help prevent the meter from being unlocked and/or used by another user, which may reduce the risk of potential contamination. For example, when multiple users each have a meter, such as patients in a hospital or hospice care facility, a user-verification mechanism may help reduce the likelihood that one user uses another's meter. Additionally, the user-verification mechanism may prevent inadvertent use of the meter (e.g., by a child).

In other instances, a meter may be intended for use by multiple users. In these variations, the meter may track usage of the meter by different authorized users. In some of these variations, when the meter determines that the current authorized user is different from the previous authorized user, the meter may be configured to prompt the current user to sterilize or otherwise decontaminate one or more portions of the meter housing and/or insert a new cartridge into the meter.

Meter Operation

The meters described above may be used to perform one or more testing procedures. Generally, during a testing procedure a sampling arrangement may be actuated or otherwise moved to collect a fluid sample from a sampling site. The fluid may then interact with one or more quantification members to produce a measurable reaction. This reaction may be measured or otherwise analyzed by the meter to provide a user with information relating to the fluid sample. For example, the meters may be configured to measure the glucose concentration of one or more fluid samples (e.g., a blood sample).

Initially, a user may load a cartridge (e.g., one of the cartridges described above) into the meter housing, and may activate the meter. Meter activation may comprise turning the meter on, or may comprise waking the meter from a hibernation mode. The meter may be activated before or after inserting a cartridge into the meter housing. In some instances, insertion of a cartridge into the meter housing may activate a meter.

Once a cartridge has been inserted into the meter housing and the meter has been activated, the meter may be configured to run one or more procedures to check, index, or otherwise obtain information from the cartridge. For example, in variations where the cartridge carries information (e.g., via a barcode, memory chip, or the like, as described in more detail above), the meter may be configured to read or otherwise receive this information from the cartridge. In variations where the cartridge comprises one or more barcodes, the meter housing may be configured to read the one or more barcodes via one or more barcode readers or other sensors. In some of these variations, reading the one or more barcodes comprises rotating the cartridge relative to the barcode scanner. Data received or read from the cartridge, such as one or more calibration codes, may then be uploaded or otherwise integrated into one or more algorithms for analyzing the fluid sample. In some instances, the meter may determine that a cartridge is expired based on expiration information received from the cartridge, and may alert the user to insert a new cartridge.

Additionally or alternatively, the meter housing may be configured to check and/or index the cartridge. In some of these variations, the meter housing may be configured to check to see if any or all of the sampling arrangements have been previously fired (inadvertently or as a part of a different testing procedure) and/or whether a covering material or housing of a cartridge have been compromised. The meter may then create an index of sampling arrangements that are available for use in a testing procedure (e.g., have not been previously fired and are housed within a properly sealed cartridge cell) and sampling arrangements that are unavailable for testing (e.g., have previously been fired and/or are housed within a compromised cell). If no available testing sites are available, the meter may be configured to alert the user to insert a fresh cartridge.

In some variations, an imaging system of a meter housing may check each sampling arrangement to determine whether the sampling arrangement has been previously fired and/or inadvertently activated. For example, in some variations of the cartridges described above, a sampling arrangement may have a pre-fired/cocked position and a post-firing position. In the pre-fired position, a certain portion or portions of the sampling arrangement (e.g., a reagent pad) may be outside of the viewing field of the imaging system. Conversely, once the sampling arrangement has been fired, the same portion or portions of the sampling arrangement may rest in the viewing field of the imaging system. During the checking procedure, the imaging system may visualize the interior of the cartridge cell to determine whether the specified portion or portions of the imaging system are in the viewing field. If the specified portion is identified, the meter housing may index that sampling arrangement as unavailable. The cartridge may then be rotated such that the imaging system may check the remaining cartridge cells.

Additionally or alternatively, the indexing procedure may check the seal integrity for the individual cells. For example, the variation of meter housing (600) described above with respect to FIGS. 6A-6D may be configured to check the cartridge (602) seal. Specifically, when placed inside of cartridge-receiving chamber (608), a cartridge cell may sit between light source (612) and light detector (618). In variations where the cartridge comprises one or more viewing windows (not shown), the light source (612) may be directed into the cartridge through one of the viewing windows. Conversely, one or more opaque covering materials may prevent light from exiting the cartridge cell through any aperture. If one or more of the covering materials (and thus the cell seal) is compromised (e.g., defective or previously pierced by a portion of the meter, such as a penetration member or a punch), light may exit cell through cartridge, where it may be detected by light detector (618). As such, if light detector (618) detects light (after controlling for any ambient light inside of the cartridge-receiving chamber), the meter housing may index the cell as unavailable. The meter housing may then rotate or otherwise move the cartridge such that the light source (612) may direct light into a new cell, thereby testing and indexing the remaining cells. Additionally, any suitable light source (e.g., one or more light sources of an imaging system) may be used to check the cartridge seal.

As the cartridge cells are checked using one or more of the testing procedures described immediately above, the meter housing may index each cell as either available (e.g., ready for use) or unavailable (e.g., compromised or previously fired). The meter housing may store this indexing information for later use. Once the cartridge has been tested and/or indexed, the meter may be configured to enter a standby or a ready position. When in a ready position, an aperture of a cartridge cell may be aligned with a port of the meter housing, such that a sampling arrangement housed in the cartridge may collect a sample through the port. Alternatively, when in a standby position, the cartridge may be positioned in the meter housing such that the apertures of the cartridge are out of alignment with the port. As such, the apertures may be covered or otherwise shielded by the meter housing, such that a user may be unable to access the apertures. The standby position thus may prevent a user from accessing used sampling arrangements, which may minimize a user's potential exposure to used sampling arrangements and potential needle sticks. In variations where the meter housing is configured to rotate the cartridge, the meter housing may rotate the cartridge between standby and ready positions.

In variations where the meter housing comprises a punch, the punch may be used to "open" a cartridge cell (e.g., remove or otherwise break the covering material overlaying one or more apertures of the cell) prior to placing that cartridge cell in an active position. In some variations, the cartridge may be configured to enter a ready position immediately after the cartridge has been indexed/checked. In other variations, the cartridge may be configured to enter a standby position immediately after the cartridge has been checked. In these instances, the cartridge may be moved from a standby position to a ready position by pressing one or more buttons, triggers, or sensors on the meter housing. In variations comprising a punch, the punch may align with an aperture of a cartridge cell when the meter is in a standby position. Preferably, an available sampling arrangement may be placed in alignment with the punch, such that the punch is ready to open the cartridge without first needing to rotate the cartridge.

Once the meter is in a ready position, a user may then initiate a testing procedure. If a user does not initiate a testing procedure within a preset amount of time, the meter may return to the cartridge to a standby position and enter a hibernation mode. A user may initiate a testing procedure in any suitable manner. In some variations, a user may initiate a testing procedure manually by pressing or otherwise activating a button, switch, lever, or sensor. Additionally or alternatively, a user may initiate a testing procedure by pressing a sampling site against a port of the meter. For example, where the meter housing comprises a moveable tower, such as tower (700) described in more detail above with respect to FIGS. 7A and 7B, pressure applied to cartridge via the port may cause a portion of the tower or cartridge to engage an activation element, such as those described above. The engagement between the tower or cartridge and the activation element may initiate the testing procedure. Similarly, in variations where the meter comprises a fixed tower, pressure applied to cartridge via the port may cause a strain, deflection, or other deflection in the tower, which may be measured or sensed by an activation element such as a strain gauge. As mentioned above, an activation element may require a certain force or pressure to be applied thereto before initiating the testing procedure. In these variations, a testing procedure may be initiated when a certain force or pressure has been applied to the tower and/or cartridge (e.g., via port) for a predetermined period of time.

During a testing procedure, the meter may collect and analyze a fluid sample. First, a user may place a sampling site (e.g., one or more skin surfaces) against a port. In some variations, the meter may be configured to apply vacuum, positive pressure, mechanical stimulation, and/or heat to the sampling site. Any of these stimuli may be applied before, during, or after collection of the fluid sample. For example, in some variations, a vacuum tube (such as vacuum tube (805) described above in relation to FIGS. 8A and 8B) may penetrate or otherwise enter the cartridge cell to apply vacuum to the sampling site. One or more sensors in the meter may monitor and/or control the pressure applied by the vacuum site. After applying a target pressure (or other stimulus/stimuli) for a desired period of time, the meter may activate a sampling arrangement to collect a fluid sample. Any suitable trigger mechanism, such as those described above, may trigger/activate the sampling arrangement. Once triggered, the sampling arrangement may move to pierce, puncture or otherwise penetrate the sampling site, and obtain a fluid sample therefrom. The fluid sample may be transported (e.g., pulled through the bore of a needle and/or spread across a micropatterned surface) such that the fluid sample contacts and reacts with a quantification member (e.g., a reagent pad). In some variations, the meter may be configured to determine whether the sampling arrangement has collected a sufficiently large sample, such as described in U.S. patent application Ser. No. 12/457,331, the entire content of which is hereby incorporated by reference. This reaction may produce one or more measurable results, which may be measured and analyzed by the sampling arrangement. In some variations, one or more imaging systems, such as those described above, may be used to measure the reaction between the fluid sample and the quantification member. Additionally, the meter may be configured to analyze the measured data using one or more methods or algorithms, such as those described in U.S. patent application Ser. No. 11/239,122, titled "ANALYTE DETECTION DEVICES AND METHODS WITH HEMOTCRIT/VOLUME CORRECTION AND FEEDBACK CONTROL," the content of which is hereby incorporated in its entirety, and those described in U.S. patent application Ser. Nos. 12/457,332 and 12/222,724, the contents of each were previously incorporated by reference. The meter may then store the results of the analysis and/or more communicate this information to a user (e.g., via a display or aurally).

In variations where vacuum is applied to a sampling site, the vacuum may be modulated or changed to improve collection of a fluid sample by the sampling arrangement. For example, in instances when the sampling site is a skin surface, the application of vacuum may raise the skin surface, which may pull the skin surface toward and/or into the cartridge cell. During some testing procedures, a penetration member of a sampling arrangement may come to rest in a position that may hinder or otherwise impede the ability of the penetration member to collect blood from the skin surface. To help prevent this occurrence, the meter may be configured to modulate the pressure of vacuum applied to the skin surface, which may alter the positioning of the skin surface relative to the penetration member.

For example, in some variations the meter may be configured to apply vacuum to a skin site prior to activating a sampling arrangement, which may raise the skin surface and pull the skin surface toward the cell cartridge. The vacuum pressure may be maintained as the sampling arrangement is activated, and a fluid sample is collected. If after a certain period of time (e.g., about five seconds, about ten seconds, or the like) the meter determines that the sampling arrangement has not collected a sufficiently large fluid sample, the meter may be configured to alter the vacuum pressure. For example, in some variations, the meter may be configured to partially reduce the pressure or turn off the vacuum, which may cause the skin to relax and lower. In some variations, this may reposition the penetration member within the punctured skin surface, which may alter or otherwise increase the flow of blood to the sampling site. In some variations, the meter may be configured to re-apply vacuum to the skin surface after a certain amount of time (e.g., about one second, about two seconds, about three seconds, or the like), which may re-raise the skin surface relative to the penetration member. It should also be appreciated that in some instances, modulation of the vacuum may comprise increasing the vacuum pressure. In still other variations, the vacuum may be cyclically modulated to cyclically raise and lower the skin surface relative to the penetration member.

What is claimed as new and desired to be protected by Letters Patent of the United States is:

1. An integrated body fluid sampling meter comprising:
   a meter housing comprising a contact pad;
   a tower held inside the meter housing, wherein the tower is holding a disposable cartridge, the disposable cartridge comprising a plurality of sampling arrangements;
   a force sensor coupled to the tower; and
   a processor operably coupled to the force sensor, wherein the processor receives data from the force sensor and initiates a testing procedure when a predetermined force is applied to the disposable cartridge via the contact pad.

2. The meter of claim 1 wherein the tower is fixed relative to the meter housing.

3. The meter of claim 2 wherein the force sensor comprises a strain gauge.

4. The meter of claim 3 wherein the meter is configured such that the application of the predetermined force to the disposable cartridge causes a deflection in the tower, and wherein the strain gauge measures the deflection in the tower.

5. The meter of claim 1 further comprising a detector held within the tower.

6. The meter of claim 5 further comprising an optical system, wherein the disposable cartridge comprises a plurality of viewing windows, and wherein the optical system optically connects the detector to one of the plurality of viewing windows.

7. The meter of claim 1 wherein the tower is configured to fit at least partially within a recess of the disposable cartridge.

8. The meter of claim 7 further comprising a rotation element for rotating the disposable cartridge around the tower.

9. The meter of claim 1 further comprising a light generating assembly held within the tower.

10. The meter of claim 9 wherein the light generating assembly is configured to produce light at a plurality of wavelength ranges.

11. The meter of claim 9 wherein the light generating assembly comprises a plurality of light sources.

12. The meter of claim 11 wherein each light source is configured to generate light in a different predetermined wavelength range.

13. The meter of claim 1 wherein the predetermined force comprises a force within a predetermined range.

* * * * *